(12) United States Patent
Langhals et al.

(10) Patent No.: US 8,835,484 B2
(45) Date of Patent: Sep. 16, 2014

(54) NAPHTHOCYANINES FOR USE AS CONTRAST AGENTS

(75) Inventors: Heinz Langhals, Ottobrunn (DE); Peter Laubichler, Munich (DE); Christos Haritoglou, Munich (DE); Ana Varja, Munich (DE)

(73) Assignee: Alamedics GmbH & Co. KG, Dornstadt (DE)

( * ) Notice: Subject to any disclaimer, the term of this patent is extended or adjusted under 35 U.S.C. 154(b) by 0 days.

(21) Appl. No.: 13/700,869

(22) PCT Filed: May 30, 2011

(86) PCT No.: PCT/EP2011/058837
§ 371 (c)(1),
(2), (4) Date: Feb. 6, 2013

(87) PCT Pub. No.: WO2011/151287
PCT Pub. Date: Dec. 8, 2011

(65) Prior Publication Data
US 2013/0131354 A1     May 23, 2013

(30) Foreign Application Priority Data
May 31, 2010 (DE) .......................... 10 2010 022 110

(51) Int. Cl.
*C07D 209/58* (2006.01)
*C09B 31/15* (2006.01)
*A61K 49/00* (2006.01)
*C09B 23/06* (2006.01)

(52) U.S. Cl.
CPC ............... *A61K 49/006* (2013.01); *C09B 23/06* (2013.01); *A61K 49/0034* (2013.01)
USPC .......................................... 514/411; 548/427

(58) Field of Classification Search
None
See application file for complete search history.

(56) References Cited

U.S. PATENT DOCUMENTS

2009/0320919 A1* 12/2009 Tsuchiya et al. .............. 136/256
2011/0073177 A1*  3/2011 Osawa et al. .................. 136/256

FOREIGN PATENT DOCUMENTS

| CN | 101045823 A | * | 10/2007 |
| DE | 19841985 A1 | * | 3/2000 |
| EP | 342939 A1 | * | 11/1989 |
| EP | 682288 A1 | * | 11/1995 |
| EP | 2072570 A1 | * | 6/2009 |
| JP | 02251842 A | * | 10/1990 |
| JP | 2008166119 A | * | 7/2008 |
| WO | WO 9713810 A1 | * | 4/1997 |
| WO | WO 2010079020 A1 | * | 7/2010 |

OTHER PUBLICATIONS

Langhals, et al. Journal of Medicinal Chemistry 54(11) (2011), pp. 3903-3925.*
Benzi Dyes and Pigments (2009), 83(1), pp. 111-120.*
Lim, Journal of Physical Chemistry B (2006), 110(13), 6673-6682.*
Mujumdar Bioconjugate Chem., (1996), 7, 356-362.*
Research Disclosure (1977), 161, 40 (No. 16134).*

* cited by examiner

*Primary Examiner* — Nyeemah A Grazier
(74) *Attorney, Agent, or Firm* — Clark G. Sullivan; Troutman Sanders LLP

(57) ABSTRACT

Cyanine dyes having optional sulfonic acid substituents on the aromatic nucleus have been developed for use as contrast agents for assisting in surgery and diagnosis, especially for simplifying the surgical removal of basal membranes of the eye, such as the internal limiting membrane (ILM), and for dyeing the lens capsule.

9 Claims, 5 Drawing Sheets

F

NAPHTHOCYANINES FOR USE AS CONTRAST AGENTS

Figure 1:
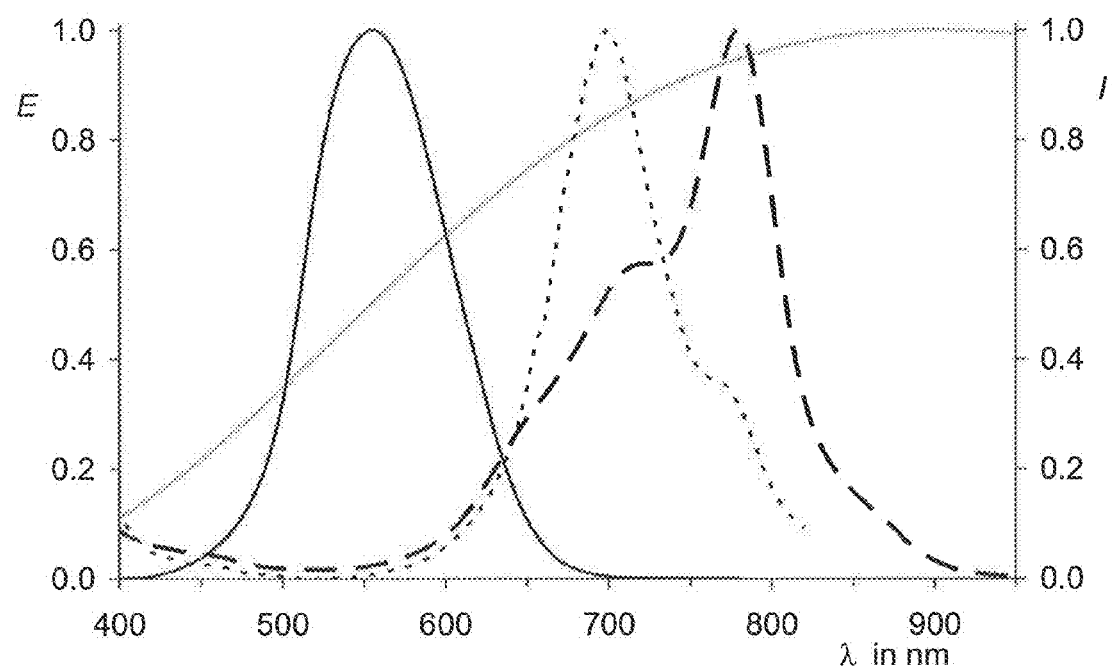

Substantial progress has been made in eye surgery in recent years, and eye surgery has made great demands on surgeons. For microsurgical operations, correctly identifying very small and transparent structures in the target tissue is a growing problem. Further progress in surgical possibilities can be achieved by increasing the visual contrast. Such an increase can be achieved via optical contrast agents that, if possible, should preferably bind to certain target tissues. There have been experiments (C. Haritoglou, A. Gandorfer, C. A. Gass et al., *Am. J. Ophthalmol.* 2002; 134: 836-841; C. Haritoglou, A. Gandorfer, C. A. Gass et al., *Am. J. Ophthalmol.* 2003; 235, 328-337) with indocyanine green (ICG, RN 3599-32-4; D. W. Heseltine, L. G. S. Brooker, U.S. Pat. No. 2,895,955), which in human medicine has already been used as an optical contrast agent in cardiology and which is recognized for its ability to decompose rapidly. Selective staining of the internal limiting membrane (ILM) may be achieved with ICG.

However, ICG is not an ideal contrast agent, despite the fact that it is selective with respect to the target tissue, because it has a toxic effect on the retina which is difficult to control (C. Haritoglou, A. Gandorfer, A. Kampik, *Invest. Ophthalmol. Vis Sci.* 2003; 44, 316-323; C. Haritoglou, A. Gandorfer, M. Schaumberger et al., *Invest. Ophthalmol Vis Sci.* 2003; 44, 2722-2729; C. Haritoglou, A. Gandorfer, C. A. Gass, A. Kampik, *Am. J. Ophthalmol.* 2004, 7, 345-348; C. Haritoglou, S. G. Priglinger, A. Gandorfer, U. Welge-Luessen, A. Kampik, *Invest. Ophthalmol. Vis Sci.* 2005, 46, 1468-1472), the cause of which is not fully understood. Moreover, a major portion of the dye's light absorption is in the near infrared (NIR) region, which is useless for recognizing staining, or is in the long wavelength region in which the light sensitivity of the human eye is low (See FIG. 1). Adaptation of such dyes as contrast agents to the special requirements of eye surgery would bring substantial progress.

An objective of the present invention was to develop a toxicologically safe optical contrast agent for use in eye surgery, especially for surgery on the anterior portion of the eye. Besides spectral adaptation of the dye with respect to spectral eye sensitivity, an advantageous dyeing effect was an objective of our work.

For use especially in eye surgery, dyes should be developed that are labile, so that staining of tissues is not permanent. Naphthocyanine dyes have been identified as interesting target structures. Their polyene structures facilitate their biological decomposition.

By shortening the central chain between the benzindole units to three methine units, it was possible to achieve a hypsochromic shift, so that the optical absorption of the dye is adapted to sensitivity characteristics of the human eye, but with a slight bathochromic shift. This takes into account the common use of tungsten halogen lamps, which emit more strongly in the longer wavelength region, for surgical operations. With optional sulfonic acid substituents, water solubility, which is advantageous for application in ophthalmology, could be facilitated.

Accordingly, the present invention provides a dye having Formula (I) for use as a contrast agent in a method for surgical treatment or in a diagnostic method,

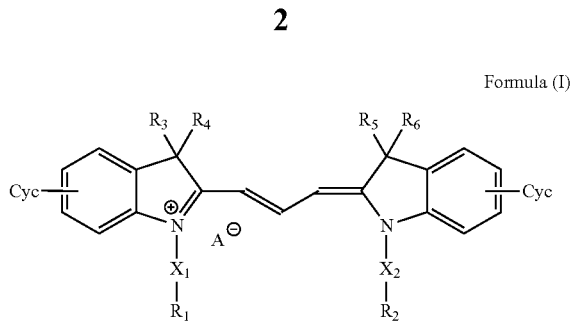

Formula (I)

wherein $X_1$ and $X_2$ are independently selected from 1 to 12 $CH_2$ units, one or more of which may be independently substituted by a carbonyl group, an oxygen atom, a sulfur atom, a cis- or trans-CH=CH— group, wherein a CH-unit may also be substituted by a nitrogen atom, an acetylenic C≡C— Group, a divalent phenyl, pyridine, or thiophene radical, a divalent naphthalene radical, wherein one or two CH— groups may be substituted by nitrogen atoms, a divalent anthracene radical, wherein one or two CH— groups may be substituted by nitrogen atoms, and wherein up to 12 individual hydrogen atoms of the $CH_2$ units may each independently from each other, and also on the same C atom, be substituted by the halogens fluorine, chlorine, bromine, or iodine, or a cyano group, or by a linear alkyl chain with up to 18 C atoms, wherein 1 to 6 $CH_2$ units may each independently be substituted by a carbonyl group, an oxygen atom, a sulfur atom, a cis- or trans-CH=CH— group, wherein a CH-unit may also be substituted by a nitrogen atom, an acetylenic C≡C— group, a divalent phenyl, pyridine, or thiophene radical, a divalent naphthalene radical, wherein one or two CH— groups may be substituted by nitrogen atoms, or a divalent anthracene radical, wherein one or two CH— groups may be substituted by nitrogen atoms;

$R_1$ and $R_2$ are independently selected from a carboxylic acid group (—COOH), a carboxylic acid ester group, a sulfonic acid group (—$SO_3H$) or a halogen atom;

$R_3$, $R_4$, $R_5$ and $R_6$ are independently selected from hydrogen and $C_1$-$C_6$ alkyl;

the Cyc groups each independently represent a benzene radical, which is bonded to the Cyc via any two adjacent CH groups of the benzene ring, forming a condensed ring system and which may be substituted with one or two sulfonic acid groups; and $A^-$ represents an optional anion that is capable of balancing the formal charge of the positively charged nitrogen atom.

Compounds of this type of structure are, for example, disclosed in WO 2008/046775 A1 (as a dye for a printing plate), in WO 2005/000218 A2 (as an intermediate for synthesizing bioconjugates), in WO 97/13810 (as an LED luminous substance or fluorescent marker) or in DE 19841985 A1 (as a pharmaceutical). Information concerning an application, particularly in eye surgery or for diagnosis in or on the eye, has not been found.

FIG. 1 shows UV/Vis spectra. Continuous black line: spectral eye sensitivity. Gray line: emission characteristic I of a tungsten halogen lamp (3200 K). Broken line: absorption spectrum of indocyanine green (ICG). Dotted line; absorption spectrum of aggregated ICG (H-aggregate).

Figure 2:
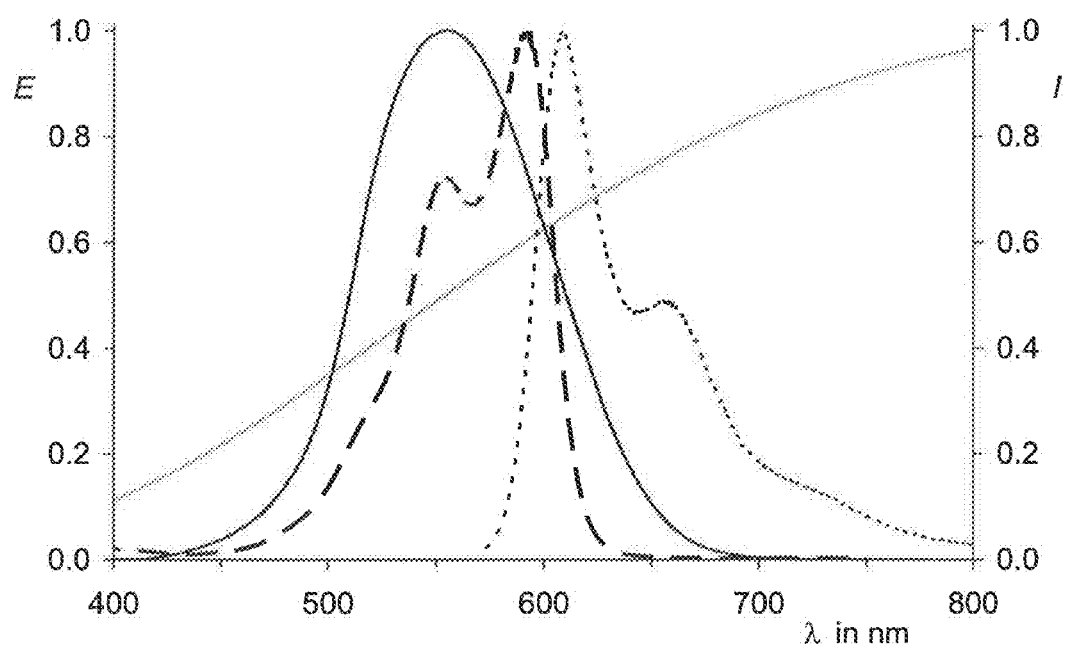
Figure 3A:
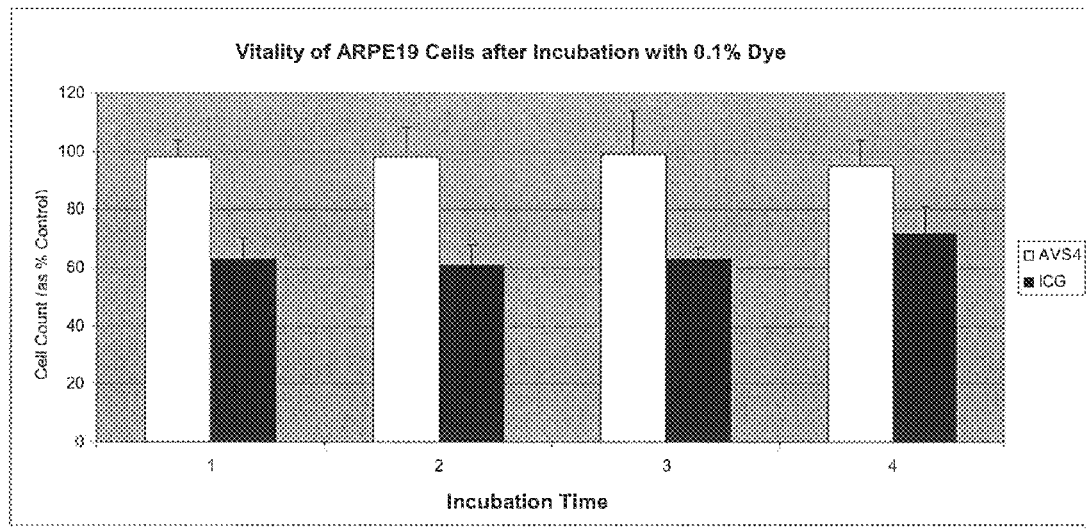
Figure 3B:
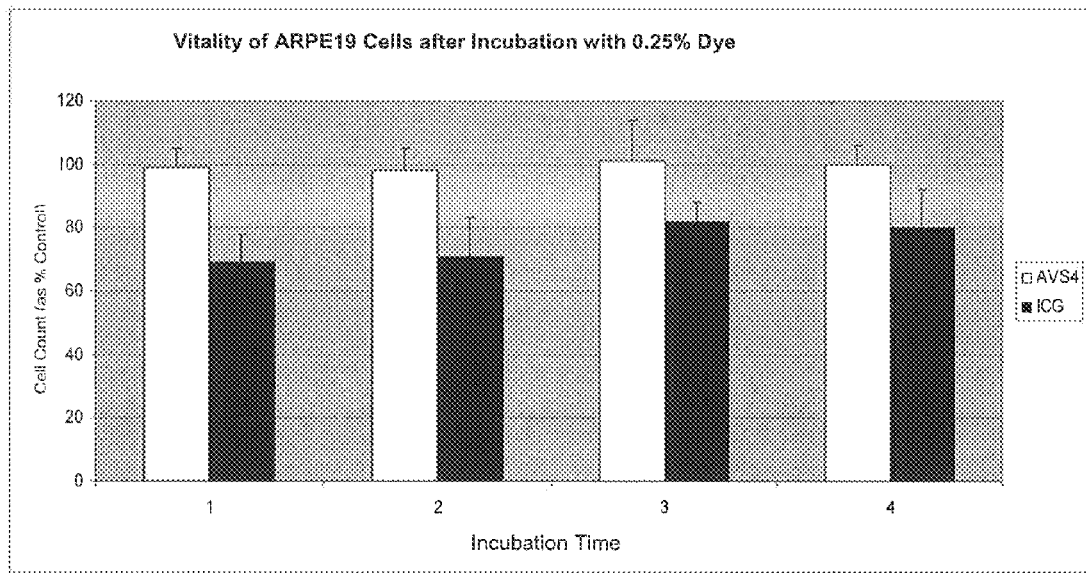
Figure 3C:
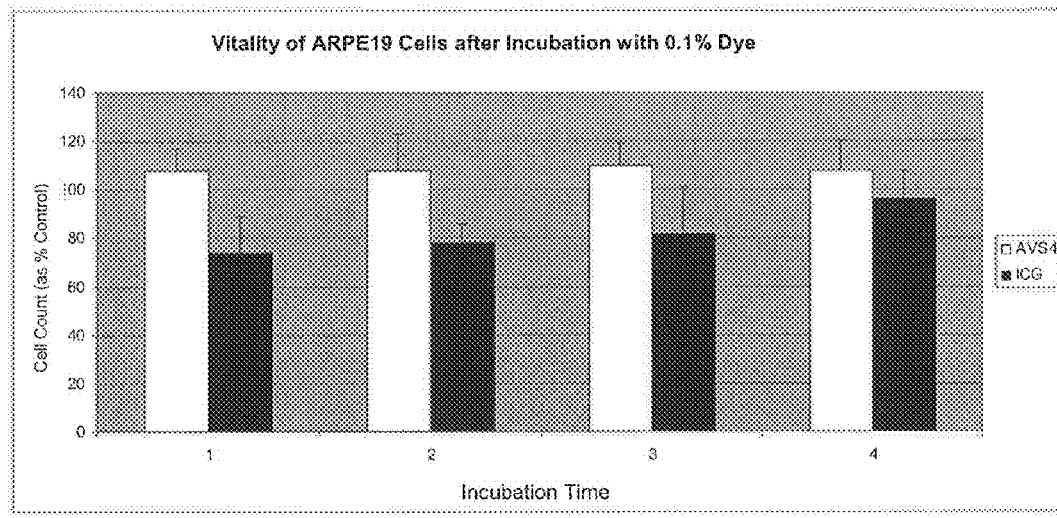
Figure 3D:
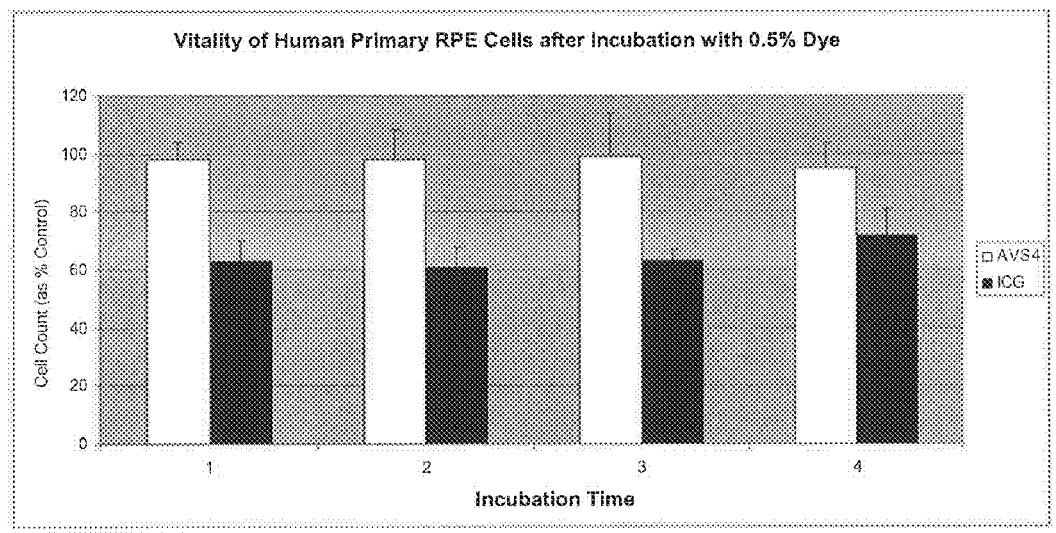
Figure 3E:
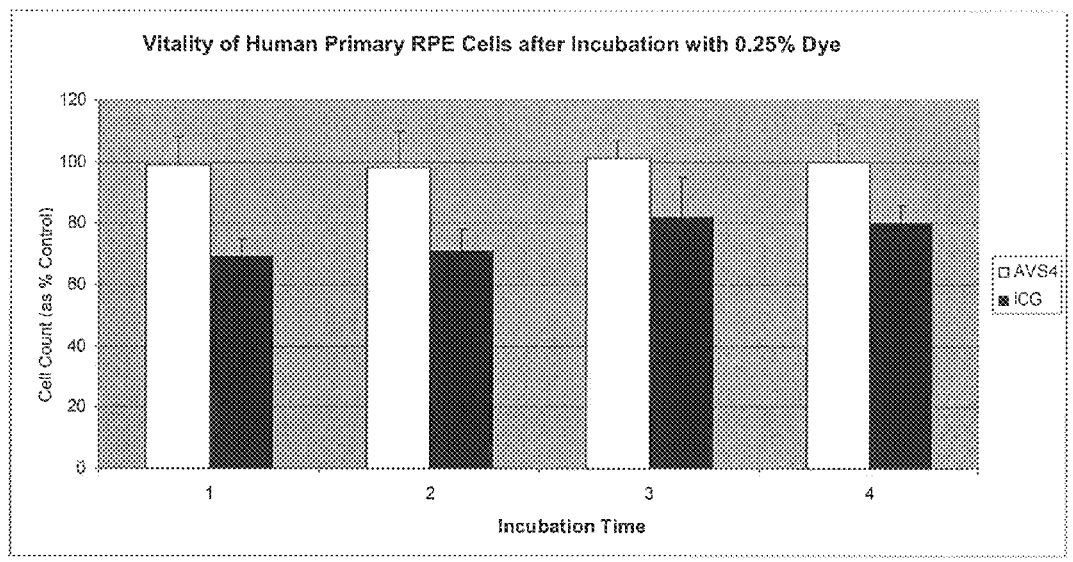
Figure 3F:
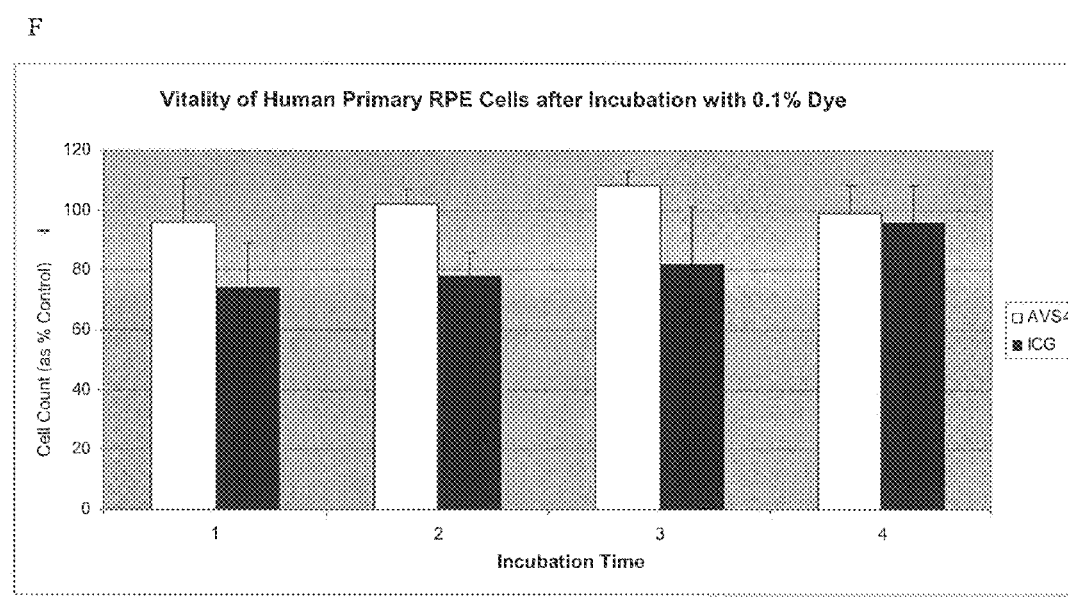

FIG. 2 shows UV/Vis spectra. Continuous black line: spectral eye sensitivity. Gray line: emission characteristic of a tungsten halogen lamp (3200 K). Broken line: absorption spectrum of compound 3i in ethanol. Dotted line: fluorescent spectrum of 3i in ethanol.

FIG. 3 shows the number of ARPE-19 and RPE cells, respectively, measured with the described colorimetric method (MTT) after treatment with the dye ARPE-19: A: 0.5%, B: 0.25%, C: 0.1% of the dye 3t (also referred to as AVS4 in the legend); RPE: D: 0.5%, E: 0.25%, F: 0.1% of the dye 3t.

Naphthocyanine dyes of Formula (I), like the preferred embodiments presented below, are especially suitable for staining tissues for surgical operations and diagnosis, because their light absorption and their pronounced fluorescence is in a spectral region that is relevant for the human eye. Toxic effects in this class of substances have not been observed. The staining achieved in the basal membrane region (in the animal model, on the porcine lens capsule) evidences bonding in the region of the target structure. By adjusting the side chains, the characteristics of the substance may be widely varied, so that in this way they can be particularly adapted to the requirements of eye surgery or diagnosis on or in the eye.

The UV/Vis absorption and fluorescence spectra of the dyes according to the invention are only slightly influenced by their substitution. A typical spectrum is shown in FIG. 2. The absorption corresponds amazingly well to the sensitivity characteristics of the human eye, and is therefore especially interesting for surgeons, because the spectra can be easily discerned. The centroid of the spectrum lies at a slightly longer wavelength than the centroid of the characteristic eye sensitivity. In practice this has proven to be decidedly beneficial, since the operating area in eye surgery is normally lit with halogen lamps, which have an emission characteristic that is also shown in FIG. 2. With the longer wavelength area being somewhat more emphasized here, the position of the spectrum has an optimum effect. The blue color of the cyanine dye has a very good contrast against the color of the tissue. The stain via the optical contrast agent is therefore easy to detect visually without additional aids.

The dyes are characterized by their strong light absorption, which results in the mentioned blue color. However, the visibility of the dye becomes poorer at very low concentration. In contrast, the surprisingly intense fluorescence of substances can be detected with greater sensitivity. One notices in FIG. 2 that large portions of the intense red fluorescent light still lie in a spectral region that is relevant for the human eye, so that they are easily visible when used to stain tissue structures. The fluorescent spectrum, while having a relatively small Stokes shift, is still sufficiently within the sensitivity characteristics of the human eye, so that a strong red fluorescence can be detected. The fluorescence quantum yield lies at 45% in solution. The strong fluorescence remains when the substances are applied to surfaces, so that the substances are also suitable for use as fluorescent contrast agents.

The naphthocyanine dyes of Formula (I), and also the preferred embodiments described below, are generally easily soluble in water. When necessary, their solubility can be increased by substituting sulfonic acid groups on the ring structures. They can therefore be used without problems in water-based electrolytic solutions typically used in eye surgery. The toxicity of the dyes is remarkably low. No toxic effects were found, even when cell cultures were exposed to high dye concentrations. Experiments with biological materials have shown that the dyes are selectively absorbed on human ILM and the eye capsule of porcine eyes, which are very suitable as a model for human eye structures. All dyes stain only the tissue of the eye chamber, while the vitreous body remains unaffected. With this, the requirements for use of the substances in eye surgery are satisfied.

Accordingly, the invention provides the dyes of Formula (I), and also the preferred embodiments described below, for application or use as contrast agents in a method for surgical treatment, especially surgical treatment of the eye. According to a further aspect, the invention provides the dyes of Formula (I), and also the preferred embodiments described below, for application or use as a contrast agent in a method of diagnosis, particularly for diagnosis on or in the eye. As previously stated, this involves use as an optical contrast agent. The dyes find application in particular in human medicine/surgery.

With respect to the use as contrast agents for surgical treatment of the eye, the preferred field of application is for surgery on the posterior portion of the eye and especially for staining the basal membrane of the eye, such as the ILM (internal limiting membrane). In this way, the membrane can be selectively treated or removed. Moreover, the dyes are outstandingly suitable for staining the lens capsule. This correspondingly applies to use as a contrast agent in a diagnostic method. Here the preferred field of application is the diagnosis of the posterior portion of the eye, especially the staining of a basal membrane of the eye, such as the ILM (internal limiting membrane). Moreover, the dyes are outstandingly suitable for staining the lens capsule.

Therefore, a method is disclosed for surgical treatment of the eye, comprising the step of applying a dye of Formula (I), or the preferred embodiments described below, as a contrast agent in the eye, particularly the application to stain the ILM or the lens capsule.

Moreover, a method is disclosed for diagnosis on or in the eye, comprising the step of applying a dye of Formula (I) or the preferred embodiments described below, as a contrast agent in the eye, particularly the application to stain the ILM or the lens capsule.

Preferably, the dye of Formula (I) is a compound having the following Formulas (IIa) or (IIb).

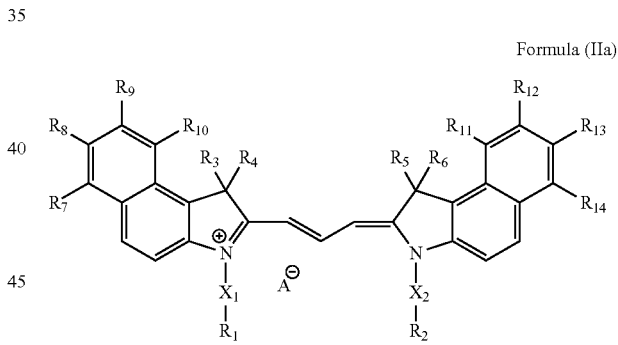

Formula (IIa)

In Formula (IIa), $X_1$, $X_2$, $R_1$, $R_2$, $R_3$, $R_4$, $R_5$, $R_6$ and $A^-$ are defined as in Formula (I); and $R_7$ to $R_{14}$ are selected from hydrogen and a sulfonic acid group, provided that no more than two sulfonic acid groups are bonded to a benzene ring.

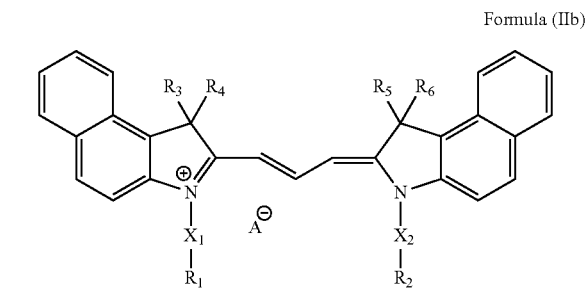

Formula (IIb)

In Formula (IIb), $X_1$, $X_2$, $R_1$, $R_2$, $R_3$, $R_4$, $R_5$, $R_6$ and $A^-$ are defined as in Formula (I).

Particularly preferred as dyes of Formula (I) are compounds having the following Formulas (III), (IV), or (V).

Formula (III)

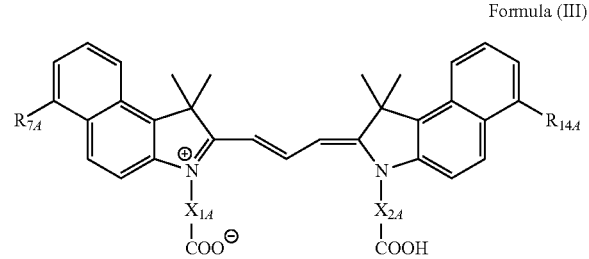

In Formula (III), $X_{1A}$ and $X_{2A}$ are independently selected from 1 to 12 $CH_2$ units, wherein 1 to 3 units may each independently be substituted by an oxygen atom or a sulfur atom, and/or may be substituted by a divalent phenyl radical; and wherein up to 4 individual hydrogen atoms of the $CH_2$ units may each independently, and also on the same C atom, be substituted by the halogens fluorine, chlorine, bromine or iodine, or a cyano group, or by a linear alkyl chain having up to 6 C atoms; and $R_{7A}$ and $R_{14A}$ are each independently selected from hydrogen and a sulfonic acid group.

Formula (IV)

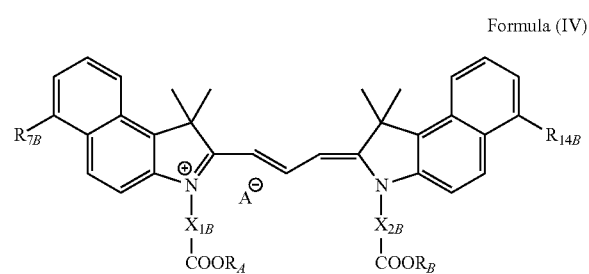

In Formula (IV), $X_{1B}$ and $X_{2B}$ are independently selected from 1 to 12 $CH_2$ units, wherein 1 to 3 units may each independently be substituted by an oxygen atom or a sulfur atom, and/or may be substituted by a divalent phenyl radical; and wherein up to 4 individual hydrogen atoms of the $CH_2$ units may each independently, and also on the same C atom, be substituted by the halogens fluorine, chlorine, bromine, or iodine, or a cyano group, or by a linear alkyl chain having up to 6 C atoms;

$R_A$ and $R_B$ are independently selected from $C_1$-$C_{12}$ alkyl, and one of the remaining $R_A$ and $R_B$ radicals may also be hydrogen;

$R_{7B}$ and $R_{14B}$ are independently selected from hydrogen and a sulfonic acid group; and $A^-$ represents an anion which has a formal charge that balances the positively charged nitrogen atom.

Formula (V)

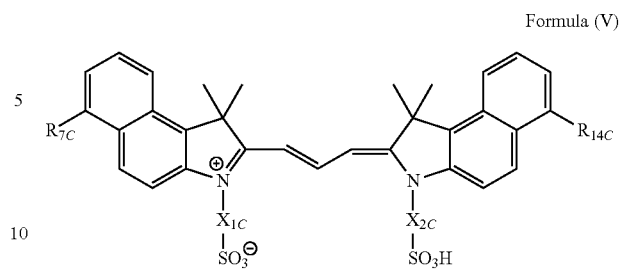

In Formula (V), $X_{1C}$ and $X_{2C}$ are independently selected from 1 to 12 $CH_2$ units, wherein 1 to 3 units may each independently be substituted by an oxygen atom or a sulfur atom, and/or may be substituted by a divalent phenyl radical; and wherein up to 4 individual hydrogen atoms of the $CH_2$ units may each independently, and also on the same C atom, be substituted by the halogens fluorine, chlorine, bromine, or iodine, or a cyano group, or by a linear alkyl chain having up to 6 C atoms; and $R_{7C}$ and $R_{14C}$ are independently selected from hydrogen and a sulfonic acid group.

The following preferred definitions also apply with reference to the compounds of Formulas (I), (IIa) and (IIb).

$X_1$ and $X_2$ are preferably independently selected from 1 to 12 $CH_2$ units, wherein 1 to 3 units may each independently be substituted by an oxygen atom or a sulfur atom, and/or may be substituted by a divalent phenyl radical; and wherein up to 4 individual hydrogen atoms of the $CH_2$ units may each independently, and also on the same C atom, be substituted by the halogens fluorine, chlorine, bromine, or iodine, or a cyano group, or by a linear alkyl chain having up to 6 C atoms. In particular, $X_1$ and $X_2$ are preferably each independently selected from 1 to 12 $CH_2$ units, 1 to 3 of which each independently may be substituted by an oxygen atom, and whereby up to 4 individual hydrogen atoms of the $CH_2$ units each independently, also on the same C atom, may be substituted by the halogens fluorine, chlorine, or bromine, or by a linear alkyl chain having up to 6 C atoms. It is especially preferred that $X_1$ and $X_2$ are independently selected from 1 to 12 $CH_2$ units.

$R_1$ and $R_2$ are preferably independently selected from a carboxylic acid group (—COOH), a carboxylic acid ester group (—COOR), and a sulfonic acid group (—$SO_3H$). For the compounds of Formula (IIb), R is preferably a linear alkyl radical with 1 to 37 C atoms. In an alternative, more preferred embodiment, for compounds of Formula (I) and well as for compounds of Formulas (IIa) and (IIb) R is an alkyl radical with 1 to 12, particularly 1 to 6, C atoms, especially preferably methyl ester and ethyl ester. It should be clear that the acid groups may also be present in deprotonated form when the compounds of Formulas (I), (IIa) and (IIb) are present in solvents, especially water. In this case, their negative formal charge is generally balanced by a cation. This may involve the nitrogen atom having a cationic formal charge in Formulas (I), (IIa) and (IIb), or an external cation (i.e., one that is not covalently bonded in the compound). Examples of such cations are an alkali metal or alkaline earth metal cation or an ammonium cation.

$R_3$, $R_4$, $R_5$ and $R_6$ are preferably independently selected from $C_1$-$C_6$ alkyl, and are especially preferably methyl.

The Cyc groups in Formula (I) according to the general definition represent a benzene radical which forms a condensed ring system with the benzene radical in the formula. The Cyc radical in the resulting system in the (e), (f) or (g)

position can thereby be annelated by the benzene radical shown. The (e) position is preferred. With regard to the optional substituents on the benzene ring, Cyc, which has one or no sulfonic acid group per benzene ring, is preferred. It should be clear that the acid group may also be present in deprotonated form when the compound of Formula (I) is present in solvents, especially water. In this case, their negative formal charge is generally balanced by a cation. This may involve the nitrogen atom having a cationic formal charge in Formula (I), or an external cation. Examples of such cations are an alkali metal or alkaline earth metal cation or an ammonium cation.

For the $R_7$-$R_{14}$ radicals in Formula (IIa), it is preferred that $R_7$ represents hydrogen or a sulfonic acid group, that $R_{14}$ represents hydrogen or a sulfonic acid group, and that $R_8$-$R_{13}$ represent hydrogen.

$A^-$ represents an optional anion which is able to balance the formal charge on the positively charged nitrogen atom. In this respect, it has been mentioned that, for example, the radicals $R_1$ and $R_2$ may represent a carboxylic acid group or a sulfonic acid group which in deprotonated form carries a negative charge. In this respect, the positive formal charge must not necessarily be balanced by an external anion $A^-$ (i.e., an anion not covalently bonded in the compound). Instead, an internal salt having a cationic and an anionic charge in the compound of Formula (I) may be formed. If an external anion is present, it can be, for example, a monovalent anion, preferably an anion of mineral acids such as fluoride, chloride, bromide, iodide, hydrogen sulfate, dihydrogen phosphate, hydrogen carbonate or nitrate. $A^-$ can also be the half equivalent of a dianion such as sulfate, carbonate or hydrogen phosphate, or also one-third of a tris-anion such as phosphate. However, $A^-$ can also be the anion of a sulfonic acid such as toluene sulfonic acid, benzene sulfonic acid or methane sulfonic acid, or also the anion of the carboxylic acid, such as acetic acid.

Salts of the compounds of Formulas (I) and (II) can, as described above, be formed by a compound with a positive formal charge on a nitrogen atom and an external anion $A^-$. They can also be formed by an anionically deprotonated acid group together with an external cation. All such salts are within the scope of the invention.

Moreover, symmetrical compounds of Formulas (I) and (II) are preferred due to their simple synthesis, wherein the groups $X_1$ and $X_2$, $R_1$ and $R_2$, $R_3$-$R_6$, $R_7$ and $R_{14}$, $R_8$ and $R_{13}$, $R_9$ and $R_{12}$, $R_{10}$ and $R_{11}$ the two Cyc groups (in Formula (I)), respectively, are identical.

The following preferred definitions apply with respect to the compounds of Formula (III).

$X_{1A}$ and $X_{2A}$ are preferably each independently selected from 1 to 12 $CH_2$ units, 1 to 3 of which each independently may be substituted by an oxygen atom, and whereby up to 4 individual hydrogen atoms of the $CH_2$ units each independently, also on the same C atom, may be substituted by the halogens fluorine, chlorine, or bromine or by a linear alkyl chain having up to 6 C atoms. In particular, $X_{1A}$ and $X_{2A}$ are preferably independently selected from 1 to 12 $CH_2$ units.

When $R_{7A}$ and $R_{14A}$ represent hydrogen, it is particularly preferred that $X_{1A}$ and $X_{2A}$ are independently selected from 2 to 9 $CH_2$ units. Especially preferred are 2, or 5 to 9 units.

The following preferred definitions apply with respect to the compounds of Formula (IV).

$X_{1B}$ and $X_{2B}$ are preferably each independently selected from 1 to 12 $CH_2$ units, 1 to 3 of which each independently may be substituted by an oxygen atom, and whereby up to 4 individual hydrogen atoms of the $CH_2$ units each independently, also on the same C atom, may be substituted by the halogens fluorine, chlorine, or bromine or by a linear alkyl chain having up to 6 C atoms. In particular, $X_{1B}$ and $X_{2B}$ are preferably independently selected from 1 to 12 $CH_2$ units.

$R_A$ and $R_B$ are preferably independently selected from $C_1$-$C_6$ alkyl, especially methyl and ethyl. Among these are preferred combinations wherein $R_A$ and $R_B$ are methyl and $X_{1B}$ and $X_{1C}$ are selected from 1 to 10 $CH_2$ units, and in which $R_A$ and $R_B$ are ethyl and $X_{1B}$ and $X_{1C}$ are selected from 1 to 5 $CH_2$ units. $R_{7B}$ and $R_{14B}$ are preferably hydrogen.

The following preferred definitions apply with respect to Formula (V).

$X_{1C}$ and $X_{2C}$ are preferably each independently selected from 1 to 12 $CH_2$ units, 1 to 3 of which each independently may be substituted by an oxygen atom, and whereby up to 4 individual hydrogen atoms of the $CH_2$ units each independently, also on the same C atoms, may be substituted by the halogens fluorine, chlorine, or bromine or by a linear alkyl chain having up to 6 C atoms. In particular, $X_{1C}$ and $X_{2C}$ are preferably independently selected from 1 to 12 $CH_2$ units, especially preferably from 1 to 5 $CH_2$ units.

Due to their simple synthesis, symmetrical compounds of Formulas (III), (IV) and (V) are also preferred in which the groups $R_{7A}$ and $R_{14A}$, $R_{7B}$ and $R_{14B}$, $R_{7C}$ and $R_{14C}$, $X_{1A}$ and $X_{2A}$, $X_{1B}$ and $X_{2B}$ or $X_{1C}$ and $X_{2C}$, and $R_A$ and $R_B$ are identical in each case.

Furthermore, the compounds of Formulas (III), (IV) and (V) may also form salts via the compound with a positive formal charge on tire nitrogen atom and an external anion $A^-$. They can also be formed by an anionic deprotonated acid group together with an external cation. Such salts are included within the scope of the invention.

The stability of the substances is determined primarily by the functional groups, as can be seen in the following Table 1. Decomposition of the solid dye results in a red coloration of the solid and the solution. Carboxylic acid esters, especially methyl ester, are particularly sensitive in addition to the bromides. Dyes without sulfonic acid groups on the aromatic nuclei are generally comparatively more stable, so that no decomposition is observed even after storage for several years.

TABLE 1

Solid cyanine dye stability comparison

| Dye | Stability |
|---|---|
| 3t | No decomposition after 3 years |
| 3u | No decomposition after 4 months |
| 3v | No decomposition after 4 months |
| 3w | Decomposition after a few days |
| 3x | No decomposition after 4 months |
| 3y | No decomposition after 4 months |
| 6a | No decomposition after 4 months |
| 6b | Decomposition after a few days |
| 6c | No decomposition after 3 months |
| 6d | Decomposition after 1 month |
| 6e | Decomposition after 2 months |
| 6f | Decomposition after 2 months |
| 6g | No decomposition after 3 months |
| 6h | Decomposition after a few days |
| 6i | Decomposition after 2 days |

Representative compounds of Formula (I) may be synthesized based on Y. Ye, S. Bloch, S. Achilefu, *J. Am. Chem. Soc.* 2004, 126, 7740-7741, starting from trimethylbenzindole, which can be substituted to prepare immonium salts 2 (scheme 1) (C. D. Geddes, *Dyes and Pigm.* 2001, 50, 151-155). In this way, various side chains having alkyl spacer groups of different lengths and polar end groups, as well as carboxyl groups and carboxylic acid ester groups, and also alkyne radicals, may be introduced. Through such structural variations, it is possible to prepare suitable structures that with multiple polar groups have the best possible tissue bonding selectivity. The immonium salts 2 can then be converted to cyanine dyes 3 with orthoformic acid ester, based on N. Shigetou, J. Miyazaki, M. Hirai, U.S. Pat. No. 5,922,618 A (Apr. 2, 1997); *Chem. Abstr.* 2001, 135, 300684. The preparation of pure dyes, which is essential for medical applications, has been found to be extremely difficult due to the predominantly polar character of the substances. Preliminary purification of the material has been achieved by precipitation from a polar solvent, using strongly lipophilic solvents such as ether. Surprisingly good results have been achieved using reverse phase chromatography. In this regard, silica gel with nonpolar side chains, such as RP18, is a particularly suitable stationary phase with which, on the preparative scale, very good results have been shown preparing the substances in pure form by column chromatography. Preferred eluents are strongly polar alcohols, such as hydrated short-chain alcohols (e.g., methanol, ethanol, propanol, in particular methanol), if necessary with the addition of acid. Illustrative eluent mixtures contain methanol, water and glacial acetic acid, or methanol, water and 2 N HCl. Also preferred in this respect is a methanol/water/acid volume ratio of 1:10:0.4.

For the preparation of illustrative compounds with sulfonic acid groups as group X in Scheme 1, one can likewise start with trimethlybenzindole 1, which may be alkylated on the nitrogen atom (2 in Scheme 1) to introduce functionalities. This dye precursor can be directly provided with sulfonic acid groups (X in 2). Butane sultone is suitable for alkylation for n=4. For other alkyl chain lengths (n=2, 5 and 10), the corresponding bromosulfonic acids were used. As an alternative, one can alkylate to the corresponding bromides (2, X=Br, n=5, 10) with excess α,ω-dibromoalkane, and substitute the bromine with sulfite to obtain the sulfonic acids 3 (X=SO$_3^-$, n=5, 10).

Sulfonic acid groups may be introduced via sulfonation as substituents on the aromatic ring system of the dye for application according to the invention, wherein a starting substance with a benzindole structure, such as trimethlybenzindole 1 in nitrobenzene, is converted with fuming sulfuric acid to a sulfonic acid, such as sulfonic acid 4. This one-step conversion is an improvement over the multi-step synthesis in the literature (L. Della-Caiana, A. Grignani, M. Cassullo, G. Caputo, PCT Int. Appl. WO 97/13810) analogous to the Fischer indole synthesis. After sulfonation, nitrobenzene can be efficiently removed via steam distillation. The compounds 4 can be alkylated analogously to 1, and as carbonyl derivatives, carboxylic acid (e.g., 5c) and the ethyl esters (e.g., 5e, 5g) can be prepared. In this way, two sulfonic acid groups could also be introduced into the benzindole, wherein the alkyl chains are provided with a terminal sulfonic acid radical (e.g., 5a).

Precursors 2, 4 and 5 can be condensed with formic acid to prepare cyanine dyes 3 and 6. The alkylation and condensation from 4 to 6 is also possible in one step. Reverse phase chromatography as previously described has also proven suitable for purifying the dye 6.

Scheme 1: illustrative synthesis of cyanine dyes 3 and 6 from 2 and 5, respectively, and orthoformic acid ester. (i) Butane sultone for n = 4 and and X = SO$_3^-$ or Br (CH$_2$)$_n$X. (ii) Pyridine or 2-picoline. (iii) Fuming sulfuric acid in nitrobenzene. (iv) Butane sultone for n = 4 and X = SO$_3^-$ or BrCH$_2$)$_n$X. (v) Fuming sulfuric acid in nitrobenzene. (vi) Pyridine or 2-picoline.

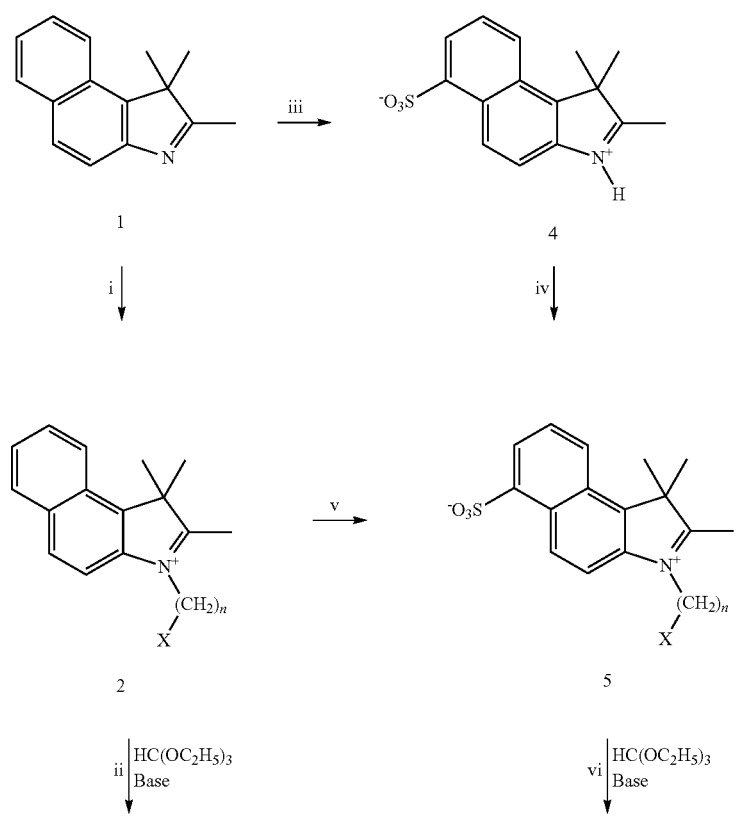

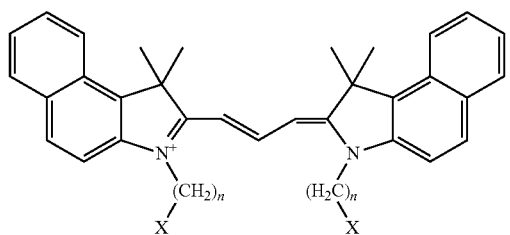

3

-continued

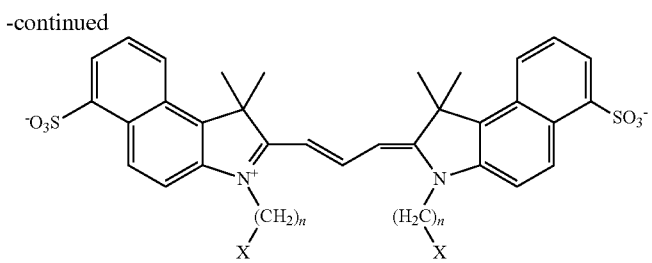

6

For use according to the invention, the dyes are advantageously formulated as an electrolytic solution, generally a water-based isotonic electrolytic solution. Known additives may be added to this electrolyte solution as needed, such as preservatives or agents for setting the viscosity and/or the osmolality. Application can be carried out by dripping the solution into the eye. The concentration of the dye in the solution may be adjusted as needed. Typically, concentrations in the range from 0.0025% to 2%, preferably 0.025% to 1%, are used (amounts are in weight-% of the dye based on the weight of the solvent).

In the following points 1 and 2, additional dyes are disclosed which may be used in the application according to the invention.

Accordingly, the invention also provides dyes having the following Formulas (V) and (VI) for application or use as contrast agents in a method for surgical treatment, particularly for surgical treatment of the eye. As previously described, this generally involves use as an optical contrast agent. The dyes are preferably applied in human medicine/surgery.

1. Carbocyanine dyes having the general Formula (V),

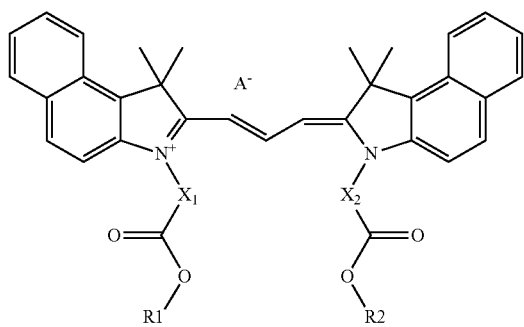

in which $X_1$ and $X_2$ can be independent from each other and represent 1 to 12 $CH_2$ units, one or more of which may each independently be substituted, respectively, by carbonyl groups, oxygen atoms, sulfur atoms, selenium atoms, tellurium atoms, cis- or trans-CH=CH— groups, wherein a unit may also be substituted by a nitrogen atom, acetylenic C≡C— groups, 1,2-, 1,3- or 1,4-substituted phenyl radicals, 2,3-, 2,4-, 2,5-, 2,6-, 3,4- or 3,5-disubstituted pyridine radicals, 2,3-, 2,4-, 2,5- or 3,4-disubstituted thiophene radicals, 1,2-, 1,3-, 1,4-, 1,5-, 1,6-, 1,7-, 1,8-, 2,3-, 2,6- or 2,7-disubstituted naphthalene radicals, wherein one or two CH groups may be substituted by nitrogen atoms, 1,2-, 1,3-, 1,4-, 1,5-, 1,6-, 1,7-, 1,8-, 1,9-, 1,10-, 2,3-, 2,6-, 2,7-, 2,9-, 2,10- or 9,10-disubstituted anthracene radicals, wherein one or two CH groups may be substituted by nitrogen atoms. Up to 12 individual hydrogen atoms of the $CH_2$ groups may each independently, also on the same C atom, be substituted by the halogens fluorine, chlorine, bromine or iodine, or the cyano group, or a linear alkyl chain with up to 18 C atoms, wherein 1 to 6 $CH_2$ units may independently be substituted by carbonyl groups, oxygen atoms, sulfur atoms, selenium atoms, tellurium atoms, cis- or trans-CH=CH— groups, wherein a unit may also be substituted by a nitrogen atom, acetylenic C≡C— groups, 1,2-, 1,3- or 1,4-substituted phenyl radicals, 2,3-, 2,4-, 2,5-, 2,6-, 3,4- or 3,5-disubstituted pyridine radicals, 2,3-, 2,4-, 2,5- or 3,4-disubstituted thiophene radicals, 1,2-, 1,3-, 1,4-, 1,5-, 1,6-, 1,7-, 1,8-, 2,3-, 2,6- or 2,7-disubstituted naphthalene radicals, wherein one or two carbon atoms may be substituted by nitrogen atoms, 1,2-, 1,3-, 1,4-, 1,5-, 1,6-, 1,7-, 1,8-, 1,9-, 1,10-, 2,3-, 2,6-, 2,7-, 2,9-, 2,10- or 9,10-disubstituted anthracene radicals, wherein one or two carbon atoms may be substituted by nitrogen atoms. Up to 12 individual hydrogen atoms of the $CH_2$ groups of the alkyl radicals may each independently, also on the same C atom, be substituted by the halogens fluorine, chlorine, bromine or iodine, or the cyano group, or a linear alkyl chain with up to 18 C atoms, wherein 1 to 6 $CH_2$ units may independently be substituted by carbonyl groups, oxygen atoms, sulfur atoms, selenium atoms, tellurium atoms, cis- or trans-CH=CH— groups, wherein a CH unit may also be substituted by a nitrogen atom, acetylenic C≡C— groups, 1,2-, 1,3- or 1,4-substituted phenyl radicals, 2,3-, 2,4-, 2,5-, 2,6-, 3,4- or 3,5-disubstituted pyridine radicals. 2,3-, 2,4-, 2,5- or 3,4-disubstituted thiophene radicals, 1,2-, 1,3-, 1,4-, 1,5-, 1,6-, 1,7-, 1,8-, 2,3-, 2,6- or 2,7-disubstituted naphthalene radicals, wherein one or two carbon atoms may be substituted by nitrogen atoms, 1,2-, 1,3-, 1,4-, 1,5-, 1,6-, 1,7-, 1,8-, 1,9-, 1,10-, 2,3-, 2,6-, 2,7-, 2,9-, 2,10- or 9,10-disubstituted anthracene radicals, wherein one or two carbon atoms may be substituted by nitrogen atoms. Instead of carrying substituents, the free valences of the methine groups, or of the quaternary C atoms, may be bonded in pairs to form rings such as cyclohexane rings, for example. The radicals $R^1$ and $R^2$ can also independently represent the halogen atoms F, Cl, Br or I.

The radicals $R^1$ and $R^2$ may be the same or different and may independently represent hydrogen, or linear alkyl radicals with at least one and not more than 37 C atoms, wherein 1 to 10 $CH_2$ units may each independently be substituted by carbonyl groups, oxygen atoms, sulfur atoms, selenium atoms, tellurium atoms, cis- or CH=CH— groups, wherein a CH unit may also be substituted by a nitrogen atom, acetylenic C≡C— groups, 1,2-, 1,3- or 1,4-substituted phenyl radicals, 2,3-, 2,4-, 2,5-, 2,6-, 3,4- or 3,5-disubstituted pyridine radicals, 2,3-, 2,4-, 2,5- or 3,4-disubstituted thiophene radicals, 1,2-, 1,3-, 1,4-, 1,5-, 1,6-, 1,7-, 1,8-, 2,3-, 2,6- or 2,7-disubstituted naphthalene radicals, wherein one or two CH groups may be substituted by nitrogen atoms, 1,2-, 1,3-, 1,4-, 1,5-, 1,6-, 1,7-, 1,8-, 1,9-, 1,10-, 2,3-, 2,6-, 2,7-, 2,9-, 2,10- or 9,10-disubstituted anthracene radicals, wherein one or two CH groups may be substituted by nitrogen atoms. Up to 12 individual hydrogen atoms of the $CH_2$ groups may each independently, also on the same C atom, be substituted by the halogens fluorine, chlorine, bromine or iodine, or the cyano group, or a linear alkyl chain with up to 18 C atoms, wherein 1 to 6 $CH_2$ units may independently be substituted by carbonyl groups, oxygen atoms, sulfur atoms, selenium atoms, tellurium atoms, cis- or trans-CH=CH— groups, wherein a CH unit may also be substituted by a nitrogen atom, acetylenic C≡C— groups, 1,2-, 1,3- or 1,4-substituted phenyl radicals, 2,3-, 2,4-, 2,5-, 2,6-, 3,4- or 3,5-disubstituted pyridine radicals, 2,3-, 2,4-, 2,5- or 3,4-disubstituted thiophene radicals, 1,2-, 1,3-, 1,4-, 1,5-, 1,6-, 1,7-, 1,8-, 2,3-, 2,6- or 2,7-disubstituted naphthalene radicals, wherein one or two carbon atoms may be substituted by nitrogen atoms, 1,2-, 1,3-, 1,4-, 1,5-, 1,6-, 1,7-, 1,8-, 1,9-, 1,10-, 2,3-, 2,6-, 2,7-, 2,9-, 2,10- or 9,10-disubstituted anthracene radicals, wherein one or two carbon atoms may be substituted by nitrogen atoms. Up to 12 individual hydrogen atoms of the $CH_2$ groups of the alkyl radicals may each independently, also on the same C atom, be substituted by the halogens fluorine, chlorine, bromine or iodine, or cyano groups, or a linear alkyl chain with up to 18 C atoms, wherein 1 to 6 $CH_2$ units may independently be substituted by carbonyl groups, oxygen atoms, sulfur atoms, selenium atoms, tellurium atoms, cis- or trans-CH=CH— groups, wherein a CH unit may also be substituted by a nitrogen atom, acetylenic C≡C— groups, 1,2-, 1,3- or 1,4-substituted phenyl radicals, 2,3-, 2,4-, 2,5-, 2,6-, 3,4- or 3,5-disubstituted pyridine radicals, 2,3-, 2,4-, 2,5- or 3,4-disubstituted thiophene radicals, 1,2-, 1,3-, 1,4-, 1,5-, 1,6-, 1,7-, 1,8-, 2,3-, 2,6- or 2,7-disubstituted naphthalene radicals, wherein one or two carbon atoms may be substituted by nitrogen atoms, 1,2-, 1,3-, 1,4-, 1,5-, 1,6-, 1,7-, 1,8-, 1,9-, 1,10-, 2,3-, 2,6-, 2,7-, 2,9-, 2,10- or 9,10-disubstituted anthracene radicals, wherein one or two carbon atoms may be substituted by nitrogen atoms. Instead of carrying substituents, the free valences of the methine groups, or of the quaternary C atoms, may be bonded in pairs to form rings such as cyclohexane rings, for example. The radicals $R^1$ and $R^2$ can also independently represent the halogen atoms F, Cl, Br or I.

$A^-$ represents a monovalent anion, preferably an anion of mineral acids, such as fluoride, chloride, bromide, iodide, hydrogen sulfate, dihydrogen phosphate, hydrogen carbonate or nitrate. $A^-$ can also be the half equivalent of a dianion such as sulfate, carbonate or hydrogen phosphate, or also one-third of a tris-anion such as phosphate. $A^-$ can, however, also be the anion of a sulfonic acid, such as toluene sulfonic acid, benzene sulfonic acid or methane sulfonic acid, or also the anion of a carboxylic acid, such as acetic acid.

2. Cyanine dyes of die general Formula (VI),

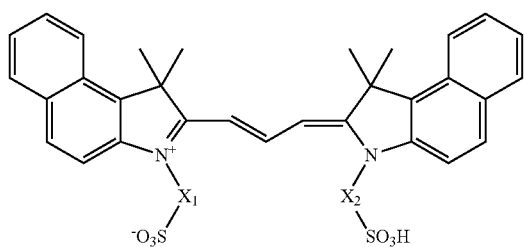

6 wherein $X_1$ and $X_2$ have the same meaning as in 1.

The following are also important aspects of the present invention:

3. A method characterized in that the cyanine dyes according to 1 and 2 are purified via reverse phase chromatography. The preferred stationary phase is RP18, the preferred eluents contain water, methanol and glacial acetic acid or, alternatively, aqueous 2 N HCl, and a preferred proportionality is 1:10:0.4.
4. Use of the substances according to 1 to 2 as optical contrast agents in the medical field, preferably in the human medical field.
5. Use of the substances according to 1 to 2 as optical contrast agents in ophthalmology and especially in eye surgery. Preferred applications be in surgery on the posterior portion of the eye, especially for removal of the ILM, and for staining and treating the lens capsule.
6. Use of the substances according to 1 to 2 as optical fluorescent contrast agents in the medical field, especially in the human medical field, particularly in ophthalmology and especially in eye surgery. Preferred applications lie in surgery on the posterior portion of the eye and in particular for removal of the ILM and for staining and treating the lens capsule.

EXAMPLES

General

IR spectra: Perkin Elmer Spectrum BX II, using a diamond anvil cell; UV/Vis spectra: Varian Cary 5000 and Bruins Omega 20; fluorescence spectra: Varian Eclispe; NMR spectroscopy: Varian Vnmrs 600 (600 MHz, 400 MHz, 200 MHz); mass spectrometry: Thermo Finnigan LQT FT.

Synthesis of Cyanine Dye Precursors

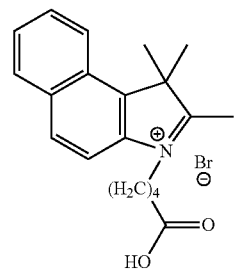

2b 3-(4-carboxybutyl)-1,1,2-trimethyl-1H-benzo[e]indolenium bromide (2b)

1,1,2-Trimethylbenzo[e]indole (360 mg, 1.65 mmol) and 5-bromovaleric acid (300 mg, 1.65 mmol) were heated (bath 145° C.) under reflux for 1 h, allowed to cool, stirred with diethyl ether (50.0 mL) for 3 h, filtered off and washed with dichloromethane. Yield: 243 mg (38%) colorless solid. Melting point 187° C. IR (ATR): $\tilde{v}$=2984 (w), 2913 (w), 1713 (s), 1581 (m), 1524 (m), 1474 (m), 1455 (m), 1397 (m), 1368 (w), 1258 (w), 1236 (w), 1208 (m), 1171 (s), 1157 (s), 1084 (w), 896 (w), 869 (w), 811 (s), 791 (m), 762 (m), 747 (w), 692 (w), 641 $cm^{-1}$ (w). $^1$H NMR (200 MHz, DMSO-$d_6$): δ=8.49-8.31 (m, 1H, $H_{aromatic}$), 8.30-8.13 (m, 2H, $H_{aromatic}$), 8.09-7.96 (m, 1H, $H_{aromatic}$), 7.85-7.70 (m, 1H, $H_{aromatic}$), 7.68-7.50 (m, 1H, $H_{aromatic}$), 4.60 (t, 2H, $NCH_2$, $^3J$=7.0 Hz), 2.94 (s, 3H, CH$_3$), 2.32 (t, 2H, CH$_2$, $^3$J=7.2 Hz), 1.99-1.84 (m, 2H, CH$_2$), 1.76 (s, 6H, 2×CH$_3$), 1.73-1.63 ppm (m, 2H, CH$_2$). HRMS (ESI) (C$_{20}$H$_{24}$NO$_2$$^+$): calculated 310.1802. found 310.1801, Δ=−0.1 mmu.

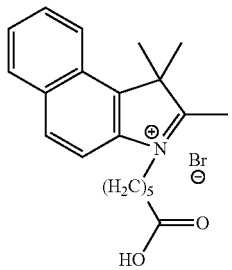

3-(5-carboxypentyl)-1,1,2-trimethyl-1H-benzo[e]indolenium bromide (2c)

1,1,2-Trimethylbenzo[e]indole (500 mg, 2.30 mmol) and 6-bromohexanoic acid (1.15 g, 6.00 mmol) were dissolved in DMPU (10.0 mL), heated for 2 d under inert gas at 120° C., filtered off and washed with diethyl ether and dichloromethane. Yield: 350 mg (37%) slightly blue solid. $^1$H NMR (400 MHz, CD$_3$OD): δ=8.33 (d, 1H, H$_{aromatic}$, $^3$J=8.5 Hz), 8.25 (d, 1H, H$_{aromatic}$, $^3$J=9.1 Hz), 8.17 (d, 1H, H$_{aromatic}$, $^3$J=8.3 Hz), 8.01 (d, 1H, H$_{aromatic}$, $^3$J=9.0 Hz), 7.81 (ddd, 1H, H$_{aromatic}$, $^4$J=1.3 Hz, $^3$J=6.9 Hz, $^3$J=8.4 Hz), 7.73 (ddd, 1H, H$_{aromatic}$, $^4$J=1.1 Hz, $^3$J=7.0 Hz, $^3$J=8.1 Hz), 4.70-4.60 (m, 2H, NCH$_2$), 2.89 (s, 3H, CH$_3$), 2.36 (t, 2H, CH$_2$, $^3$J=7.0 Hz), 2.18-1.97 (m, 2H, CH$_2$), 1.85 (s, 6H, 2×CH$_3$), 1.79-1.68 (m, 2H, CH$_2$), 1.68-1.53 ppm (m, 2H, CH$_2$). $^{13}$C NMR (100 MHz, CD$_3$OD): δ=196.1, 175.7, 174.2, 138.3, 137.3, 131.0, 129.6, 128.3, 127.7, 127.3, 123.0, 112.3, 55.9, 32.8, 27.3, 25.6, 24.0, 20.9 ppm. HRMS (ESI) (C$_{21}$H$_{26}$NO$_2$$^+$): calculated 324.1958. found 324.1956, Δ=−0.2 mmu.

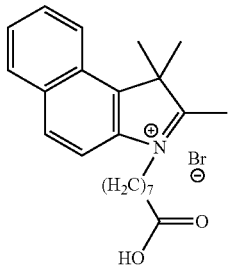

3-(7-carboxyheptyl)-1,1,2-trimethyl-1H-benzo[e]indolenium bromide (2d)

1,1,2-Trimethylbenzo[e]indole (938 mg, 4.48 mmol) and 8-bromoctanoic acid (1.00 g, 4.48 mmol) were heated for 2 h at 120° C., allowed to cool, stirred with diethyl ether (50.0 mL) for 16 h, filtered off, dissolved in a small amount of dichloromethane and precipitated with diethyl ether. Yield: 1.69 mg (87%) black solid, melting point 150° C. IR (ATR): $\tilde{v}$=3055 (w), 2928 (s), 2854 (w), 1720 (s), 1633 (w), 1580 (m), 1522 (m), 1463 (m), 1382 (w), 1178 (w), 1085 (w), 827 (w), 744 cm$^{-1}$ (w). $^1$H NMR (600 MHz, CD$_3$Cl$_3$): δ=8.12 (d, 1H, H$_{aromatic}$, $^3$J=8.8 Hz), 8.10-8.04 (m, 2H, H$_{aromatic}$, $^3$J=8.3 Hz), 7.80 (d, 1H, H$_{aromatic}$, $^3$J=8.9 Hz), 7.73 (ddd, 1H, H$_{aromatic}$, $^4$J=1.1 Hz, $^3$J=7.0 Hz, $^3$J=8.3 Hz), 7.68-7.65 (m, 1H, H$_{aromatic}$), 4.86-4.82 (m, 2H, NCH$_2$), 3.22 (s, 3H, CH$_3$), 2.36 (t, 1H, CH$_2$, $^3$J=7.1 Hz), 2.01-1.97 (m, 2H, CH$_2$), 1.86 (s, 6H, 2×CH$_3$), 1.65-1.60 (m, 2H, CH$_2$), 1.57-1.51 (m, 2H, CH$_2$), 1.46-1.40 (m, 2H, CH$_2$), 1.39-1.33 ppm (m, 2H, CH$_2$). $^{13}$C NMR (150 MHz, CDCl$_3$): δ=195.6, 176.5, 138.2, 137.1, 133.7, 131.5, 130.1, 128.6, 127.9, 127.6, 122.8, 112.5, 55.9, 49.6, 34.0, 28.3, 28.1, 28.0, 26.2, 24.2, 22.7, 16.0 ppm. HRMS (ESI) (C$_{23}$H$_{30}$NO$_2$$^+$): calculated 352.2271. found 352.2271, Δ=0 mmu.

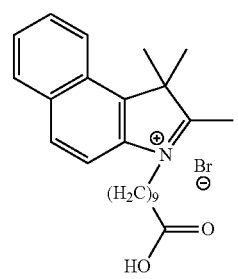

3-(9-carboxynonyl)-1,1,2-trimethyl-1H-benzo[e]indolenium bromide (2e)

1,1,2-Trimethylbenzo[e]indole (345 mg, 1.65 mmol) and 10-bromodecanoic acid (414 mg, 1.65 mmol) were heated for 1 h at 120° C., allowed to cool, stirred with diethyl ether (50 mL) for 16 h, filtered off, dissolved in dichloromethane and precipitated with ethyl acetate (2 d). Yield: 112 mg (15%) blue oil. IR (ATR): $\tilde{v}$=2925 (s), 2851 (s), 1720 (s), 1633 (w), 1615 (w), 1580 (m), 1522 (m), 1463 (m), 1371 (s), 1242 (w), 1211 (w), 1173 (m), 1098 (w), 1044 (m), 997 (w), 866 (w), 825 (m), 790 (m), 746 (m), 694 cm$^{-1}$ (w). $^1$H NMR (200 MHz, CDCl$_3$): δ=8.14-8.05 (m, 3H, H$_{aromatic}$), 7.79-7.65 (m, 3H, H$_{aromatic}$), 4.85 (t, 2H, NCH$_2$, $^3$J=8.8 Hz), 3.21 (s, 3H, CH$_3$), 2.35 (t, 2H, CH$_2$, $^3$J=7.1 Hz), 2.03-1.93 (m, 2H, CH$_2$), 1.87 (s, 6H, 2×CH$_3$) 1.69-1.29 ppm (m, 12H, 6×CH$_2$). $^{13}$C NMR (150 MHz, CDCl$_3$): δ=195.5, 177.0, 171.2, 138.2, 137.2, 133.7, 131.5, 130.1, 128.7, 127.9, 127.6, 122.8, 112.4, 60.4, 55.8, 49.8, 34.0, 28.5, 26.5, 24.4, 22.7, 21.0, 16.1, 14.2 ppm. HRMS (ESI) (C$_{25}$H$_{34}$NO$_2$$^+$): calculated 380.2584. found 380.2582, Δ=−0.2 mmu.

3-(10-carboxydecyl)-1,1,2-trimethyl-1H-benzo[e]indolenium bromide (2f)

1,1,2-Trimethylbenzo[e]indole (345 mg, 1.65 mmol) and 11-bromoundecanoic acid (437 mg, 1.65 mmol) were heated for 1 h at 120° C., allowed to cool, stirred with diethyl ether (50.0 mL) for 16 h and freed from solvents via decantation. Yield: 640 mg (82%) brown oil. IR (ATR): $\tilde{v}$=3059 (w), 2964 (w), 2925 (s), 2852 (s), 1937 (w), 1709 (s), 1624 (w), 1598 (w), 1574 (m), 1520 (m), 1463 (m), 1429 (w), 1384 (w), 1362 (w), 1350 (w), 1244 (m), 1218 (m), 1118 (w), 1023 (w), 979 (w), 862 (w), 819 (s), 747 (s), 722 (w), 694 (w), 668 (w), 640 (w), 609 cm$^{-1}$ (w). $^1$H NMR (600 MHz, CDCl$_3$): δ=8.0.1 (d, 1H, H$_{aromatic}$, $^3$J=8.4 Hz), 7.94 (d, 1H, H$_{aromatic}$, $^3$J=7.8 Hz), 7.85 (d, 1H, H$_{aromatic}$, $^3$J=8.6 Hz), 7.82 (d, 1H, $^3$J=8.5 Hz) 7.54 (ddd, 1H, H$_{aromatic}$, $^4$J=1.3 Hz, $^3$J=6.8 Hz, $^3$J=8.3 Hz), 7.44 (ddd, 1H, H$_{aromatic}$, $^4$J=1.1 Hz, $^3$J=6.8 Hz, $^3$J=8.0 Hz), 3.40 (t, 2H, NCH$_2$, $^3$J=6.9 Hz), 2.41 (s, 3H, CH$_3$), 2.36 (t, 2H, CH$_2$, $^3$J=7.5 Hz), 1.87-1.82 (m, 2H, CH$_2$), 1.71-1.63 (m, 2H, CH$_2$), 1.55 (s, 6H, 2×CH$_3$), 1.45-1.39 (m, 2H, CH$_2$), 1.38-1.33 (m, 2H, CH$_2$), 1.32-1.27 ppm (m, 8H, 4×CH$_2$). $^{13}$C NMR (150 MHz, CDCl$_3$): δ=189.9, 178.6, 149.9, 138.4, 132.3, 129.6, 128.9, 128.6, 126.3, 124.4, 122.4, 119.6, 55.2, 34.2, 33.9, 32.8, 29.3, 29.2, 29.1, 28.6, 28.1, 24.8, 22.6, 14.9 ppm. HRMS (ESI) (C$_{26}$H$_{36}$NO$_2^+$): calculated 394.2740. found 394.2743, Δ=0.3 mmu.

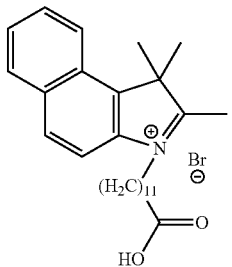

3-(11-carboxyundecyl)-1,1,2-trimethyl-1H-benzo[e]indolenium bromide (2g)

1,1,2-Trimethylbenzo[e]indole (450 mg, 2.15 mmol) and 12-bromododecanoic acid (200 mg, 0.72 mmol) were reacted (2.5 h) and worked up analogously to 3-(9-carboxynonyl)-1,1,2-trimethyl-1H-benzo[e]indolenium bromide (2e). Yield: 297 mg (84%) brown solid. IR (ATR): $\tilde{v}$=2926 (m), 2850 (m), 2489 (w), 1779 (w), 1750 (w), 1716 (s), 1634 (s), 1615 (w), 1581 (s), 1523 (s), 1476 (w), 1463 (s), 1388 (m), 1317 (w), 1270 (m), 1212 (w), 1174 (m), 1113 (w), 1101 (w), 1036 (w), 1026 (w), 998 (m), 940 (w), 900 (w), 865 (m), 827 (s), 789 (m), 745 (s), 719 (m), 694 (m), 616 cm$^{-1}$ (w). $^1$H NMR (200 MHz, CDCl$_3$): δ=8.14-8.01 (m, 3H, H$_{aromatic}$), 7.82-7.60 (m, 3H, H$_{aromatic}$), 4.84 (t, 2H, NCH$_2$, $^3$J=7.4 Hz), 3.20 (s, 3H, CH$_3$), 2.31 (t, 2H, CH$_2$, $^3$J=7.3 Hz), 1.86 (s, 6H, 2×CH$_3$), 1.62-1.20 ppm (m, 18H, 9×CH$_2$). $^{13}$C NMR (150 MHz, CDCl$_3$): δ=176.0, 138.3, 137.2, 133.7, 131.4, 130.1, 128.7, 128.0, 127.6, 122.8, 112.3, 55.8, 33.6, 0 28.7, 28.6, 28.4, 28.4, 28.3, 28.3, 28.1, 26.4, 24.4, 22.7, 16.0, 3.1, 3.0, 2.7 ppm. HRMS (ESI) (C$_{27}$H$_{38}$NO$_2^+$): calculated 408.2897. found 408.2895, Δ=−0.2 mmu.

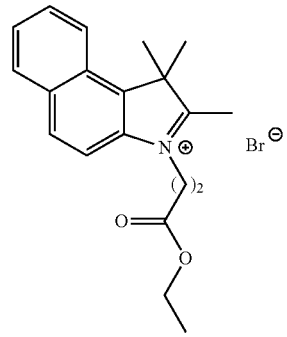

3-(2-ethoxycarbonylethyl)-1,1,2-trimethyl-1H-benzo[e]indolenium bromide (2l)

1,1,2-Trimethylbenzo[e]indole (462 mg, 2.21 mmol) and 3-bromopropionic acid ethyl ester (2 g, 11 mmol) were reacted and worked up analogously to 3-(9-carboxynonyl)-1,1,2-trimethyl-1H-benzo[e]indolenium bromide (2e). Yield: 656 mg (62%, content 81% in addition to starting material according to $^1$H NMR spectroscopy) brown solid. IR (ATR): $\tilde{v}$=3381 (m), 3056 (w), 2923 (w), 2852 (w), 2350 (w), 2287 (w), 1711 (s), 1626 (m), 1588 (s), 1554 (w), 1520 (s), 1479 (w), 1423 (m), 1357 (m), 1277 (w), 1224 (w), 1168 (w), 1142 (w), 1127 (m), 1012 (m), 971 (w), 930 (w), 898 (w), 867 (w), 806 (s), 786 (m), 746 (s), 726 (w), 685 (w), 676 (w), 652 cm$^{-1}$ (w). $^1$H NMR (200 MHz, CDCl$_3$): δ=8.13-8.01 (m, 4H, CH$_{aromatic}$), 7.75-7.60 (m, 2H, CH$_{aromatic}$), 5.23 (t, 2H, NCH$_2$, $^3$J=6.0 Hz), 4.09 (q, 2H, OCH$_2$CH$_3$, $^3$J=7.2 Hz), 3.0 (s, 3H, CH$_3$), 2.41-2.39 (m, 2H, CH$_2$COOCH$_2$CH$_3$), 1.77 (s, 6H, 2×CH$_3$), 1.14 ppm (t, 3H, OCH$_2$CH$_3$, $^3$J=7.2 Hz). HRMS (ESI) (C$_{20}$H$_{24}$NO$_2^+$): calculated 310.1796. found 310.1762, Δ=−0.4 mmu.

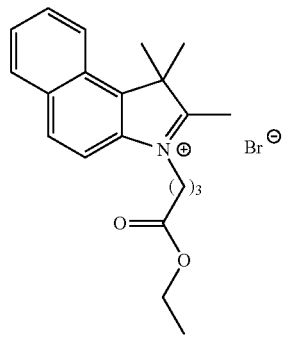

3-(3-ethoxycarbonylpropyl)-1,1,2-trimethyl-1H-benzo[e]indolenium bromide (2m)

1,1,2-Trimethylbenzo[e]indole (429 mg, 2.05 mmol) and 4-bromobutyric acid ethyl ester (2 g, 10 mmol) were reacted (2 h) and worked up analogously to 3-(9-carboxynonyl)-1,1,2-trimethyl-1H-benzo[e]indolenium bromide (2e). Yield: 496 mg (21%, content 35% in addition to starting material according to $^1$H NMR spectroscopy) gray solid. IR (ATR): $\tilde{v}$=3381 (w), 3056 (m), 2350 (w), 2287 (w), 1711 (s), 1626 (m), 1588 (s), 1520 (m), 1276 (m), 971 (w), 867 (m), 786 (m), 746 (m), 726 (w), 685 (m), 676 (w), 652 cm$^{-1}$ (w). $^1$H NMR (200 MHz, CDCl$_3$): δ=8.13-7.97 (m, 4H, CH$_{aromatic}$), 7.76-7.58 (m, 2H, CH$_{aromatic}$), 5.00 (t, 2H, NCH$_2$, $^3$J=8.1 Hz), 4.08 (q, 2H, OCH$_2$CH$_3$, $^3$J=7.2 Hz), 3.27 (s, 3H, CH$_3$), 2.76 (t, 2H, CH$_2$COOCH$_2$CH$_3$, 6.8 Hz), $^3$J=2.37-2.21 (m, 2H, CH$_2$), 1.85 (s, 6H, 2×CH$_3$), 1.21 ppm (t, 3H, OCH$_2$CH$_3$, $^3$J=7.2 Hz). HRMS (ESI) (C$_{21}$H$_{26}$NO$_2$$^+$): calculated 324.1958. found 324.1962, Δ=0.4 mmu.

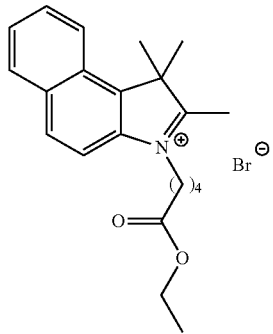

2n 3-(4-ethoxycarbonylbutyl)-1,1,2-trimethyl-1H-benzo[e]indolenium bromide (2n)

1,1,2-Trimethylbenzo[e]indole (400 mg, 1.91 mmol) and 5-bromopentanoic acid ethyl ester (2 g, 9.56 mmol) were reacted and worked up analogously to 3-(9-carboxynonyl)-1,1,2-trimethyl-1H-benzo[e]indolenium bromide (2e). Yield: 513 mg (26%, content 40% in addition to starting material according to $^1$H NMR spectroscopy) blue solid. IR (ATR): $\tilde{\nu}$=3381 (m), 3056 (w), 2350 (w), 2287 (w), 1711 (s), 1626 (w), 1588 (s), 1520 (m), 1277 (w), 971 (w), 898 (w), 867 (w), 786 (m), 746 (s), 726 (w), 685 (m), 676 (w), 652 cm$^{-1}$ (w). $^1$H NMR (200 MHz, DMSO-d$_6$): δ=8.40-8.03 (m, 4H, CH$_{aromatic}$), 7.83-7.53 (m, 2H, CH$_{aromatic}$), 4.61 (t, 2H, NCH$_2$, $^3$J=7.2 Hz), 4.03 (q, 2H, OCH$_2$CH$_3$, $^3$J=6.9 Hz), 2.95 (s, 3H, CH$_3$), 2.10 (t, 2H, CH$_2$COOCH$_2$CH$_3$, $^3$J=7.3 Hz), 1.99-1.83 (m, 2H, CH$_2$), 1.76 (s, 6H, 2×CH$_3$), 1.73-1.66 (m, 2H, CH$_2$), 1.14 ppm (t, 3H, OCH$_2$CH$_3$, $^3$J=7.1 Hz). HRMS (ESI) (C$_{22}$H$_{28}$NO$_2$$^+$): calculated 338.2115. found 338.2118, Δ=0.3 mmu.

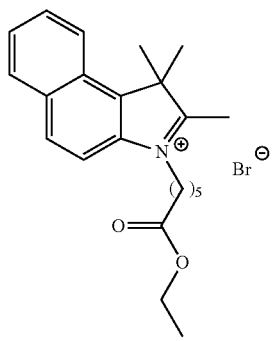

2o 3-(5-ethoxycarbonylpentyl)-1,1,2-trimethyl-1H-benzo[e]indolenium bromide (2o)

1,1,2-Trimethylbenzo[e]indole (31 mg, 0.15 mmol) and 6-bromohexanoic acid ethyl ester (100 mg, 0.45 mmol) were reacted (1 h) and worked up analogously to 3-(7-carboxyheptyl)-1,1,2-trimethyl-1H-benzo[e]indolenium bromide (2d). Yield: 41 mg (63%) grayish solid. IR (ATR): $\tilde{\nu}$=3851 (w), 3420 (s), 2921 (m), 2851 (w), 1726 (s), 1622 (w), 1589 (m), 1556 (w), 1520 (m), 1477 (m), 1352 (m), 1227 (w), 1067 (w), 1014 (m), 941 (w), 899 (w), 805 (m), 786 (w), 744 (m), 728 (w), 652 cm$^{-1}$ (w). $^1$H NMR (200 MHz, CD$_3$OD): δ=8.36-8.15 (m, 3H, CH$_{aromatic}$), 8.02 (d, 1H, CH$_{aromatic}$, $^3$J=9.1 Hz), 7.86-7.66 (m, 2H, CH$_{aromatic}$), 4.65 (t, 2H, NCH$_2$, $^3$J=7.5 Hz), 4.07 (q, 2H, OCH$_2$CH$_3$, $^3$J=7.2 Hz), 2.38 (t, 2H, CH$_2$COOCH$_2$CH$_3$, $^3$J=7.0 Hz), 2.10-2.02 (m, 2H, CH$_2$), 1.99 (s, 3H, CH$_3$), 1.85 (s, 6H, 2×CH$_3$), 1.77-1.52 (m, 4H, CH$_2$), 1.20 ppm (t, 3H, OCH$_2$CH$_3$, $^3$J=7.1 Hz). HRMS (ESI) (C$_{23}$H$_{30}$NO$_2$$^+$): calculated 352.2271. found 352.2275, Δ=0.4 mmu.

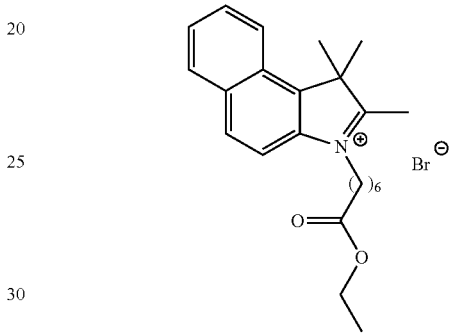

2p 3-(6-ethoxycarbonylhexyl)-1,1,2-trimethyl-1H-benzo[e]indolenium bromide (2p)

1.05 g (5.04 mmol) 1,1,2-trimethylbenzo[e]indole and 7-bromoheptanoic acid ethyl ester (400 mg, 1.68 mmol) were heated for 2 h at 120° C. After cooling, diethyl ether (50 mL) was added, stirred for 16 h, and filtered off. Yield: 348 mg (22%, content 48% in addition to starting material according to $^1$H NMR spectroscopy) grayish solid. $^1$H NMR (600 MHz, CDCl$_3$): δ=8.11-8.07 (m, 4H, CH$_{aromatic}$), 7.75-7.70 (m, 2H, CH$_{aromatic}$), 4.88 (t, 2H, NCH$_2$, $^3$J=7.3 Hz), 4.09 (q, 2H, OCH$_2$CH$_3$, $^3$J=7.1 Hz), 3.23 (s, 3H, CH$_3$), 2.28 (t, 2H, CH$_2$COOCH$_2$CH$_3$, $^3$J=7.3 Hz), 2.03-1.99 (m, 2H, CH$_2$), 1.88 (s, 6H, 2×CH$_3$), 1.65-1.59 (m, 2H, CH$_2$), 1.56-1.52 (m, 2H, CH$_2$), 1.46-1.40 (m, 2H, CH$_2$), 1.22 ppm (t, 3H, OCH$_2$CH$_3$, $^3$J=7.1 Hz). HRMS (ESI) (C$_{24}$H$_{32}$NO$_2$$^+$): calculated 366.2428. found 366.2426, Δ=−0.2 mmu.

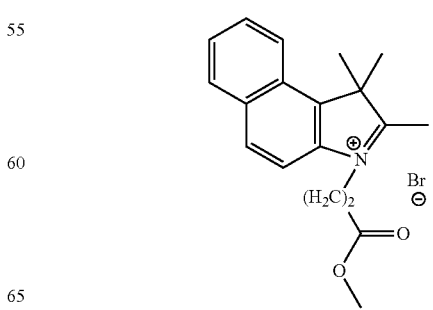

2h

3-(2-methoxycarbonylethyl)-1,1,2-trimethyl-1H-benzo[e]indolenium bromide (2h)

1,1,2-Trimethylbenzo[e]indole (250 mg, 1.19 mmol) and 3-bromopropionic acid methyl ester (400 mg, 2.39 mmol) were heated for 1 h at 120° C., after cooling combined with diethyl ether (50.0 mL), stirred for 16 h, filtered off, dissolved in chloroform, precipitated with diethyl ether and aspirated. Yield: 321 mg (49%, content 68% in addition to starting material according to $^1$H NMR spectroscopy) brown solid. $^1$H NMR (200 MHz, CDCl$_3$): δ=8.10-7.98 (m, 4H, CH$_{aromatic}$), 7.78-7.59 (m, 2H, CH$_{aromatic}$), 5.24 (t, 2H, NCH$_2$, $^3$J=5.9 Hz), 3.58 (s, 3H, OCH$_3$), 3.27 (t, 2H, CH$_2$COOCH$_2$CH$_3$, $^3$J=6.0 Hz), 3.24 (s, 3H, CH$_3$), 1.84 ppm (s, 6H, 2×CH$_3$). HRMS (ESI) (C$_{19}$H$_{22}$NO$_2^+$): calculated 296.1645. found 296.1638, Δ=−0.7 mmu.

3-(4-methoxycarbonylbutyl)-1,1,2-trimethyl-1H-benzo[e]indolenium bromide (2i)

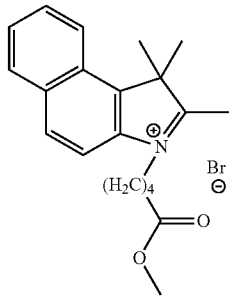

1,1,2-Trimethylbenzo[e]indole (214 mg, 1.02 mmol) and 5-bromopentanoic acid methyl ester (200 mg, 1.02 mmol) were heated for 2 h at 120° C., allowed to cool, combined with diethyl ether (50.0 mL), stirred for 16 h and filtered off. Yield: 253 mg (28%, content 46% in addition to starting material according to $^1$H NMR spectroscopy) grayish solid. $^1$H NMR (200 MHz, CDCl$_3$): δ=8.15-8.01 (m, 4H, CH$_{aromatic}$), 7.87-7.63 (m, 2H, CH$_{aromatic}$), 4.97 (t, 2H, NCH$_2$, $^3$J=7.4 Hz), 3.64 (s, 3H, OCH$_3$), 3.25 (s, 3H, CH$_3$), 2.46 (t, 2H, $^3$J=6.8 Hz), 2.19-1.98 (m, 2H, CH$_2$), 1.89 (s, 6H, 2×CH$_3$), 1.78-1.70 ppm (m, 2H, CH$_2$). HRMS (ESI) (C$_{21}$H$_{26}$NO$_2^+$): calculated 324.1958. found 324.1949, Δ=−0.9 mmu.

3-(9-methoxycarbonylnonyl)-1,1,2-trimethyl-1H-benzo[e]indolenium bromide (2j)

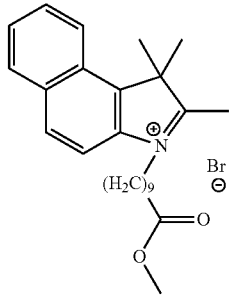

1,1,2-Trimethylbenzo[e]indole (947 mg, 4.52 mmol) and 10-bromodecanoic acid methyl ester (400 mg, 1.50 mmol) were reacted and worked up analogously to 3-(4-methoxycarbonylbutyl)-1,1,2-trimethyl-1H-benzo[e]indolenium bromide (2i). Yield: 310 mg (18% content, 40% in addition to starting material according to $^1$H NMR spectroscopy) grayish solid. $^1$H NMR (200 MHz, CDCl$_3$): δ=8.14-8.00 (m, 4H, CH$_{aromatic}$), 7.79-7.60 (m, 2H, CH$_{aromatic}$), 4.86 (t, 2H, NCH$_2$, $^3$J=7.7 Hz), 3.64 (s, 3H, OCH$_3$), 3.22 (s, 3H, CH$_3$), 2.27 (t, 2H, $^3$J=7.3 Hz), 2.08-1.90 (m, 4H, 2×CH$_2$), 1.88 (s, 6H, 2×CH$_3$), 1.60-1.30 ppm (m, 10H, 5×CH$_2$), HRMS (ESI) (C$_{26}$H$_{36}$NO$_2^+$): calculated 394.2741. found 394.2729, Δ=−1.2 mmu.

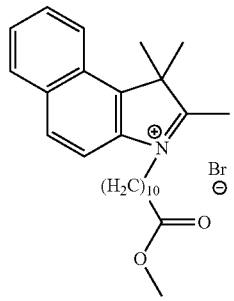

3-(10-methoxycarbonyldecyl)-1,1,2-trimethyl-1H-benzo[e]indolenium bromide (2k)

1,1,2-Trimethylbenzo[e]indole (1.2 g, 5.73 mmol) and 11-bromoundecanoic acid methyl ester (400 mg, 1.43 mmol) were reacted (1.5 h) and worked up analogously to 3-(4-methoxycarbonylbutyl)-1,1,2-trimethyl-1H-benzo[e]indolenium bromide (2i). Yield: 270 mg (25%, content 65% in addition to starting material according to $^1$H NMR spectroscopy) bluish-gray solid. $^1$H NMR (400 MHz, CDCl$_3$): δ=8.11-7.99 (m, 4H, CH$_{aromatic}$), 7.75-7.60 (m, 2H, CH$_{aromatic}$), 4.86 (t, 2H, NCH$_2$, $^3$J=7.7 Hz), 3.64 (s, 3H, OCH$_3$), 3.22 (s, 3H, CH$_3$), 2.27 (t, 2H, $^3$J=7.5 Hz), 2.01-1.93 (m, 2H, CH$_2$), 1.88 (s, 6H, 2×CH$_3$), 1.61-1.54 (m, 2H, CH$_2$), 1.51-1.44 (m, 2H, CH$_2$), 1.40-1.32 (m, 2H, CH$_2$), 1.29-1.21 ppm (m, 8H, 4×CH$_2$). HRMS (ESI) (C$_{27}$H$_{38}$NO$_2^+$): calculated 408.2897. found 408.2895, Δ=−0.2 mmu.

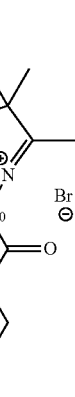

3-(10-propargyloxycarbonyldecyl)-1,1,2-trimethyl-1H-benzo[e]indolenium bromide (2q)

1,1,2-Trimethylbenzo[e]indole (517 mg, 2.47 mmol) and 11-bromoundecanoic acid propargyl ester (I. Ott et al., J.

Med. Chem. 2005, 48, 622-629) (250 mg, 0.82 mmol) were reacted (1.5 h) and worked up analogously to 3-(4-methoxycarbonylbutyl)-1,1,2-trimethyl-1H-benzo[e]indolenium bromide (2i). Yield: 148 mg (35%) black solid. HRMS (ESI) ($C_{29}H_{38}NO_2^+$): calculated 432.2897. found 432.2899, Δ=0.2 mmu.

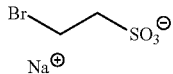

Sodium 2-bromoethane sulfonate 1,2-Dibromomethane (6.2 mL, 72 mmol) and sodium sulfite (3 g, 24 mmol) were dissolved in a mixture of ethanol (25 mL) and distilled water (20 mL), heated for 6 h under reflux, allowed to cool, extracted three times with chloroform, dried with magnesium sulfate and concentrated under vacuum. Yield: 8.3 g (55%) colorless solid, melting point 289° C. IR (ATR): $\tilde{v}$=3600 (w), 3528 (w), 3408 (s), 2980 (w), 2946 (w), 2087 (w), 1635 (w), 1615 (s), 1435 (m), 1411 (m), 1294 (m), 1263 (w), 1202 (m), 1168 (m), 1112 (w), 1041 (s) 794 (w), 779 (w), 750 (w), 674 (w), 617 cm$^{-1}$ (w). HRMS (ESI) ($C_2H_4BrO_3S^-$): calculated 186.9070. found 186.9070. Δ=0 mmu.

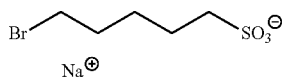

Sodium 5-bromopentane sulfonate 1,5-Dibromopentane (16.4 g, 71 mmol), sodium sulfite (3 g, 24 mmol), ethanol (25 mL) and water (20 mL) were reacted and worked up analogously to sodium 2-bromoethane sulfonate. Yield: 7.4 g (41%) colorless solid. IR (ATR): $\tilde{v}$=3485 (m), 3411 (w), 2978 (w), 2930 (m), 2908 (w), 2895 (w), 2867 (w), 2851 (w), 1636 (w), 1616 (w), 1487 (w), 1466 (m), 1410 (w), 1390 (w), 1329 (w), 1314 (w), 1293 (w), 1262 (w), 1224 (m), 1207 (s), 1180 (s), 1044 (s), 988 (w), 938 (w), 823 (w), 804 (w), 792 (w), 729 (w), 618 cm$^{-1}$ (w). HRMS (ESI) ($C_5H_{11}BrNaO_3S^+$): calculated 252.9504. found 252.9820, Δ=31.6 mmu.

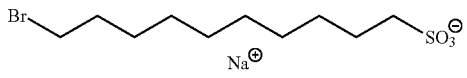

Sodium 10-bromodecane sulfonate 1,10-Dibromodecane (7.5 g, 25 mmol), sodium sulfite (1.4 g, 11 mmol), ethanol (25 mL) and water (20 mL) were reacted and worked up analogously to sodium 2-bromoethane sulfonate. Yield: 1.8 g (23%) colorless solid, melting point 342° C., IR (ATR): $\tilde{v}$=3541 (s), 3481 (s), 2916 (s), 2874 (m), 2853 (s), 2095 (w), 1627 (m), 1472 (w), 1307 (w), 1281 (w), 1250 (w), 1230 (m), 1197 (m), 1178 (s), 1055 (m), 1044 (m), 968 (w), 796 (m), 721 (w), 640 (w), 608 cm$^{-1}$ (m). HRMS (ESI) ($C_{10}H_{21}BrNaO_3S^+$): calculated 323.0287. found 323.0602, Δ=31.5 mmu.

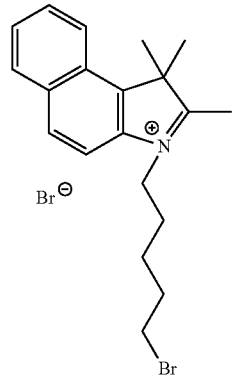

3-(5-bromopentyl)-1,1,2-trimethyl-1H-benzo[e]indolenium bromide (2w)

1,1,2-Trimethylbenzo[e]-indole (1.0 g, 4.8 mmol) and 1,5-dibromopentane (0.22 mL, 1.6 mmol) were heated for 2 h at 120° C., allowed to cool, combined with diethyl ether (30 mL), stirred for 16 h, aspirated, dissolved in a small amount of dichloromethane and precipitated with diethyl ether. Yield: 860 mg (54%, content 44% in addition to starting material as determined by $^1$H NMR spectroscopy) brown solid, melting point 123° C. IR (ATR): $\tilde{v}$=3393 (s), 3058 (w), 2976 (m), 2928 (m), 2867 (w), 2714 (w), 2667 (w), 2588 (w), 2362 (m), 2336 (w), 1982 (w), 1739 (w), 1702 (w), 1632 (w), 1618 (w), 1582 (s), 1522 (s), 1464 (s), 1388 (w), 1367 (w), 1352 (w), 1279 (w), 1206 (m), 1148 (w), 1130 (w), 1039 (w), 1007 (w), 938 (w), 897 (w), 871 (w), 817 (s), 803 (s), 790 (m), 746 (s), 711 (w), 692 (w), 668 cm$^{-1}$ (w). $^1$H NMR (200 MHz, CDCl$_3$): δ=8.04-7.91 (m, 4H, H$_{aromatic}$), 7.70-7.49 (m, 2H, H$_{aromatic}$), 4.95 (t, 2H, NCH$_2$, $^3$J=7.3 Hz), 3.30 (s, 3H, CH$_3$), 3.25-3.19 (m, 4H, 2×CH$_2$), 2.41-2.25 (m, 2H, CH$_2$), 2.17-2.03 (m, 2H, CH$_2$), 1.77 ppm (s, 6H, 2×CH$_3$).

In addition, further signals belonging to the starting product were present in the NMR spectrum, resulting in a conversion of 44%.

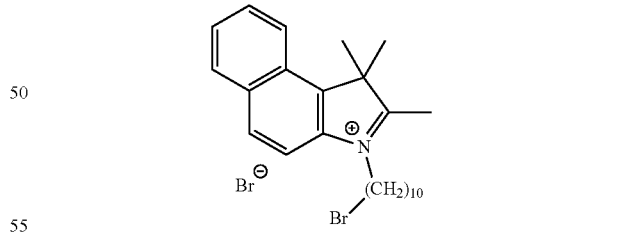

3-(10-bromodecyl)-1,1,2-trimethyl-1H-benzo[e]indolenium bromide (2x)

1,1,2-Trimethylbenzo[e]indole (2.0 g, 10 mmol) and 1,10-dibromodecane (0.75 mL, 3.3 mmol) were heated for 40 min at 120° C., allowed to cool, combined with diethyl ether (30 mL), stirred for 16 h and aspirated. Yield: 1.3 g (32%, content 40% in addition to starting material), melting point 109° C. IR (ATR): $\tilde{v}$=3394 (s, br), 3056 (w), 2977 (w), 2926 (s), 2854 (m), 2717 (w), 2665 (w), 2616 (w), 2591 (w), 2455 (w), 2038

(w), 1824 (w), 1633 (w), 1316 (w), 1582 (s), 1523 (m), 1465 (s), 1391 (w), 1368 (w), 1352 (w), 1334 (w), 1281 (w), 1216 (m), 1175 (w), 1147 (w), 1130 (w), 1040 (w), 1007 (w), 982 (w), 932 (w), 896 (w), 870 (w), 817 (m), 790 (w), 746 (w), 692 (w), 659 cm$^{-1}$ (w). $^1$H NMR (200 MHz, CDCl$_3$): δ=8.14-7.98 (m, 4H, H$_{aromatic}$), 7.76-7.58 (m, 2H, H$_{aromatic}$), 4.93-4.82 (m, 2H, NCH$_2$), 3.29 (s, 3H, CH$_3$), 2.10-1.84 (m, 2H, CH$_2$), 1.86 (s, 6H, 2×CH$_3$), 1.84-1.76 (m, 4H, 2×CH$_2$), 1.70-1.20 ppm (m, 12H, 6×CH$_2$). In addition, the signals of the starting material were present in the NMR spectrum, resulting in a conversion of 40%. HRMS (ESI) (C$_{25}$H$_{35}$BrN$^+$): calculated 428.1947. found 428.1948, Δ=0.1 mmu.

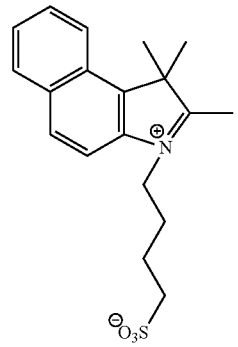

1,1,2-Trimethyl-3-pentyl-1H-benzo[e]indolenium bromide 1,1,2-Trimethylbenzo[e]indole (690 mg, 3.31 mmol) and 1-bromopentane (0.20 mL, 1.6 mmol) were heated for 1.5 h at 120° C., allowed to cool, combined with diethyl ether (20 mL), stirred for 16 h and aspirated. Yield: 182 mg (24%, content 80% in addition to starting material corresponding to $^1$H NMR spectroscopy) brown solid, which was used in the subsequent condensation reaction without further purification, melting point 241° C. IR (ATR): ṽ=3398 (w), 3052 (w), 2929 (w), 2869 (w), 2709 (w), 2588 (w), 1819 (w), 1643 (m), 1584 (s), 1524 (m), 1464 (s), 1394 (m), 1218 (w), 1204 (w), 1148 (w), 1007 (w), 846 (w), 802 (s), 744 cm$^{-1}$ (s). $^1$H NMR (200 MHz, CDCl$_3$): δ=8.15-8.01 (m, 4H, H$_{aromatic}$), 7.75-7.62 (m, 2H, H$_{aromatic}$), 4.88 (t, 2H, NCH$_2$, $^3$J=7.7 Hz), 3.23 (s, 3H, CH$_3$) 2.05-1.96 (m, 2H, CH$_2$), 1.89 (s, 6H, 2×CH$_3$), 1.71-1.68 (m, 2H, CH$_2$), 1.56-1.40 (m, 2H, CH$_2$), 0.92 ppm (t, 3H, CH$_2$CH$_3$. $^3$J=7.0 Hz). In addition, the signals of the starting material were present in the NMR spectrum, resulting in a conversion of 80%. HRMS (ESI) (C$_{20}$H$_{26}$N$^+$): calculated 280.2060. found 280.2057, Δ=−0.3 mmu.

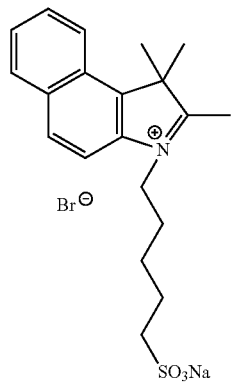

3-(4-Sulfobutyl)-1,1,2-trimethyl-1H-benzo[e]indole (2t)

1,1,2-Trimethylbenzo[e]indole (1.0 g, 4.8 mmol) and 1,4-butane sultone (0.50 mL, 4.8 mmol) were heated for 2.5 h at 130° C., filtered off after cooling, washed with acetone and dried for 3 h at 100° C. Yield: 1.13 g (70%) gray-white solid, melting point 263° C. (Lit. review: H. Langhals, C. Haritoglou, Der Ophthalmologe 2009, 106, 16-20: 266° C.). IR (ATR): ṽ=3435 (m), 2939 (w), 1636 (w), 1584 (w), 1523 (w), 1468 (m), 1199 (s), 1034 (s), 872 (w), 824 (m), 791 (w), 758 (m), 737 cm$^{-1}$ (w). $^1$H NMR (400 MHz, CD$_3$OD): δ=8.32 (d, 1H, H$_{aromatic}$, $^3$J=8.5 Hz), 8.24 (d, 1H, H$_{aromatic}$, $^3$J=8.9 Hz), 8.16 (d, 1H, H$_{aromatic}$, $^3$J=8.2 Hz), 8.06 (d, 1H, H$_{aromatic}$, $^3$J=9.0 Hz), 7.80 (ddd, 1H, H$_{aromatic}$, $^4$J=1.3 Hz, $^3$J=6.9 Hz, $^3$J=8.4 Hz), 7.71 (ddd, 1H, H$_{aromatic}$, $^4$J=1.1 Hz, $^3$J=6.9 Hz, $^3$J=8.1 Hz), 4.70-4.64 (m, 2H, NCH$_2$), 2.91 (t, 2H, CH$_2$SO$_3^-$, $^3$J=7.1 Hz), 2.26-2.18 (m, 2H, CH$_2$), 2.03-1.94 (m, 2H, CH$_2$), 1.84 (s, 6H, 2×CH$_3$), 1.30 ppm (s, 3H, CH$_3$). $^{13}$C NMR (100 MHz, CD$_3$OD): δ=196.6, 138.7, 137.5, 134.1, 131.3, 129.9, 128.5, 127.9, 127.5, 123.2, 112.7, 56.1, 49.9, 26.4, 23.0, 22.1, 21.2 ppm. HRMS (ESI) (C$_{19}$H$_{24}$NO$_3$S): calculated 346.1471. found 346.1473, Δ=0.2 mmu.

3-(5-Sulfopentyl)-1,1,2-trimethyl-1H-benzo[e]indolenium bromide sodium salt (2u)

1,1,2-Trimethylbenzo[e]indole (744 mg, 3.56 mmol) and sodium 5-bromopentane sulfonate (300 mg, 1.18 mmol) were heated for 2 h at 150° C., allowed to cool, combined with diethyl ether (30 mL), stirred for 16 h, filtered off, dissolved in a small amount of methanol and precipitated with diethyl ether. Yield: (59%) blue-black solid, melting point 213° C., IR (ATR): $\tilde{v}$=3054 (w), 2963 (m), 2928 (m), 2866 (w), 2661 (w), 2614 (w), 2587 (w), 2456 (w), 1960 (w), 1915 (w), 1819 (w), 1782 (w), 1700 (w), 1645 (m), 1621 (m), 1570 (s), 1519 (s), 1466 (s), 1431 (m), 1377 (m), 1346 (m), 1282 (w), 1263 (w), 1242 (m), 1218 (s), 1206 (m), 1180 (m), 1036 (w), 1022 (m), 974 (m), 929 (m), 871 (s), 827 (s), 803 (s), 755 (s), 756 (s), 682 (w), 666 (m), 608 cm$^{-1}$ (m). $^1$H NMR (200 MHz, CDCl$_3$): δ=8.35-8.00 (m, 4H, H$_{aromatic}$), 7.82-7.64 (m, 2H, H$_{aromatic}$), 4.64 (t, 2H, NCH$_2$, $^3$J=7.5 Hz), 3.56 (t, 2H, CH$_2$SO$_3$H, $^3$J=6.3 Hz), 2.11-1.98 (m, 2H, CH$_2$), 1.82 (s, 6H, 2×CH$_3$), 1.79 (s, 3H, CH$_3$), 1.62-1.50 ppm (m, 4H, 2×CH$_2$). HRMS (ESI) (C$_{20}$H$_{25}$NNaO$_3$S$^+$): calculated 328.1447. found 328.1447, Δ=0 mmu.

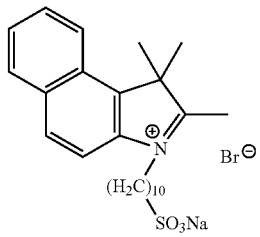

3-(10-Sulfodecyl)-1,1,2-trimethyl-1H-benzo[e]indolenium bromide sodium salt (2v)

3-(10-Bromodecyl)-1,1,2-trimethyl-1H-benzo[e]indolenium bromide (600 mg, 1.18 mmol) and sodium sulfite (50 mg, 0.39 mmol) were dissolved in a mixture of ethanol (5.0 mL) and water (3.0 mL), heated for 6 h under reflux and then allowed to cool. The organic phase (1,10-dibromodecane) was discarded, and the lower aqueous phase was extracted three times with chloroform. The combined chloroform phases were dried over magnesium sulfate and concentrated under vacuum. Yield: 165 mg (79%) colorless solid. IR (ATR): $\tilde{v}$=2923 (s), 2853 (m), 1703 (m), 1521 (m), 1465 (w), 1352 (w), 1208 (m), 1035 (m), 810 (s), 750 cm$^{-1}$ (m). $^1$H NMR (200 MHz, CDCl$_3$): δ=8.09-7.91 (m, 4H, H$_{aromatic}$), 7.77-7.64 (m, 2H, H$_{aromatic}$), 3.93-3.90 (m, 2H, NCH$_2$), 3.65-3.54 (m, 2H, CH$_2$SO$_3$H), 2.38 (s, 3H, 2×CH$_3$), 2.07-1.97 (m, 2H, CH$_2$), 1.83-1.76 (4H, 2×CH$_2$), 1.55 (s, 6H, 2×CH$_3$), 1.39-1.22 ppm (m, 10H, 5×CH$_2$). MS (EI$^+$): m/z (%): 556.6 [M$^+$ 2HNa].

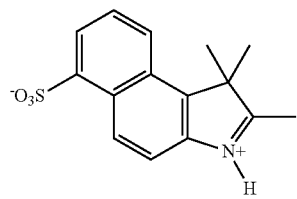

1,1,2-Trimethyl-1H-sulfobenzo[e]indole (4)

1,1,2-Trimethylbenzo[e]indole (1.0 g, 5.0 mmol) was dissolved in nitrobenzene (5.0 mL), carefully combined dropwise with fuming sulfuric acid with ice cooling (0.65 mL, 5.0 mmol, SO$_3$ content 65%, temperature increase to 20° C., cooling until filming stopped), allowed to warm to room temperature, stirred for 4 h, freed of nitrobenzene via decantation, followed by steam distillation (until odorless) and concentrated. Yield: 1.00 g (69%) black viscous oil, which was used in the subsequent condensation reaction without further purification. HRMS (ESI) (C$_{15}$H$_{14}$NO$_3$S$^-$): calculated 288.0700. found 288.0698, Δ=-0.2 mmu.

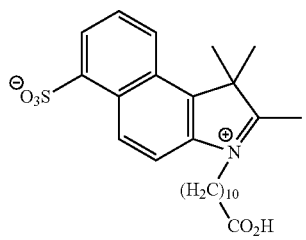

3-(10-carboxyldecyl)-1,1,2-trimethyl-1H-sulfobenzo[e]indole (5c)

3-(10-Carboxydecyl)-1,1,2-trimethyl-1H-benzo[e]indolenium bromide (2f, 300 mg, 0.632 mmol), nitrobenzene (5.0 mL) and fuming sulfuric acid (0.08 mL, 0.63 mmol, SO$_3$ content 65%) were reacted (3 d reaction time) and worked up analogously to 1,1,2-trimethyl-1H-sulfobenzo[e]indole (4). Yield: 300 mg (85%) black viscous oil, which was used for the subsequent condensation reaction without further purification. $^1$H NMR (200 MHz, CD$_3$OD): δ=8.41-8.01 (m, 4H, H$_{aromatic}$), 7.87-7.66 (m, 1H, H$_{aromatic}$), 4.63 (t, 2H, NCH$_2$, $^3$J=7.3 Hz), 3.35 (s, 3H, CH$_3$), 2.28 (t, 2H, CH$_2$CO$_2$CH$_3$, $^3$J=7.3 Hz), 2.69-1.93 (m, 2H, CH$_2$), 1.82 (s, 6H, 2×CH$_3$), 1.64-1.30 ppm (m, 14H, 7×CH$_2$). HRMS (ESI) (C$_{26}$H$_{34}$NO$_5$S$^-$): calculated 472.2169. found 472.2159, Δ=-1 mmu.

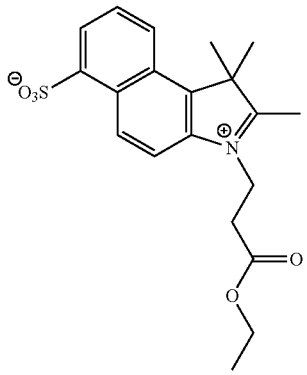

3-(2-ethoxycarbonylethyl)-1,1,2-trimethyl-1H-sulfobenzo[e]indole (5e)

3-(2-Ethoxycarbonylethyl)-1,1,2-trimethyl-1H-benzo[e]indolenium bromide (300 mg, 0.768 mmol), nitrobenzene (5.0 mL) and fuming sulfuric acid (0.10 mL, 0.77 mmol, SO$_3$ content 65%) were reacted and worked up analogously to 5c. Yield: 250 mg (69%) black viscous oil, which was used for the subsequent condensation reaction without further purification. $^1$H NMR (200 MHz, CD$_3$OD): δ=8.37-8.03 (m, 4H, H$_{aromatic}$), 7.84-7.66 (m, 1H, H$_{aromatic}$), 4.96-4.87 (m, 2H, NCH$_2$), 4.22-4.20 (m, 2H, OCH$_2$CH$_3$), 3.32-3.13 (m, 2H, CO$_2$CH$_2$CH$_3$), 2.95-2.85 (m, 3H, OCH$_2$CH$_3$), 1.82 ppm (s, 6H, 2×CH$_3$). The 2-methyl protons exchange with the solvent, and therefore do not appear in the NMR spectrum.

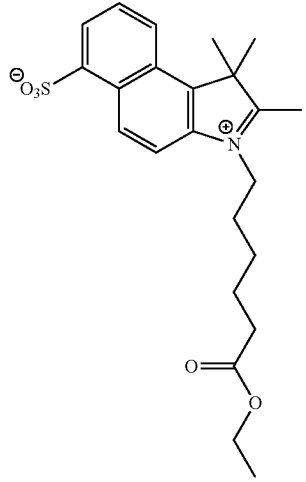

5g 3-(5-ethoxycarbonylpentyl)-1,1,2-trimethyl-1H-sulfobenzo[e]indole (5g)

3-(5-Ethoxycarbonylpentyl)-1,1,2-trimethyl-1H-benzo[e]indolenium bromide (230 mg, 0.532 mmol) and nitrobenzene (5.0 mL) and fuming sulfuric acid (0.06 mL, 0.53 mmol, SO$_3$ content 65%) were reacted and worked up analogously to 5c. Yield: 111 mg (41%) black viscous oil, which was used for the subsequent condensation reaction without further purification. $^1$H NMR (200 MHz, CD$_3$OD): δ=8.39-8.29 (m, 2H, H$_{aromatic}$), 8.18-8.01 (m, 2H, H$_{aromatic}$), 7.87-7.74 (m, 1H, H$_{aromatic}$), 4.64 (t, 2H, NCH$_2$, $^3$J=7.6 Hz), 4.20-4.17 (m, 2H, OCH$_2$CH$_3$), 2.95-2.85 (m, 3H, OCH$_2$CH$_3$), 2.37 (t, 2H, CH$_2$CO$_2$CH$_2$CH$_3$, $^3$J=6.9 Hz), 2.10-1.95 (m, 2H, CH$_2$), 1.81 (s, 6H, 2×CH$_3$), 1.74-1.50 ppm (m, 4H, 2×CH$_2$). The methyl protons in the 2-position exchange with the solvent, and therefore do not appear in the NMR spectrum. HRMS (ESI) (C$_{23}$H$_{30}$NO$_5$S$^+$): calculated 432.1839. found 432.1484, Δ=35.5 mmu.

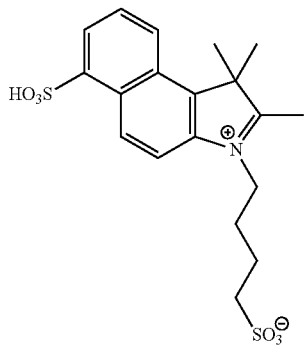

5a 3-(4-Sulfobutyl)-1,1,2-trimethyl-1H-sulfobenzo[e]indole (5a)

3-(4-Sulfobutyl)-1,1,2-trimethyl-1H-benzo[e]indole (300 mg, 0.868 mmol), nitrobenzene (5.0 mL) and fuming sulfuric acid (0.11 mL, 0.87 mmol, SO$_3$ content 65%) were reacted (2 d stirring at room temperature) and worked up analogously to 1,1,2-trimethyl-1H-sulfobenzo[e]indole (4). Yield: 200 mg (46%) black viscous oil, which was used for the subsequent condensation reaction without further purification. HRMS (ESI) (C$_{19}$H$_{24}$NO$_6$S$_2^+$): calculated 426.1040. found 426.1039, Δ=−0.1 mmu.

Synthesis of Carbocyanine Dyes

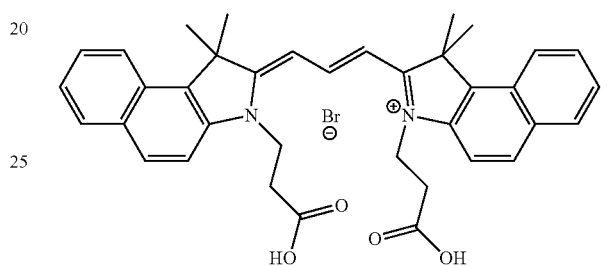

3a 3,3'-Di-(2-carboxyethyl)-1,1,1',1'-tetramethyl-1H-dibenzo[e]indocarbocyanine bromide (3a)

3-(2-Carboxyethyl)-1,1,2-trimethyl-1H-benzo[e]indolenium bromide (2a, 540 mg, 1.50 mmol) was dissolved in pyridine (2.00 mL) under an argon atmosphere, heated to 116° C., slowly combined dropwise with orthoformic acid triethyl ester (0.250 mL, 3.00 mmol) (blue-violet color), heated for 2 h under reflux, combined with diethyl ether (10.0 mL) after cooling (precipitation of the dye as a gold gleaming solid), decanted, dissolved in a small amount of ethanol and precipitated with diethyl ether several times, finally filtered off, dried under vacuum and purified via flash chromatography (RP 18, methanol/H$_2$O/glacial acetic acid 1:1:0.4 for application of the dye, methanol/H$_2$O/glacial acetic acid 2:1:0.4 for the elution of byproducts, methanol/H$_2$O/glacial acetic acid 10:1:0.4 for elution of the dye). Yield: 600 mg (70%) gold gleaming solid that forms violet, red-fluorescing solutions, melting point 199° C. R$_f$ (RP 18, methanol/H$_2$O/glacial acetic acid 10:1:0.4)=0.62. IR (ATR): ṽ=3344 (w, br), 2921 (m, br), 1723 (s), 1633 (w), 1586 (w), 1552 (s), 1519 (m), 1471 (m), 1422 (s), 1350 (m), 1279 (w), 1226 (m), 1153 (m), 1127 (m), 1011 (m), 924 (s), 876 (w), 803 (w), 787 (w), 747 (w), 729 (w), 681 (w), 651 cm$^{-1}$ (w). $^1$H NMR (200 MHz, CD$_3$OD): δ=8.27 (d, 2H, H$_{aromatic}$, $^3$J=8.7 Hz), 8.01 (t, 4H, H$_{aromatic}$, $^3$J=7.6 Hz), 7.67 (t, 5H, H$_{aromatic}$, $^3$J=6.6 Hz), 7.50 (t, 2H, H$_{aromatic}$, H$_{allyl}$, $^3$J=7.5 Hz), 6.57 (d, 2H, H$_{allyl}$, $^3$J$_E$=12.9 Hz), 4.68-4.45 (m, 4H, 2×NCH$_2$), 2.95-2.75 (m, 4H, 2×CH$_2$), 2.06 ppm (s, 12H, 4×CH$_3$). $^{13}$C NMR (100 MHz, CD$_3$OD): δ=176.1, 149.4, 139.2, 133.5, 132.2, 130.4, 129.7, 127.9, 127.4, 124.9, 121.9, 110.9, 110.9, 110.8, 65.5, 51.0, 26.6, 14.0 ppm. UV/VIS (EtOH): λ$_{max}$ (E$_{rel}$): 591 (1.0), 554 nm (0.68). UV/VIS (solid/cotton): λ$_{max}$ (E$_{rel}$): 599 (1.0), 555 nm (0.98). UV/VIS (solid/wool): λ$_{max}$ (E$_{rel}$): 559 (1.0), 595 nm (0.98). UV/VIS (solid/hair): λ$_{max}$ (E$_{rel}$): 595 (1.0), 555 nm (0.98). Fluorescence (EtOH): λ$_{max}$ (I$_{rel}$): 622 (1.0), 664 nm (0.70). Fluorescence (solid/cotton): $\lambda_{max}$ ($I_{rel}$): 667 (1.0), 643 nm (0.85). Fluorescence (solid/wool): $\lambda_{max}$ ($I_{rel}$): 635 (1.0), 667 nm (0.95). Fluorescence (solid/hair): $\lambda_{max}$ ($I_{rel}$): 624 (1.0), 665 nm (0.69). Fluorescence quantum yield (CHCl$_3$, $\lambda_{exc}$=562 nm, $E_{562/1\ cm}$=0.0146; Reference: S-13 with $\Phi$=1.00): 0.35. HRMS (ESI) ($C_{37}H_{37}N_2O_4^+$): calculated 573.2748. found 573.2747, $\Delta$=−0.1 mmu.

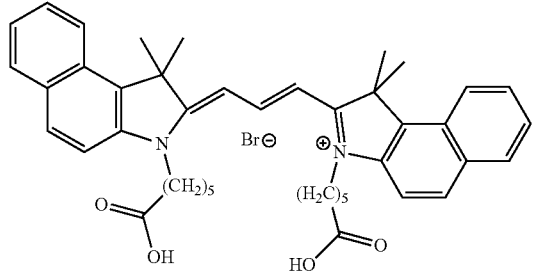

3,3'-Di-(5-carboxypentyl)-1,1,1',1'-tetramethyl-1H-dibenzo[e]indocarbocyanine bromide (3c)

3-(5-Carboxypentyl)-1,1,2-trimethyl-1H-benzo[e]indolenium bromide (2c, 150 mg, 0.37 mmol), 3-picoline (2.00 mL) and orthoformic acid triethyl ester (0.10 mL, 0.74 mmol) were reacted and worked up as described for 3,3'-di-(2-carboxyethyl)-1,1,1',1'-tetramethyl-1H-dibenzo[e]indocarbocyanine bromide (3a). Yield: 150 mg (55%) gold gleaming solid, which forms violet, red-fluorescing solutions. $R_f$ (RP 18, methanol/H$_2$O/glacial acetic acid 10:1:0.4)=0.66. IR (ATR): $\tilde{v}$=3416 (w, br), 3054 (w), 2978 (w), 2935 (w), 2859 (w), 1727 (s), 1626 (w), 1588 (w), 1547 (s), 1519 (m), 1487 (m), 1469 (w), 1424 (s), 1370 (w), 1348 (w), 1275 (w), 1227 (s), 1170 (m), 1140 (m), 1125 (m), 1031 (w), 1011 (m), 977 (m), 926 (s), 891 (w), 878 (w), 865 (w), 829 (m), 805 (m), 787 (w), 769 (w), 748 (w), 725 (w), 684 (w), 652 cm$^{-1}$ (w). $^1$H NMR (400 MHz, CD$_3$OD): $\delta$=8.78 (t, 1H, H$_{allyl}$, $^3$J=13.5 Hz), 8.30 (d, 2H, H$_{aromatic}$, $^3$J=8.5 Hz), 8.06 (d, 2H, H$_{aromatic}$, $^3$J=8.8 Hz), 8.02 (d, 2H, H$_{aromatic}$, $^3$J=8.2 Hz), 7.68 (ddd, 2H, H$_{aromatic}$, $^4$J=1.3 Hz, $^3$J=6.9 Hz, $^3$J=8.4 Hz), 7.64 (d, 2H, H$_{aromatic}$, $^3$J=8.9 Hz), 7.52 (ddd, 2H, H$_{aromatic}$, $^4$J=1.0 Hz, $^3$J=6.9 Hz, $^3$J=8.1 Hz), 6.53 (d, 2H, H$_{allyl}$, $^3$J$_E$=13.5 Hz), 4.30 (t, 4H, 2×NCH$_2$, $^3$J=7.5 Hz), 2.35 (t, 4H, 2×CH$_2$CO$_2$H, $^3$J=7.2 Hz), 2.11 (s, 12H, 4×CH$_3$), 2.04-1.86 (m, 4H, 2×CH$_2$), 1.79-1.70 (m, 4H, 2×CH$_2$), 1.63-1.55 ppm (m, 4H, 2×CH$_2$). $^{13}$C NMR (100 MHz, CD$_3$OD): $\delta$=175.9, 149.3, 139.4, 133.5, 132.2, 130.5, 129.7, 127.9, 127.4, 124.9, 121.9, 110.8, 101.7, 51.0, 43.9, 27.1, 26.6, 26.1, 22.8, 16.9 ppm. UV/VIS (EtOH): $\lambda_{max}$ ($E_{rel}$): 591 (1.0), 554 nm (0.68), UV/VIS (solid/cotton): $\lambda_{max}$ ($E_{rel}$): 598 (1.0), 554 nm (0.99). UV/VIS (solid-wool): $\lambda_{max}$ ($E_{rel}$): 558 (1.0), 594 nm (0.97). UV/VIS (solid/hair): $\lambda_{max}$ ($E_{rel}$): 598 (1.0), 556 nm (0.90). Fluorescence (EtOH): $\lambda_{max}$ ($I_{rel}$): 611 (1.0), 655 nm (0.50). Fluorescence (solid/cotton): $\lambda_{max}$ ($I_{rel}$): 661 (1.0), 644 nm (0.93). Fluorescence (solid/wool): $\lambda_{max}$ ($I_{rel}$): 632 (1.0), 667 nm (0.88). Fluorescence (solid/hair): $\lambda_{max}$ ($I_{rel}$): 623 (1.0), 660 nm (0.71). Fluorescence quantum yield (CHCl$_3$, $\lambda_{exc}$=559 nm, $E_{562/1\ cm}$=0.0126; Reference: S-13 with $\Phi$=1.00): 0.50. HRMS (ESI) ($C_{43}H_{49}N_2O_4^+$): calculated 657.3687. found 657.3691, $\Delta$=0.4 mmu.

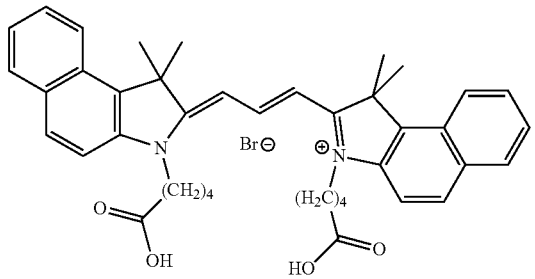

3,3'-Di-(4-carboxybutyl)-1,1,1',1'-tetramethyl-1H-dibenzo[e]indocarbocyanine bromide (3b)

3-(4-Carboxybutyl)-1,1,2-trimethyl-1H-benzo[e]indolenium bromide (2b, 140 mg, 0.36 mmol), 3-picoline (1.00 mL) and orthoformic acid triethyl ester (0.12 mL, 0.72 mmol) were reacted and worked up as described for 3,3'-di-(2-carboxyethyl)-1,1,1',1'-tetramethyl-1H-dibenzo[e]indocarbocyanine bromide (3a). Yield: 100 mg (39%) gold gleaming solid, which forms violet, red-fluorescing solutions. $R_f$ (RP 18, methanol/H$_2$O/glacial acetic acid 10:1:0.4)=0.43. IR (ATR): $\tilde{v}$=2922 (s), 2348 (m), 2213 (w), 1707 (m), 1555 (s), 1519 (s), 1479 (m), 1427 8s), 1360 (m), 1226 (m), 1154 (m), 1014 (m), 936 (m), 805 8w), 746 cm$^{-1}$ (w). $^1$H NMR (400 MHz, CD$_3$OD): $\delta$=8.28 (d, 2H, H$_{aromatic}$, $^3$J=8.5 Hz), 8.03 (dd, 5H, H$_{aromatic}$, H$_{allyl}$, $^3$J=8.5 Hz, $^3$J$_E$=12.3 Hz), 7.70-7.64 (m, 4H, H$_{aromatic}$), 7.55-7.48 (m, 2H, H$_{aromatic}$), 6.55 (d, 2H, H$_{allyl}$, $^3$J$_E$=13.0 Hz), 4.39-4.28 (m, 4H, 2×NCH$_2$), 2.49-2.35 (m, 4H, 2×CH$_2$), 2.09 (s, 12H, 4×CH$_3$), 2.00-1.91 (m, 4H, 2×CH$_2$) 1.90-1.80 ppm (m, 4H, 2×CH$_2$). $^{13}$C NMR (100 MHz, CD$_3$OD): $\delta$=175.9, 149.3, 139.4, 133.5, 132.2, 130.5, 129.7, 127.9, 127.4, 124.8, 121.9, 110.8, 101.9, 101.9, 50.9, 43.8, 26.6 ppm. UV/VIS (EtOH): $\lambda_{max}$ ($E_{rel}$): 591 (100), 552 nm (69). UV/VIS (solid/cotton): $\lambda_{max}$ ($E_{rel}$): 598 (1.0), 559 nm (0.98). UV/VIS (solid/wool): $\lambda_{max}$ ($E_{rel}$): 558 (1.0), 591 nm (0.95). UV/VIS (solid/hair): $\lambda_{max}$ ($E_{rel}$): 598 (1.0), 560 nm (0.81). Fluorescence (EtOH): $\lambda_{max}$ ($I_{rel}$): 608 (1.0), 652 nm (0.30). Fluorescence (solid/cotton): $\lambda_{max}$ ($I_{rel}$): 667 (1.0), 628 nm (0.66). Fluorescence (solid/wool): $\lambda_{max}$ ($I_{rel}$): 635 (1.0), 668 nm (0.97). Fluorescence (solid/hair): $\lambda_{max}$ ($I_{rel}$): 624 (1.0), 665 nm (0.68). Fluorescence quantum yield (CHCl$_3$, $\lambda_{exc}$=559 nm, $E_{559/1\ cm}$=0.0120, Reference: S-13 with $\Phi$=1.00): 0.49. HRMS (ESI) ($C_{41}H_{45}N_2O_4$) calculated 629.3374. found 629.3380, $\Delta$=0.6 mmu.

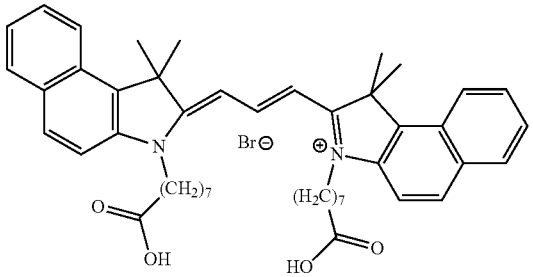

3,3'-Di-(7-carboxyheptyl)-1,1,1',1'-tetramethyl-1H-dibenzo[e]indocarbocyanine bromide (3d)

3-(7-Carboxyheptyl)-1,1,2-trimethyl-1H-benzo[e]indolemum bromide (2d, 150 mg, 0.35 mmol), 3-picoline (1.00 mL) and orthoformic acid triethyl ester (0.12 mL, 0.70 mmol) were reacted and worked up as described for 3,3'-di-(2-carboxyethyl)-1,1,1',1'-tetramethyl-1H-dibenzo[e]indocarbocyanine bromide (3a). Yield: 80.0 mg (54%) gold gleaming solid, which forms violet, red-fluorescing solutions. IR (ATR): $\tilde{v}$=2927 (s), 2348 (w), 2233 (w), 1720 (s, br), 1552 (s), 1519 (m), 1479 (w), 1422 (s), 1351 (m), 1225 (m), 1141 (m), 1011 (m), 931 (m), 806 cm$^{-1}$ (w). $^1$H NMR (400 MHz, CD$_3$OD): δ=8.78 (t, 1H, H$_{allyl}$, $^3$J$_E$=13.5 Hz), 8.30 (d, 2H, H$_{aromatic}$, $^3$J=8.3 Hz), 8.05 (t, 4H, H$_{aromatic}$, $^3$J=7.8 Hz), 7.73-7.61 (m, 4H, H$_{aromatic}$), 7.57-7.49 (m, 2H, H$_{aromatic}$), 6.53 (d, 2H, H$_{allyl}$, $^3$J$_E$=13.3 Hz), 4.29 (t, 4H, 2×NCH$_2$, $^3$J=7.7 Hz), 2.29 (t, 4H, 2×CH$_2$CO$_2$H, $^3$J=7.3 Hz), 2.11 (s, 12H, 4×CH$_3$), 1.99-1.84 (m, 4H, 2×CH$_2$), 1.63-1.40 ppm (m, 16H, 8×CH$_2$). $^{13}$C NMR (100 MHz, CD$_3$OD): δ=175.9, 133.5, 132.2, 130.5, 129.7, 127.9, 127.4, 125.2, 124.9, 121.9, 112.4, 110.7, 101.7, 57.0, 51.0, 26.6, 16.9 ppm. UV/VIS (EtOH): λ$_{max}$ (E$_{rel}$): 591 (1.0), 554 nm (0.70). UV/VIS (solid/cotton): λ$_{max}$ (E$_{rel}$): 599 (1.0), 554 nm (0.99). UV/VIS (solid/wool): λ$_{max}$ (E$_{rel}$): 558 (1.0), 595 nm (0.97). UV/VIS (solid/hair): λ$_{max}$ (E$_{rel}$): 599 (1.0), 555 nm (0.92). Fluorescence (EtOH): λ$_{max}$ (I$_{rel}$): 602 (1.0), 661 nm (0.25). Fluorescence (solid/cotton): λ$_{max}$ (I$_{rel}$): 669 (1.0), 646 nm (0.94). Fluorescence (solid/wool): λ$_{max}$ (I$_{rel}$): 632 (1.0), 668 nm (0.89). Fluorescence (solid/hair): λ$_{max}$ (I$_{rel}$): 635 (1.0), 666 nm (0.86). Fluorescence quantum yield (CHCl$_3$, λ$_{exc}$=558 nm, E$_{562/1}$ cm=0.0161, Reference: S-13 with Φ=1.00): 0.43. HRMS (ESI) (C$_{47}$H$_{97}$N$_2$O$_4^+$): calculated 713.4313. found 713.4324, Δ=1.1 mmu.

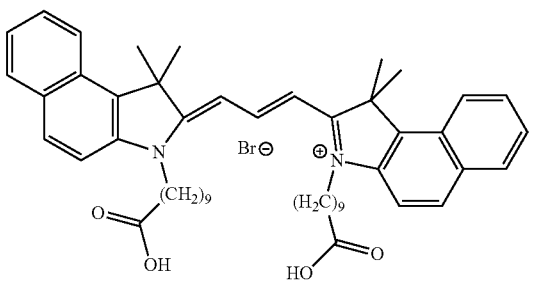

3,3'-Di-(9-carboxynonyl)-1,1,1',1'-tetramethyl-1H-dibenzo[e]indocarbocyanine bromide (3e)

3-(9-Carboxynonyl)-,1,1,2-trimethyl-1H-benzo[e]indolenium bromide (2e, 100 mg, 0.21 mmol), 3-picoline (1.00 mL) and orthoformic acid triethyl ester (0.07 mL, 0.43 mmol) were reacted and worked up as described for 3,3'-di-(2-carboxyethyl)-1,1,1',1'-tetramethyl-1H-dibenzo[e]indocarbocyanine bromide (3a). Yield: 41.0 mg (23%) gold gleaming solid, which forms violet, red-fluorescing solutions. R$_f$ (RP 18, methanol/H$_2$O/glacial acetic acid 10:1:0.4)=0.4. IR (ATR): $\tilde{v}$=3381 (w), 3056 (w), 2923 (s), 2852 (s), 2350 (w), 2287 (w), 1711 (m), 1626 (w), 1588 (w), 1554 (s), 1520 (m), 1479 (m), 1423 (s), 1357 (m), 1277 (w), 1224 (m), 1168 (m), 1142 (m), 1127 (m), 1012 (m), 971 (w), 930 (s), 898 (w), 867 (w), 806 (m), 786 (w), 746 (w), 726 (w), 685 (w), 676 (w), 652 cm$^{-1}$ (m). $^1$H NMR (400 MHz, CD$_3$OD): δ=8.78 (t, 1H, H$_{allyl}$, $^3$J$_E$=13.2 Hz), 8.29 (d, 2H, H$_{aromatic}$, $^3$J=8.6 Hz), 8.06 (d, 2H, H$_{aromatic}$, $^3$J=8.8 Hz), 8.03 (d, 2H, H$_{aromatic}$, $^3$J=8.1 Hz), 7.72-7.62 (m, 4H, H$_{aromatic}$) 7.55-7.50 (m, 2H, H$_{aromatic}$), 6.51 (d, 2H, H$_{allyl}$, $^3$J$_E$=13.5 Hz), 4.29 (t, 4H, 2×NCH$_2$, $^3$J=7.5 Hz), 2.20 (t, 4H, 2×CH$_2$CO$_2$H, $^3$J=7.2 Hz), 2.11 (s, 12H, 4×CH$_3$), 1.96-1.88 (m, 8H, 4×CH$_2$), 1.60-1.50 (m, 8H, 4×CH$_2$), 1.49-1.40 (m, 4H, 2×CH$_2$), 1.33-1.30 ppm (m, 8H, 4×CH$_2$). $^{13}$C NMR (100 MHz, CD$_3$OD): δ=175.9, 149.3, 139.4, 133.5, 132.2, 130.5, 129.8, 127.9, 127.5, 124.9, 121.9, 110.8, 101.6, 51.0, 44.0, 28.9, 28.9, 28.8, 27.4, 26.6, 26.3, 25.2, 16.9 ppm. UV/VIS (EtOH): λ$_{max}$ (E$_{rel}$): 594 (1.0), 555 nm (0.65). UV/VIS (solid/cotton): λ$_{max}$ (E$_{rel}$): 569 (1.0), 557 nm (0.99). UV/VIS (solid/wool): λ$_{max}$ (E$_{rel}$): 565 (1.0), 597 nm (0.90). UV/VIS (solid/hair): λ$_{max}$ (E$_{rel}$) 603 (1.0), 557 nm (0.95). Fluorescence (EtOH): λ$_{max}$ (I$_{rel}$): 604 (1.0), 651 nm (0.25). Fluorescence (solid/cotton): λ$_{max}$ (I$_{rel}$): 669 (1.0), 645 nm (0.94). Fluorescence (solid/wool): λ$_{max}$ (I$_{rel}$): 632 (1.0), 668 nm (0.89). Fluorescence (solid/hair): λ$_{max}$ (I$_{rel}$): 635 (1.0), 666 nm (0.87). Fluorescence quantum yield (CHCl$_3$, λ$_{exc}$=557 nm, E$_{562/1}$ $_{cm}$=0.0180, Reference: S-13 with Φ=1.00): 0.59. HRMS (ESI) (C$_{51}$H$_{65}$N$_2$O$_4^+$): calculated 769.4939. found 769.4941, Δ=0.2 mmu.

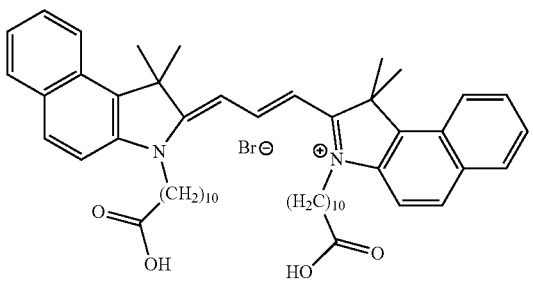

3,3'-Di-(10-carboxydecyl)-1,1,1',1'-tetramethyl-1H-dibenzo[e]indocarbocyanine bromide (3f)

3-(10-Carboxydecyl)-1,1,2-trimethyl-1H-benzo[e]indolenium bromide (2f, 117 mg, 0.25 mmol), pyridine (2.5 mL) and orthoformic acid triethyl ester (0.08 mL, 0.5 mmol) were reacted (120° C.) and worked up as for 3,3'-di-(2-carboxyethyl)-1,1,1',1'-tetramethyl-1H-dibenzo[e]indocarbocyanine bromide (3a). Yield: 118 mg (54%) gold gleaming solid, which forms violet, red-fluorescing solutions. IR (ATR): $\tilde{v}$=3381 (w), 3056 (w), 2923 (s), 2852 (s), 2350 (w), 2287 (w), 1711 (m), 1626 (w), 1588 (w), 1554 (s), 1520 (m), 1479 (m), 1423 (s), 1357 (m), 1277 (w), 1224 (m), 1012 (m), 971 (w), 930 (s), 898 (w), 867 (w), 806 (m), 786 (w), 746 (w), 726 (w), 685 (w), 676 (w), 652 cm$^{-1}$ (m). $^1$H NMR (400 MHz, CD$_3$OD): δ=8.77 (t, 1H, CH$_{allyl}$, $^3$J$_E$=13.4 Hz), 8.29 (d, 2H, CH$_{aromatic}$, $^3J$=8.6 Hz), 8.05 (d, 2H, CH$_{aromatic}$, $^3J$=8.7 Hz), 8.02 (d, 2H, CH$_{aromatic}$, $^3J$=8.4 Hz), 7.70-7.62 (m, 4H, CH$_{aromatic}$), 7.52 (t, 2H, CH$_{aromatic}$, $^3J$=7.5 Hz), 6.50 (d, 2H, CH$_{allyl}$, $^3J_E$=13.6 Hz), 4.28 (t, 4H, 2×NCH$_2$, $^3J$=7.1 Hz), 2.30-2.13 (m, 4H, 2×CH$_2$CO$_2$H), 2.10 (s, 12H, 4×CH$_3$), 1.98-1.88 (m, 4H, 2×CH$_2$), 1.58-1.50 (m, 8H, 4×CH$_2$), 1.35-1.22 ppm (m, 20H, 10×CH$_2$). $^{13}$C NMR (100 MHz, CD$_3$OD): δ=175.9, 149.2, 139.4, 133.5, 132.2, 131.3, 130.5, 129.7, 127.9, 127.5, 124.9, 121.9, 114.7, 110.8, 101.6, 51.0, 44.0, 29.0, 29.0, 28.9, 27.4 26.6, 26.3, 22.8 ppm. UV/VIS (EtOH): λ$_{max}$ (E$_{rel}$): 590 (1.0), 553 nm (0.70). UV/VIS (solid/cotton): λ$_{max}$ (E$_{rel}$): 597 (1.0), 555 nm (0.99). UV/VIS (solid/wool): λ$_{max}$ (E$_{rel}$): 557 (1.0), 596 nm (0.96). UV/VIS (solid/hair): λ$_{max}$ (E$_{rel}$): 601 (1.0), 556 nm (0.97). Fluorescence (EtOH): λ$_{max}$ (I$_{rel}$): 610 (1.0), 656 nm (0.54). Fluorescence (solid/cotton): λ$_{max}$ (I$_{rel}$): 670 (1.0), 641 nm (0.83). Fluorescence (solid/wool): λ$_{max}$ (I$_{rel}$): 667 (1.0), 641 nm (0.98). Fluorescence (solid/hair): λ$_{max}$ (I$_{rel}$): 640 (1.0), 667 nm (0.93). Fluorescence quantum yield (CHCl$_3$, λ$_{exc}$=557 nm, E$_{562/1\ cm}$=0.0131, Reference: S-13 with Φ1.00): 0.33. HRMS (ESI) (C$_{53}$H$_{69}$N$_2$O$_4^+$): calculated 797.5252. found 797.5267, Δ=1.5 mmu.

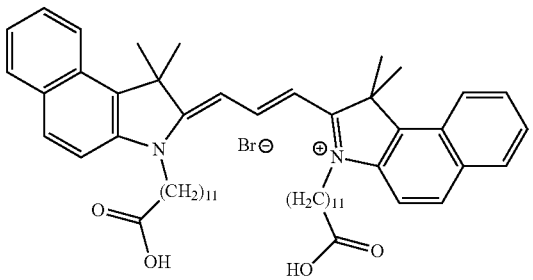

3,3'-Di-(11-carboxyundecyl)-1,1,1',1'-tetramethyl-1H-dibenzo[e]indocarbocyanine bromide (3g)

3-(11-Carboxyundecyl)-1,1,2-trimethyl-1H-benzo[e]indolenium bromide (2g, 340 mg, 7.00 μmol), 3-picoline (1.00 mL) and orthoformic acid triethyl ester (0.020 mg, 0.020 mL, 0.014 mmol) were reacted and worked up as for 3,3'-di-(2-carboxyethyl)-1,1,1',1'-tetramethyl-1H-dibenzo[e]indocarbocyanine bromide (3a) (chromatography with aqueous 2 N HCl instead of glacial acetic acid). Yield: 12.0 mg (19%) gold gleaming solid, which forms violet, red-fluorescing solutions. R$_f$ (RP 18, methanol/H$_2$O/HCl 10:1:0.4)=0.8. IR (ATR): $\tilde{v}$=3350 (w), 2922 (s), 2851 (m), 1710 (m), 1625 (w), 1587 (w), 1553 (s), 1519 (m), 1479 (m), 1422 (s), 1356 (m), 1278 (w), 1259 (w), 1224 (m), 1169 (m), 1141 (w), 1127 (m), 1012 (m), 973 (w), 931 (s), 896 (w), 806 (m), 786 (w), 746 (w), 726 (w), 685 (w), 675 cm$^{-1}$ (w). $^1$H NMR (400 MHz, CD$_3$OD): δ=8.78 (t, 2H, H$_{allyl}$, $^3J_E$=13.5 Hz), 8.29 (d, 2H, H$_{aromatic}$, $^3J$=8.5 Hz), 8.06 (d, 2H, H$_{aromatic}$, $^3J$=8.8 Hz), 8.03 (d, 2H, H$_{aromatic}$, $^3J$=8.2 Hz), 7.68 (ddd, 3H, H$_{aromatic}$, $^4J$=1.2 Hz, $^3J$=6.9 Hz, $^3J$=8.4 Hz), 7.64 (d, 2H, H$_{aromatic}$, $^3J$=8.9 Hz), 7.53 (ddd, 2H, H$_{aromatic}$, $^4J$=0.9 Hz, $^3J$=6.9 Hz, $^3J$=8.0 Hz), 6.50 (d, 2H, H$_{allyl}$, $^3J_E$=13.5 Hz), 4.29 (t, 4H, 2×NCH$_2$, $^3J$=7.4 Hz), 2.18 (t, 4H, 2×CH$_2$CO$_2$H, $^3J$=7.4 Hz), 2.11 (s, 12H, 4×CH$_3$), 1.96-1.88 (m, 4H, 2×CH$_2$), 1.57-1.49 (m, 8H, 4×CH$_2$), 1.47-1.40 (m, 4H, 2×CH$_2$), 1.36-1.28 ppm (m, 20H, 10×CH$_2$). $^{13}$C NMR (100 MHz, CD$_3$OD): δ=178.6, 175.9, 149.2, 139.4, 133.5, 132.2, 130.5, 129.7, 127.9, 127.5, 124.9, 121.9, 110.8, 101.7, 56.9, 51.0, 44.0, 29.1, 29.0, 29.0, 29.0, 28.9, 27.3, 26.6, 26.3, 25.4, 16.9 ppm. UV/VIS (EtOH): λ$_{max}$ (E$_{rel}$): 590 (1.0), 553 nm (0.70). UV/VIS (solid/cotton): λ$_{max}$ (E$_{rel}$): 600 (1.0), 555 nm (0.97). UV/VIS (solid/wool): λ$_{max}$ (E$_{rel}$): 603 (1.0), 556 nm (0.95). UV/VIS (solid/hair): λ$_{max}$ (E$_{rel}$): 607 (1.0), 556 nm (0.93). Fluorescence (EtOH): λ$_{max}$ (I$_{rel}$): 604 (1.0), 656 nm (0.20). Fluorescence (solid/cotton): λ$_{max}$ (I$_{rel}$): 667 (1.0), 643 nm (0.94). Fluorescence (solid/wool): λ$_{max}$ (I$_{rel}$): 638 (1.0), 667 nm (0.93). Fluorescence (solid/hair): λ$_{max}$ (I$_{rel}$): 634 (1.0), 668 nm (0.88). Fluorescence quantum yield (CHCl$_3$, λ$_{exc}$=560 nm, E$_{562/1\ cm}$=0.0127, Reference: S-13 with Φ=1.00): 0.35. HRMS (ESI) (C$_{55}$H$_{73}$N$_2$O$_4^+$): calculated 825.5565. found 825.5567, Δ=0.2 mmu.

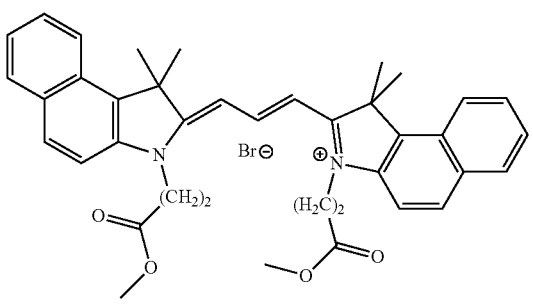

3,3'-Di-(2-methoxycarbonylethyl)-1,1,1',1'-tetramethyl-1H-dibenzo[e]indocarbocyanine bromide (3h)

3-(2-Methoxycarbonylethyl)-1,1,2-trimethyl-1H-benzo[e]indolenium bromide (2h, 300 mg, 0.797 mmol), 3-picoline (2.0 mL) and orthoformic acid triethyl ester (0.26 mL, 1.60 mmol) were reacted (100° C.) and worked up without chromatography as described for 3,3'-di-(2-carboxyethyl)-1,1,1',1'-tetramethyl-1H-dibenzo[e]indocarbocyanine bromide (3a). Yield: 290 mg (53%) gold gleaming solid, which forms violet, red-fluorescing solutions. IR (ATR): $\tilde{v}$=2925 (s), 2856 (w), 2541 (w), 1960 (w), 1722 (s), 1625 (m), 1567 (m), 1555 (s), 1519 (m), 1476 (m), 1422 (s), 1352 (m), 1278 (m), 1232 (w), 1155 (m), 1126 (w), 1011 (m), 924 (m, br), 875 (w), 804 (m), 786 (w), 804 (m), 786 (w), 744 cm$^{-1}$ (m). $^1$H NMR (200 MHz, CD$_3$OD): δ=8.42 (t, 2H, H$_{allyl}$, $^3J_E$=13.4 Hz), 8.11 (d, 4H, H$_{aromatic}$, H$_{allyl}$, $^3J$=8.0 Hz), 7.96 (d, 2H, H$_{aromatic}$, $^3J$=8.5 Hz), 7.40-7.30 (m, 4H, H$_{aromatic}$), 7.16 (t, 2H, H$_{aromatic}$, $^3J$=7.5 Hz), 6.38 (d, 2H, H$_{allyl}$, $^3J_E$=13.4 Hz), 4.35-4.30 (m, 4H, 2×NCH$_2$), 3.31 (s, 6H, 2×OCH$_3$), 2.68 (t, 4H, 2×CH$_2$CO$_2$CH$_3$, $^3J$=6.6 Hz), 1.71 ppm (s, 12H, 4×CH$_3$). $^{13}$C NMR (100 MHz, CD$_3$OD): δ=177.7, 172.5, 151.1, 140.5, 134.9, 133.7, 131.9, 131.3, 131.2, 129.3, 129.0, 126.5, 123.5, 112.3, 52.5, 41.5, 33.0, 28.2, 24.2 ppm. UV/VIS (EtOH): λ$_{max}$ (E$_{rel}$): 592 (1.0), 553 nm (0.67). UV/VIS (solid/cotton): λ$_{max}$ (E$_{rel}$): 600 (1.0), 554 nm (0.99). UV/VIS (solid/wool): λ$_{max}$ (E$_{rel}$): 597 (1.0), 560 nm (0.97). UV/VIS (solid/hair): λ$_{max}$ (E$_{rel}$): 597 (1.0), 558 nm (0.98). Fluorescence (EtOH): λ$_{max}$ (I$_{rel}$): 609 (1.0), 656 nm (0.53). Fluorescence quantum yield (CHCl$_3$, λ$_{exc}$=562 nm, E$_{562/1\ cm}$=0.0178, Reference: S-13 with Φ=1.00): 0.24. HRMS (ESI) (C$_{39}$H$_{41}$N$_2$O$_4^+$): calculated 601.3061. found 601.3044. Δ=−1.7 mmu.

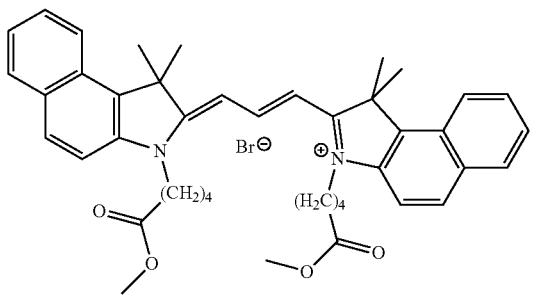
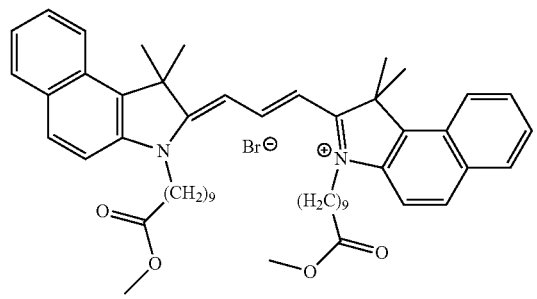

3,3'-Di-(4-methoxycarbonylbutyl)-1,1,1',1'-tetramethyl-1H-dibenzo[e]indocarbocyanine bromide (3i)

3-(4-Methoxycarbonylbutyl)-1,1,2-trimethyl-1H-benzo[e]indolenium bromide (2i, 253 mg, 0.626 mmol), 3-picoline (2.2 mL) and orthoformic acid triethyl ester (0.2 mL, 1.3 mmol) were reacted (100° C.) and worked up (chromatography with aqueous 2 N HCl instead of glacial acetic acid) as described for 3,3'-di-(2-carboxyethyl)-1,1,1'1,'-tetramethyl-1H-dibenzo[e]indocarbocyanine bromide (3a). Yield: 50 mg (11%) gold gleaming solid, which forms violet, red-fluorescing solutions. IR (ATR): $\tilde{v}$=3354 (w, br), 3140 (w), 3030 (w), 2960 (w), 2924 (s), 2855 (w), 2167 (w), 1705 (m, br), 1623 (w), 1587 (w), 1554 (s), 1520 (m), 1479 (m), 1425 (s), 1353 (m), 1278 (w), 1260 (w), 1226 (m), 1153 (s), 1128 (m), 1066 (w), 1013 (m), 982 (w), 937 (m), 917 (w), 895 (w), 865 (w), 807 (m), 786 (w), 746 (w), 727 cm$^{-1}$ (w). $^1$H NMR (400 MHz, CD$_3$OD): δ=8.79-8.76 (m, 1H, H$_{aromatic}$), 8.30 (d, 2H, H$_{aromatic}$, $^3J$=8.4 Hz), 8.04 (dd, 4H, H$_{aromatic}$, H$_{allyl}$, $^3J$=8.5 Hz, $^3J_E$=14.9 Hz), 7.71-7.64 (m, 4H, H$_{aromatic}$), 7.55-7.51 (m, 2H, H$_{aromatic}$), 6.54 (d, 2H, H$_{allyl}$, $^3J_E$=13.5 Hz), 4.31 (t, 4H, 2×NCH$_2$, $^3J$=7.3 Hz), 2.48 (t, 4H, 2×CH$_2$CO$_2$H, CH$_3$, $^3J$=7.0 Hz), 2.10 (s, 12H, 4×CH$_3$), 1.99-1.92 (m, 4H, 2×CH$_2$), 1.87-1.80 ppm (m, 4H, 2×CH$_2$). $^{13}$C NMR (100 MHz, CD$_3$OD): δ=175.9, 174.0, 149.3, 149.2, 139.4, 133.5, 132.2, 130.5, 129.7, 127.5, 125.0, 121.9, 110.8, 101.8, 51.0, 43.6, 32.7, 26.6, 21.7 ppm. UV/VIS (EtOH); λ$_{max}$ (E$_{rel}$): 592 (1.0), 555 nm (0.72). UV/VIS (solid/cotton): λ$_{max}$ (E$_{rel}$): 602 (1.0), 555 nm (0.98). UV/VIS (solid/wool): λ$_{max}$ (E$_{rel}$): 557 (1.0), 556 nm (0.98). UV/VIS (solid/hair): λ$_{max}$ (E$_{rel}$): 602 (1.0), 558 (0.92), 631 nm (0.89). Fluorescence (EtOH): λ$_{max}$ (I$_{rel}$): 608 (1.0), 658 nm (0.49). Fluorescence (solid/cotton): λ$_{max}$ (I$_{rel}$): 668 (1.0), 630 nm (0.55). Fluorescence (solid/wool): λ$_{max}$ (I$_{rel}$): 667 (1.0), 635 nm (0.98). Fluorescence (solid/hair): λ$_{max}$ (I$_{rel}$): 667 (1.0), 623 nm (0.66). Fluorescence quantum yield (CHCl$_3$, λ$_{exc}$558 nm, E$_{558/1\ cm}$=0.0114, Reference: S-13 with Φ=1.00): 0.40. HRMS (ESI) (C$_{43}$H$_{49}$N$_2$O$_4{}^+$): calculated 657.3687. found 657.3675, Δ=−1.2 mmu.

3,3'-Di-(9-methoxycarbonylnonyl)-1,1,1',1'-tetramethyl-1H-dibenzo[e]indocarbocyanine bromide (3j)

3-(9-Methoxycarbonylnonyl)-1,1,2-trimethyl-1H-benzo[e]indolenium bromide (2j, 300 mg, 0.633 mmol), 3-picoline (2.0 mL) and orthoformic acid triethyl ester (0.20 mL, 1.26 mmol) were reacted (100° C.) and worked up without chromatography as described for 3,3'-di-(2-carboxyethyl)-1,1,1'1'-tetramethyl-1H-dibenzo[e]indocarbocyanine bromide (3a). Yield: 113 mg (20%) gold gleaming solid, which forms violet, red-fluorescing solutions. IR (ATR): $\tilde{v}$=3413 (s, br), 3032 (m), 2971 (w), 2932 (m), 2855 (w), 2361 (s), 2339 (m), 2066 (w), 1729 (m), 1634 (s), 1591 (w), 1555 (m), 1505 (s), 1483 (w), 1429 (s), 1385 (w), 1357 (w), 1324 (w), 1246 (w), 1230 (w), 1204 (w), 1160 (s), 1096 (w), 1051 (w), 1014 (w), 981 (w), 934 (m), 893 (w), 810 (s), 751 (w), 728 (w), 685 cm$^{-1}$ (s). UV/VIS (EtOH): λ$_{max}$ (E$_{rel}$): 591 (1.0), 551 nm (0.73). UV/VIS (solid/cotton): λ$_{max}$ (E$_{rel}$): 600 (1.0), 559 nm (0.94). UV/VIS (solid/wool): λ$_{max}$ (E$_{rel}$): 599 (1.0), 559 nm (0.92). UV/VIS (solid/hair): λ$_{max}$ (E$_{rel}$): 699 (1.0), 558 nm (0.95). Fluorescence (EtOH): λ$_{max}$ (I$_{rel}$): 610 (1.0), 658 nm (0.51). Fluorescence quantum yield (CHCl$_3$, λ$_{exc}$=559 nm, E$_{559/1\ cm}$=0.0145, Reference: S-13 with Φ=1.00): 0.47. HRMS (ESI) (C$_{53}$N$_{69}$N$_2$O$_4{}^+$): calculated 797.5252. found 797.5252, Δ=0.03 mmu.

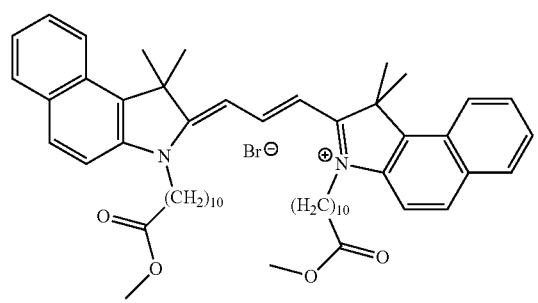

3,3'-Di-(10-methoxycarbonyldecyl)-1,1,1',1'-tetramethyl-1H-dibenzo[e]indocarbocyanine bromide (3k)

3-(10-Methoxycarbonyldecyl)-1,1,2-trimethyl-1H-benzo[e]indolenium bromide (2k, 300 mg, 0.633 mmol), pyridine (1.0 mL) and orthoformic acid triethyl ester (0.16 mL, 0.94 mmol) were reacted (100° C.) and worked up without chromatography as described for 3,3'-di-(2-carboxyethyl)-1,1,1', 1'-tetramethyl-1H-dibenzo[e]indocarbocyanine bromide (3a). Yield: 149 mg (35%) gold gleaming solid, which forms violet, red-fluorescing solutions. IR (ATR): ṽ=3403 (s, br), 3131 (w), 3055 (w), 2972 (w), 2927 (s), 2853 (m), 2361 (w), 2337 (w), 2170 (w), 1731 (s), 1633 (m), 1586 (w), 1553 (s), 1519 (m), 1484 (m), 1425 (s), 1392 (w), 1356 (w), 1277 (w), 1227 (m), 1171 (s), 1143 (w), 1128 (w), 1050 (w), 1012 (m), 975 (w), 930 (m), 897 (w), 808 (w), 780 (w), 748 (w), 726 (w), 682 cm$^{-1}$ (w). UV/VIS (EtOH): $\lambda_{max}$ ($E_{rel}$): 591 (1.0), 550 nm (0.69). UV/VIS (solid/cotton): $\lambda_{max}$ ($E_{rel}$): 603 (1.0), 559 nm (0.95). UV/VIS (solid/wool): $\lambda_{max}$ ($E_{rel}$): 596 (1.0), 557 nm (0.97). UV/VIS (solid/hair): $\lambda_{max}$ ($E_{rel}$): 600 (1.0), 557 nm (0.95). Fluorescence (EtOH): $\lambda_{max}$ ($I_{rel}$): 610 (1.0), 657 nm (0.53). Fluorescence quantum yield (CHCl$_3$, $\lambda_{exc}$=560 nm, $E_{562/1\ cm}$=0.0174, Reference: S-13 with Φ=1.00): 0.36. HRMS (ESI) ($C_{55}H_{73}N_2O_4^+$): calculated 825.5565. found 8525.5569, Δ=0.4 mmu.

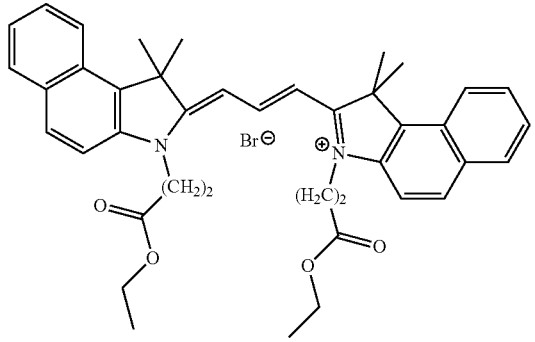

3,3'-Di-(2-ethoxycarbonylethyl)-1,1,1',1'-tetramethyl-1H-dibenzo[e]indocarbocyanine bromide (3l)

3-(2-Ethoxycarbonylethyl)-1,1,2-trimethyl-1H-benzo[e]indolenium bromide (2l, 200 mg, 0.51 mmol), 3-picoline (1.1 mL) and orthoformic acid triethyl ester (0.17 mL, 1.02 mmol) were reacted (120° C.) and worked up (chromatography with aqueous 2 N HCl instead of glacial acetic acid) as described for 3,3'-di-(2-carboxyethyl)-1,1,1',1'-tetramethyl-1H-dibenzo[e]indocarbocyanine bromide (3a). Yield: 121 mg (33%) gold gleaming solid, which forms violet, red-fluorescing solutions. IR (ATR): ṽ=3054 (w), 2973 (w), 2927 (w), 2574 (w), 2366 (w), 1723 (s), 1626 (m), 1587 (w), 1554 (s), 1520 (m), 1477 (m), 1425 (s), 1393 (w), 1353 (m), 1279 (w), 1227 (m), 1154 (m), 1128 (w), 1047 (w), 1012 (m), 987 (w), 925 (s), 877 (w), 806 (m), 786 (w), 746 (w), 728 (w), 684 cm$^{-1}$ (w). $^1$H NMR (400 MHz, CD$_3$OD): δ=8.80-8.75 (m, 1H, H$_{aromatic}$), 8.28 (d, 2H, H$_{aromatic}$, $^3J$=8.6 Hz), 8.03 (dd, 4H, H$_{aromatic}$, H$_{allyl}$, $^3J$=8.6 Hz, $^3J_E$=13.5 Hz), 7.70-7.65 (m, 4H, H$_{aromatic}$), 7.54-7.49 (m, 2H, H$_{aromatic}$), 6.54 (d, 2H, H$_{allyl}$, $^3J_E$=13.4 Hz), 4.13 (t, 4H, 2×NCH$_2$, $^3J$=6.8 Hz), 3.60 (q, 4H, 2×CH$_2$CH$_3$, $^3J$=7.0 Hz), 2.73 (t, 4H, 2×CH$_2$CO$_2$H, CH$_3$, $^3J$=6.9 Hz), 1.58 (s, 12H, 4×CH$_3$), 1.17 ppm (t, 6H, 2×CH$_2$CH$_3$, $^3J$=7.1 Hz). $^{13}$C NMR (100 MHz, CD$_3$OD): δ=178.1, 172.9, 151.4, 140.8, 135.2, 134.0, 132.2, 131.5, 129.6, 129.3, 126.8, 123.1, 112.6, 111.6, 52.8, 41.7, 37.6, 33.2, 28.4, 24.5 ppm. UV/VIS (EtOH): $\lambda_{max}$ ($E_{rel}$): 598 (1.0), 561 nm (0.69). UV/VIS (solid/cotton): $\lambda_{max}$ ($E_{rel}$): 560 (1.0), 555 nm (0.99). UV/VIS (solid/wool): $\lambda_{max}$ ($E_{rel}$): 597 (1.0), 555 nm (0.98). UV/VIS (solid/hair): $\lambda_{max}$ ($E_{rel}$): 560 (1.0), 554 nm (0.94). Fluorescence (EtOH): $\lambda_{max}$ ($I_{rel}$): 608 (1.0), 659 nm (0.54). Fluorescence (solid/cotton): $\lambda_{max}$ ($I_{rel}$): 666 (1.0), 642 nm (0.93). Fluorescence (solid/wool): $\lambda_{max}$ ($I_{rel}$): 664 (1.0), 639 nm (0.98). Fluorescence (solid/hair): $\lambda_{max}$ ($I_{rel}$): 636 (1.0), 664 nm (0.92). Fluorescence quantum yield (CHCl$_3$, $\lambda_{exc}$=561 nm, $E_{561/1\ cm}$=0.0135, Reference: S-13 with Φ=1.00): 0.33. HRMS (ESI): ($C_{41}H_{45}N_2O_4^+$): calculated 629.3374. found 629.3385, Δ=1.1 mmu.

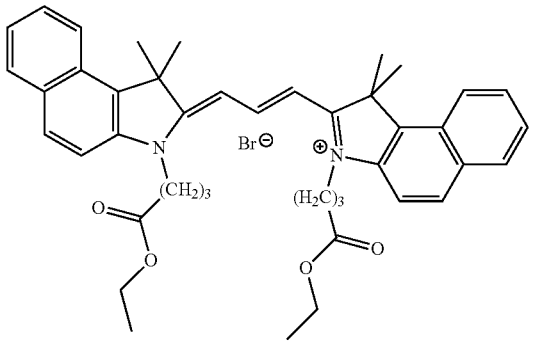

3,3'-Di-(3-ethoxycarbonylpropyl)-1,1,1',1'-tetramethyl-1H-dibenzo[e]indocarbocyanine bromide (3m)

3-(3-Ethoxycarbonylpropyl)-1,1,2-trimethyl-1H-benzo[e]indolenium bromide (2m, 250 mg, 0.620 mmol), 3-picoline (1.0 mL) and orthoformic acid triethyl ester (0.200 mL, 1.24 mmol) were reacted (100° C.) and worked up (chromatography with aqueous 2 N HCl instead of glacial acetic acid) as described for 3,3'-di-(2-carboxyethyl)-1,1,1',1'-tetramethyl-1H-dibenzo[e]indocarbocyanine bromide (3a). Yield: 215 mg (47%) gold gleaming solid, which forms violet, red-fluorescing solutions. IR (ATR): ṽ=3391 (w), 2969 (w), 2921 (m), 1726 (s), 1622 (m), 1589 (w), 1557 (s), 1520 (m), 1477 (m), 1427 (s), 1352 (m), 1227 (m), 1154 (s), 1123 (w), 1067 (w), 1014 (m), 941 (s), 899 (w), 805 (m), 791 (w), 757 (m), 728 (w), 675 (w), 652 (m), 638 cm$^{-1}$ (w). $^1$H NMR (400 MHz, CD$_3$OD): δ=8.81-8.73 (m, 1H, H$_{aromatic}$), 8.28 (d, 2H, H$_{aromatic}$, $^3J$=8.4 Hz), 8.01 (dd, 4H, H$_{aromatic}$, H$_{allyl}$, $^3J$=8.3 Hz, $^3J_E$=14.5 Hz), 7.71-7.62 (m, 4H, H$_{aromatic}$), 7.52-7.47 (m, 2H, H$_{aromatic}$), 6.54 (d, 2H, H$_{allyl}$, $^3J_E$=13.8 Hz), 4.34-4.28 (m, 4H, 2×NCH$_2$), 4.11 (q, 4H, 2×CH$_2$CH$_3$, $^3J$=7.1 Hz), 2.62-2.57 (m, 4H, 2×CH$_2$CO$_2$H, CH$_2$), 2.20-2.13 (m, 4H, 2×CH$_2$), 2.07 (s, 12H, 4×CH$_3$), 1.20 ppm (t, 6H, 2×CH$_2$CH$_3$, $^3J$=7.1 Hz). $^{13}$C NMR (100 MHz, CD$_3$OD): δ=176.1, 173.0, 149.5, 139.3, 133.5, 132.2, 130.6, 129.8, 127.9, 125.0, 121.9, 110.7, 101.8, 60.4, 51.0, 46.9, 43.2, 30.2, 26.6, 22.8, 13.1 ppm. UV/VIS (EtOH): $\lambda_{max}$ ($E_{rel}$): 598 (1.0), 559 nm (0.63). UV/VIS (solid/cotton): $\lambda_{max}$ ($E_{rel}$): 600 (1.0), 555 nm (0.99). UV/VIS (solid/wool): $\lambda_{max}$ ($E_{rel}$): 559 (1.0), 594 nm (0.98). UV/VIS (solid/hair): $\lambda_{max}$ ($E_{rel}$): 597 (1.0), 554 nm (0.96). Fluorescence (EtOH): $\lambda_{max}$ ($I_{rel}$): 610 (1.0), 657 nm (0.56). Fluorescence (solid/cotton): $\lambda_{max}$ ($I_{rel}$): 667 (1.0), 642 nm (0.88). Fluorescence (solid/wool): $\lambda_{max}$ ($I_{rel}$): 635 (1.0), 665 nm (0.97). Fluorescence (solid/hair): $\lambda_{max}$ ($I_{rel}$): 665 (1.0), 639 nm (0.97). Fluorescence quantum yield (CHCl$_3$, $\lambda_{exc}$=560 nm, $E_{562/1\ cm}$=0.0132, Reference: S-13 with Φ=1.00): 0.61. HRMS (ESI) ($C_{43}H_{49}N_2O_4^+$): calculated 657.3687. found 657.3695, Δ=0.8 mmu.

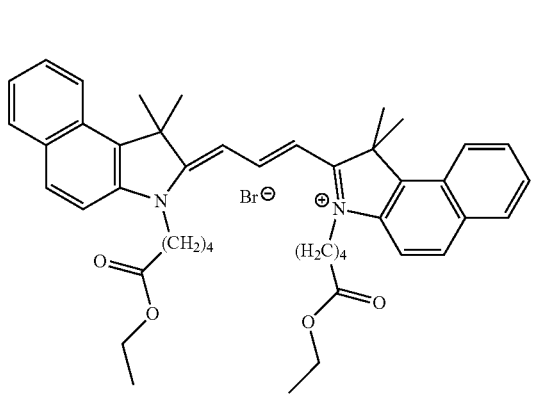

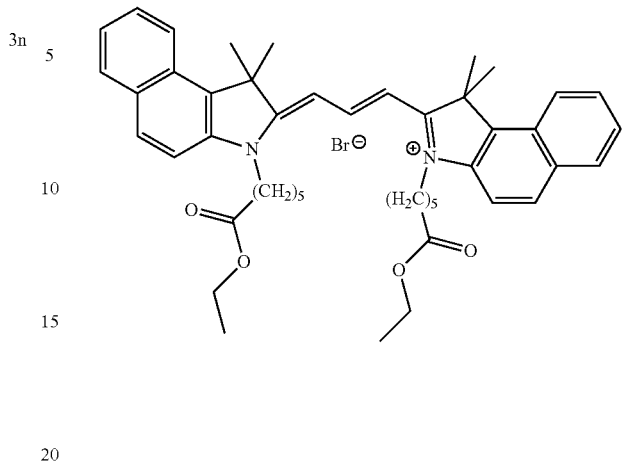

3,3'-Di-(4-ethoxycarbonylbutyl)-1,1,1',1'-tetramethyl-1H-dibenzo[e]indocarbocyanine bromide (3n)

3-(4-Ethoxycarbonylbutyl)-1,1,2-trimethyl-1H-benzo[e]indolenium bromide (2n, 250 mg, 0.6 mmol), 3-picoline (1.1 mL) and orthoformic acid triethyl ester (0.2 mL, 1.2 mmol) were reacted (100° C.) and worked up (chromatography with aqueous 2 N HCl instead of glacial acetic acid) as described for 3,3'-di-(2-carboxyethyl)-1,1,1',1'-tetramethyl-1H-dibenzo[e]indocarbocyanine bromide (3a). Yield: 105 mg (23%) gold gleaming solid, which forms violet, red-fluorescing solutions. IR (ATR): $\tilde{v}$=3420 (w), 2921 (s), 2851 (m), 1726 (s), 1622 (m), 1589 (w), 1555 (s), 1520 (s), 1477 (m), 1428 (s), 1352 (m), 1227 (m), 1154 (s), 1123 (w), 1067 (w), 1014 (m), 941 (m), 899 (w), 805 (m), 785 (w), 744 (m), 728 (w), 685 (w), 652 cm$^{-1}$ (m). $^1$H NMR (400 MHz, CD$_3$OD): $\delta$=8.76 (t, 1H, H$_{aromatic}$, $^3J$=13.1 Hz), 8.28 (d, 2H, H$_{aromatic}$, $^3J$=8.3 Hz), 8.03 (dd, 4H, H$_{aromatic}$, H$_{allyl}$, $^3J$=8.6 Hz, $^3J_E$=12.3 Hz), 7.75-7.60 (m, 4H, H$_{aromatic}$), 7.55-7.49 (m, 2H, H$_{aromatic}$), 6.51 (d, 2H, H$_{allyl}$, $^3J_E$=13.0 Hz), 4.35-4.28 (m, 4H, 2×NCH$_2$), 4.10 (q, 4H, 2×CH$_2$CH$_3$, $^3J$=7.1 Hz), 2.45 (t, 4H, 2×CH$_2$CO$_2$H, CH$_2$, $^3J$=6.5 Hz), 2.09 (s, 12H, 4×CH$_3$), 2.00-1.92 (m, 4H, 2×CH$_2$), 1.20 ppm (t, 6H, 2×CH$_2$CH$_3$, $^3J$=7.1 Hz). $^{13}$C NMR (100 MHz, CD$_3$OD): $\delta$=177.5, 174.9, 169.4, 150.8, 140.8, 133.7, 132.0, 131.2, 129.3, 129.0, 126.4, 123.4, 112.2, 103.2, 79.5, 69.2, 61.6, 52.5, 34.5, 28.1, 23.2, 14.5 ppm. UV/VIS (EtOH): $\lambda_{max}$ (E$_{rel}$): 598 (1.0), 558 nm (0.64). UV/VIS (solid/cotton): $\lambda_{max}$ (E$_{rel}$): 560 (1.0), 556 nm (0.97). UV/VIS (solid/wool): $\lambda_{max}$ (E$_{rel}$): 598 (1.0), 557 nm (0.98). UV/VIS (solid/hair): $\lambda_{max}$ (E$_{rel}$): 598 (1.0), 555 nm (0.94). Fluorescence (EtOH): $\lambda_{max}$ (I$_{rel}$): 610 (1.0), 660 nm (0.52). Fluorescence (solid/cotton): $\lambda_{max}$ (I$_{rel}$): 670 (1.0), 643 nm (0.95). Fluorescence (solid/wool): $\lambda_{max}$ (I$_{rel}$): 631 (1.0), 664 nm (0.95). Fluorescence (solid/hair): $\lambda_{max}$ (I$_{rel}$): 625 (1.0), 664 nm (0.96). Fluorescence quantum yield (CHCl$_3$, $\lambda_{exc}$=559 mm E$_{562/1\ cm}$=0.0128, Reference: S-13 with $\Phi$=1.00): 0.43. HRMS (ESI) (C$_{43}$H$_{53}$N$_2$O$_4^+$): calculated 685.4000. found 685.4010, $\Delta$=1.0 mmu.

3,3'-Di-(5-ethoxycarbonylpentyl)-1,1,1',1'-tetramethyl-1H-dibenzo[e]indocarbocyanine bromide (3o)

3-(5-Ethoxycarbonylpentyl)-1,1,2-trimethyl-1H-benzo[e]indolenium bromide (2o, 400 mg, 0.93 mmol), pyridine (1.5 mL) and orthoformic acid triethyl ester (0.30 mL, 1.85 mmol) were reacted (100° C.) and worked up as described for 3,3'-di-(2-carboxyethyl)-1,1,1',1'-tetramethyl-1H-dibenzo[e]indocarbocyanine bromide (3a). In this case, purification via flash chromatography was dispensed with because the product decomposes to the corresponding acid. Yield: 363 mg (50%) gold gleaming solid, which forms violet, red-fluorescing solutions. IR (ATR): $\tilde{v}$=3312 (w), 2930 (m), 2859 (m), 2361 (w), 2338 (w), 1724 (s), 1626 (w), 1587 (w), 1553 (s), 1520 (m), 1480 (m), 1423 (s), 1356 (m), 1278 (w), 1225 (m), 1169 (w), 1143 (w), 1126 (w), 1071 (w), 10.12 (m), 972 (w), 927 (m), 898 (w), 877 (w), 806 (w), 747 (w), 726 (w), 685 cm$^{-1}$ (w). $^1$H NMR (200 MHz, CD$_3$OD): $\delta$=8.78 (t, 1H, H$_{aromatic}$, $^3J$=13.6 Hz), 8.31 (d, 2H, H$_{aromatic}$, $^3J$=7.8 Hz), 8.10-8.00 (m, 4H, H$_{aromatic}$, H$_{allyl}$), 7.75-7.63 (m, 4H, H$_{aromatic}$), 7.57-7.49 (m, 2H, H$_{aromatic}$), 6.55 (d, 2H, H$_{allyl}$, $^3J_E$=13.4 Hz), 4.30 (t, 4H, 2×NCH$_2$, $^3J$=7.5 Hz), 4.07 (q, 4H, 2×CH$_2$CH$_3$, $^3J$=7.1 Hz), 2.37 (t, 4H, 2×CH$_2$CO$_2$H, CH$_2$, $^3J$=7.0 Hz), 2.11 (s, 12H, 4×CH$_3$), 2.00-1.81 (m, 4H, 2×CH$_2$), 1.79-1.55 (m, 8H, 4×CH$_2$), 1.18 ppm (t, 6H, 2×CH$_2$CH$_3$, $^3J$=7.1 Hz). $^{13}$C NMR (100 MHz, CD$_3$OD): $\delta$=177.4, 175.3, 150.8, 145.7, 140.9, 135.0, 133.7, 132.0, 131.2, 129.6, 126.4, 123.4, 112.3, 103.3, 61.5, 52.5, 45.9, 34.9, 28.6, 28.1, 27.3, 25.8, 16.8, 14.8 ppm. UV/VIS (EtOH): $\lambda_{max}$ (E$_{rel}$): 591 (1.0), 554 nm (0.73). UV/VIS (solid/cotton): $\lambda_{max}$ (E$_{rel}$): 598 (1.0), 554 nm (0.97), UV/VIS (solid/wool): $\lambda_{max}$ (E$_{rel}$): 599 (1.0), 554 nm (0.99). UV/VIS (solid/hair): $\lambda_{max}$ (E$_{rel}$): 600 (1.0), 554 nm (0.95). Fluorescence (EtOH): $\lambda_{max}$ (I$_{rel}$): 615 (1.0), 655 nm (0.57). Fluorescence (solid/cotton): $\lambda_{max}$ (I$_{rel}$): 666 (1.0), 642 nm (0.93). Fluorescence (solid/wool): $\lambda_{max}$ (I$_{rel}$): 664 (1.0), 638 nm (0.98). Fluorescence (solid/hair): $\lambda_{max}$ (I$_{rel}$): 636 (1.0), 665 nm (0.92). Fluorescence quantum yield (CHCl$_3$, $\lambda_{exc}$=558 nm, E$_{558/1\ cm}$=0.0138, Reference: S-13 with $\Phi$=1.00): 0.36. HRMS (ESI) (C$_{47}$H$_{57}$N$_2$O$_4^+$): calculated 713.4313. found 713.4331, $\Delta$=1.8 mmu.

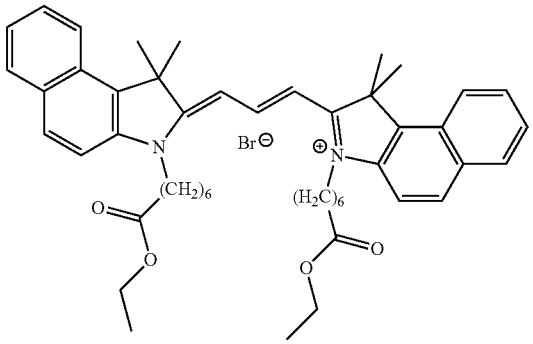

3,3'-Di-(6-ethoxycarbonylhexyl)-1,1,1',1'-tetramethyl-1H-dibenzo[e]indocarbocyanine bromide (3p)

3-(6-Ethoxycarbonylhexyl)-1,1,2-trimethyl-1H-benzo[e]indolenium bromide (2p, 95.0 mg, 0.213 mmol), 3-picoline (1.00 mL) and orthoformic acid triethyl ester (0.070 mL, 0.426 mmol) were reacted (100° C.) and worked up as described for 3,3'-di-(2-carboxyethyl)-1,1,1',1'-tetramethyl-1H-dibenzo[e]indocarbocyanine bromide (3a). In this case, purification via flash chromatography was dispensed with because the product decomposes to the corresponding acid. Yield: 49 mg (28%). IR (ATR): $\tilde{v}$=3064 (w), 2936 (s), 2864 (w), 2540 (w), 2361 (s), 2338 (s), 2162 (w), 1718 (s, br), 1654 (w), 1636 (w), 1558 (m), 1522 (m), 1507 (w), 1431 (s), 1362 (w), 1226 (w), 1174 (m), 1155 (w), 1017 (w), 938 (m), 814 (w), 750 (w), 668 cm$^{-1}$ (m). UV/VIS (EtOH): $\lambda_{max}$ (E$_{rel}$): 588 (1.0), 553 nm (0.76). Fluorescence (EtOH): $\lambda_{max}$ (I$_{rel}$): 608 (1.0), 655 nm (0.51). Fluorescence quantum yield (CHCl$_3$, $\lambda_{exc}$=561 nm, E$_{562/1\ cm}$=0.0154, Reference: S-13 with $\Phi$=1.00): 0.35. HRMS (ESI) (C$_{49}$H$_{61}$N$_2$O$_4^+$): calculated 741.4626. found 741.4613, $\Delta$=1.3 mmu.

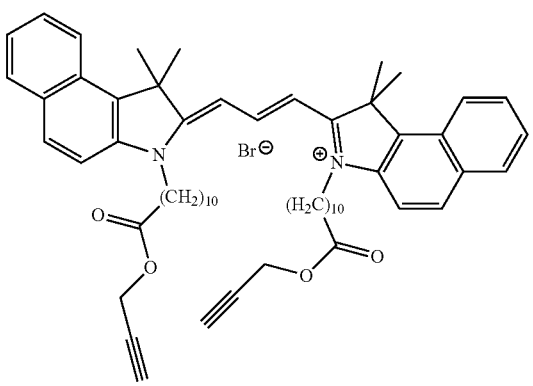

3,3'-Di-(10-propargyloxycarbonyldecyl)-1,1,1',1'-tetramethyl-1H-dibenzo[e]indocarbocyanine bromide (3q)

3-(10-Propargyloxycarbonyldecyl)-1,1,2-trimethyl-1H-benzo[e]indolenium bromide (2q) (900 mg, 1.76 mmol), pyridine (2.0 mL) and orthoformic acid triethyl ester (0.6 mL, 3.51 mmol) were reacted (100° C.) and worked up as described for 3,3'-di-(2-carboxyethyl)-1,1,1',1'-tetramethyl-1H-dibenzo[e]indocarbocyanine bromide (3a). In this case, purification via flash chromatography was dispensed with because the product decomposes. Yield: 621 mg (37%) gold gleaming solid, which forms violet, red-fluorescing solutions. UV/VIS (EtOH): $\lambda_{max}$ (E$_{rel}$): 591 (1.0), 550 nm (0.77). Fluorescence (EtOH): $\lambda_{max}$ (I$_{rel}$): 609 (1.0), 655 nm (0.50). HRMS (ESI) (C$_{59}$H$_{73}$N$_2$O$_4^+$): calculated 873.5565. found 873.5571, $\Delta$=0.6 mmu.

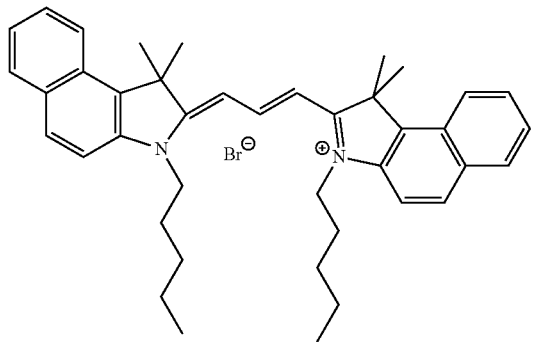

3,3'-Di-(pentyl)-1,1,1',1'-tetramethyl-1H-dibenzo[e]indocarbocyanine bromide (6j; reference compound)

1,1,2-Trimethyl-3-pentyl-1H-benzo[e]indolenium bromide (100 mg, 0.277 mmol) was dissolved in pyridine (1.0 mL) under an N$_2$ protective atmosphere, heated to 100° C., slowly combined dropwise with orthoformic acid triethyl ester (0.1 mL, 0.5 mmol), heated for 2 h at 100° C., allowed to cool, combined with diethyl ether (20 mL) and aspirated. Yield: 71 mg (79%), gold gleaming solid, which forms violet solutions that fluoresce with an intense red color. Melting point >150° C. (decomposition). IR (ATR): $\tilde{v}$=3393 (s), 3133 (w), 3060 (m), 2979 (w), 2941 (w), 2871 (w), 2054 (w), 1634 (s), 1584 (w), 1555 (m), 1519 (m), 1487 (s), 1466 (w), 1446 (w), 1428 (w), 1388 (w), 1356 (w), 1318 (w), 1227 (w), 1173 (s), 1127 (w), 1060 (w), 1029 (w), 973 (w), 937 (w), 880 (w), 807 (w), 778 (m), 680 cm$^{-1}$ (s). $^1$H NMR (200 MHz, CD$_3$OD): $\delta$=8.79 (t, 1H, H$_{diene}$, $^3$J$_E$=13.5 Hz), 8.30 (d, 2H, H$_{aromatic}$, $^3$J=8.5 Hz), 8.07-8.02 (m, 4H, H$_{aromatic}$), 7.71-7.67 (m, 2H, H$_{aromatic}$), 7.64 (d, 2H, H$_{aromatic}$, $^3$J=8.8 Hz) 7.55-7.51 (m, 2H, H$_{aromatic}$), 6.54 (d, 2H, H$_{diene}$, $^3$J$_E$=13.5 Hz), 4.29 (t, 4H, 2×NCH$_2$, $^3$J=7.5 Hz), 2.11 (s, 12H, 4×CH$_3$), 1.96-1.89 (m, 4H, 2×CH$_2$), 1.55-1.44 (m, 8H, 4×CH$_2$), 0.97 ppm (t, 6H, 2×CH$_3$, $^3$J=7.2 Hz). $^{13}$C NMR (100 MHz, CD$_3$OD): $\delta$=177.8, 147.2, 146.1, 141.3, 134.1, 132.4, 131.6, 130.0, 126.8, 112.6, 103.5, 59.0, 52.8, 45.9, 30.5, 29.0, 28.5, 24.0, 17.1, 14.7 ppm. UV/Vis (EtOH): $\lambda_{max}$ (E$_{rel}$): 590 (1.0), 552 nm (0.70). UV/Vis (solid/cellulose): $\lambda_{max}$ (E$_{rel}$): 600 (1.0), 553 nm (0.98). UV/Vis (solid/wool): $\lambda_{max}$ (E$_{rel}$): 539 (1.0), 600 nm (0.93). Fluorescence (EtOH): $\lambda_{max}$ (I$_{rel}$): 607 (1.0), 657 nm (0.50). Fluorescence (solid/cellulose): $\lambda_{max}$ (I$_{rel}$): 671 (1.0). Fluorescence (solid/wool): $\lambda_{max}$ (I$_{rel}$): 623 (1.0), 662 nm (0.79). Fluorescence quantum yield (CHCl$_3$, $\lambda_{exc}$=553 nm, E$_{553\ nm/1\ cm}$=0.0133; Reference: S-13 with $\Phi$=1.00): 0.20. HRMS (ESI) (C$_{41}$H$_{49}$N$_2^+$): calculated 569.3890. found 569.3884, $\Delta$=-0.6 mmu.

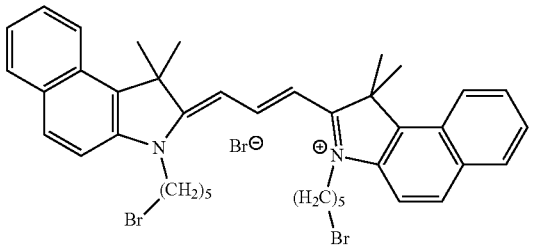

3,3'-Di-(5-bromopentyl)-1,1,1',1'-tetramethyl-1H-dibenzo[e]indocarbocyanine bromide (3y)

3-(5-Bromopentyl)-1,1,2-trimethyl-1H-benzo[e]indolenium bromide (400 mg, 0.911 mmol), pyridine (2.0 mL) and orthoformic acid triethyl ester (0.300 mL, 1.82 mmol) were reacted (2.5 h at 120° C.) and worked up analogously to 3,3'-di-(pentyl)-1,1,1',1'-tetramethyl-1H-dibenzo[e]indocarbocyanine bromide (6j). Flash chromatography (RP 18, methanol/H$_2$O/1 M HCl 10:1:0.4) resulted in decomposition of the dye. For this reason, it is used without chromatographic purification. Melting point >100° C. IR (ATR): $\tilde{\nu}$=3408 (m), 2970 (s), 2927 (m), 2865 (m), 2362 (w), 1728 (w), 1627 (w), 1588 (w), 1558 (m), 1520 (w), 1430 (m), 1372 (m), 1296 (w), 1278 (w), 1249 (w), 1226 (w), 1191 (w), 1100 (s), 1013 (m), 936 (m), 863 (w), 809 (w), 787 (w), 748 (w), 728 (w), 701 (w), 653 cm$^{-1}$ (w). $^1$H NMR (200 MHz, CD$_3$OD): δ=8.82 (t, 1H, H$_{diene}$, $^3J_E$=13.7 Hz), 8.27-8.26 (m, 2H, H$_{aromatic}$), 8.16-8.09 (m, 4H, H$_{aromatic}$), 7.71-7.64 (m, 4H, H$_{aromatic}$), 7.56-7.51 (m, 2H, H$_{aromatic}$), 7.08 (d, 2H, H$_{diene}$, $^3J_E$=13.8 Hz), 4.34-4.33 (m, 8H, 2×NCH$_2$, 2×CH$_2$Br), 2.11 (s, 12H, 4×CH$_3$), 2.05-1.94 ppm (m, 12H, 6×CH$_2$). UV/Vis (EtOH): λ$_{max}$ (E$_{rel}$): 592 (1.0), 553 nm (0.86). UV/Vis (solid/cellulose): λ$_{max}$ (E$_{rel}$): 558 (1.0), 597 nm (0.98). UV/Vis (solid/wool): λ$_{max}$ (E$_{rel}$): 556 (1.0), 598 nm (0.97). Fluorescence (EtOH): λ$_{max}$ (I$_{rel}$): 612 (1.0), 662 nm (0.61). Fluorescence (solid/cellulose): λ$_{max}$ (I$_{rel}$): 678 (1.0), 632 nm (0.51). Fluorescence (solid/wool): λ$_{max}$ (I$_{rel}$): 678 (1.0), 628 nm (0.46). Fluorescence quantum yield (CHCl$_3$, λ$_{exc}$=549 nm, E$_{549\ nm/1\ cm}$=0.0254; Reference S-13 with Φ=1.00): 0.15. HRMS (ESI): (M$^+$-C$_{36}$H$_{37}$N$_2^+$) calculated 497.2951. found 497.2951, Δ=0 mmu.

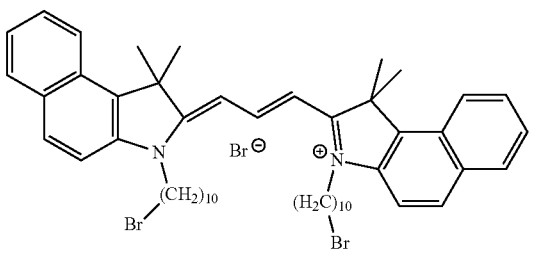

3,3'-Di-(5-bromodecyl)-1,1,1',1'-tetramethyl-1H-dibenzo[e]indocarbocyanine bromide (3x)

3-(10-Bromodecyl)-1,1,2-trimethyl-1H-benzo[e]indolenium bromide (250 mg, 0.491 mmol), pyridine (2.0 mL) and orthoformic acid triethyl ester (0.16 mL, 0.98 mmol) were reacted (2 h at 120° C.) and worked up analogously to 3,3'-di-(pentyl)-1,1,1',1'-tetramethyl-1H-dibenzo[e]indocarbocyanine bromide (6j), and purified via flash chromatography (RP 18, methanol/H$_2$O/1 M HCl 1:1:0.4 for the application, methanol/H$_2$O/1 M HCl 2:1:0.4 for removal of byproducts, and methanol/H$_2$O/1 M HCl 10:1:0.4 for elution of the dye). Yield: 170 mg (73%), gold gleaming solid which forms violet, intense red fluorescing solutions. Melting point: 113° C. IR (ATR): $\tilde{\nu}$=3387 (m), 3058 (w), 2919 (s), 2851 (s), 1722 (m), 1627 (w), 1588 (w), 1555 (m), 1520 (m), 1479 (w), 1468 (w), 1427 (s), 1358 (m), 1226 (m), 1171 (w), 1144 (w), 1111 (m), 1013 (w), 933 (m), 898 (w), 808 (m), 787 (w), 748 (w), 727 (w), 700 (w), 686 (w), 653 cm$^{-1}$ (w). $^1$H NMR: severe aggregation in concentrated solution, resulting in strongly broadened signals. UV/Vis (EtOH): λ$_{max}$ (E$_{rel}$): 593 (1.0), 553 nm (0.73). UV/Vis (solid/cellulose): λ$_{max}$ (E$_{rel}$): 601 (1.0), 557 nm (0.96). UV/Vis (solid/wool): λ$_{max}$ (E$_{rel}$): 602 (1.0), 570 nm (0.97). Fluorescence (EtOH): nλ$_{max}$ (I$_{rel}$) 608 (1.0), 658 nm (0.53). Fluorescence (solid/cellulose): λ$_{max}$ (I$_{rel}$): 672 (1.0), 650 nm (0.89). Fluorescence (solid/wool): λ$_{max}$ (I$_{rel}$): 671 (1.0), 651 nm (0.87). Fluorescence quantum yield (CHCl$_3$, λ$_{exc}$=558 nm, E$_{558\ nm/1\ cm}$=0.0125; Reference S-13 with Φ=1.00): 0.10. HRMS (ESI): (M$^+$-C$_{41}$H$_{47}$N$_2^+$): calculated 567.3734. found 567.3736, Δ=0.2 mmu.

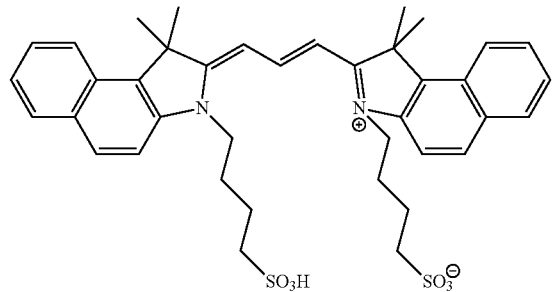

3,3'-Di-(4-sulfobutyl)-1,1,1',1'-tetramethyl-1H-dibenzo[e]indocarbocyanine bromide (3t)

3-(4-Sulfobutyl)-1,1,2-trimethyl-1H-benzo[e]indole (500 mg, 1.40 mmol) was dissolved in pyridine (2.0 mL) under an N$_2$ protective atmosphere, heated to 116° C. and slowly combined dropwise with orthoformic acid triethyl ester (0.50 mL, 2.9 mmol) (blue-violet color), heated for 2 h under reflux, allowed to cool, precipitated with diethyl ether, freed from solvent via decantation, dried under vacuum and purified via flash chromatography (RF 18, methanol/H$_2$O/1 M HCl 1:1: 0.4 for the application, methanol/H$_2$O/1 M HCl 2:1:0.4 for removal of byproducts, and methanol/H$_2$O/1 M HCl 10:1:0.4 for elation of the dye). Yield: 430 mg (88%) gold gleaming solid, which forms violet, intensely red fluorescing solutions. Melting point >250° C. IR (ATR): $\tilde{\nu}$=3454 (w), 3054 (m), 2973 (w), 2933 (w), 2860 (w), 1626 (m), 1588 (w), 1555 (s), 1519 (m), 1490 (s), 1426 (s), 1369 (m), 1348 (w), 1124 (w), 1030 (m), 1012 (m), 977 (w), 948 (m), 925 (m), 891 (w), 805 (w), 767 (w), 740 (w), 728 (w), 688 (w), 650 cm$^{-1}$ (w). $^1$H NMR (200 MHz, CD$_3$OD): δ=8.74 (t, 1H, H$_{diene}$, $^3J_E$=13.5 Hz), 8.28 (d, 2H, H$_{aromatic}$, $^3J$=8.2 Hz), 8.02 (t, 4H, H$_{aromatic}$, $^3J$=7.5 Hz), 7.67 (t, 4H, H$_{aromatic}$, $^3J$=8.5 Hz), 7.50 (t, 2H, H$_{aromatic}$, $^3J$=7.5 Hz), 6.59 (d, 2H, H$_{diene}$, $^3J_E$=13.7 Hz), 4.42-4.26 (m, 4H, 2×NCH$_2$), 3.05-2.87 (m, 4H, 2×CH$_2$SO$_3$H), 2.02-2.19 ppm (m, 20H, 4×CH$_3$, 4×CH$_2$). $^{13}$C NMR (100 MHz, CD$_3$OD): δ=176.8, 149.3, 139.5, 133.4, 132.2, 130.5, 129.7, 127.9, 127.4, 124.8, 121.9, 110.9, 56.9, 51.0, 43.8, 26.6, 26.2, 22.8, 22.2, 16.9 ppm. UV/Vis (EtOH): $\lambda_{max}$ ($E_{rel}$): 591 (1.0), 553 nm (0.68). UV/Vis (solid/cellulose): $\lambda_{max}$ ($E_{rel}$): 593 (1.0), 559 nm (0.99). UV/Vis (solid/hair): $\lambda_{max}$ ($E_{rel}$): 553 (1.0), 593 nm (0.90). Fluorescence (EtOH): $\lambda_{max}$ ($I_{rel}$): 620 (1.0), 660 nm (0.50). Fluorescence (solid/cellulose): $\lambda_{max}$ ($I_{rel}$): 662 (1.0), 630 nm (0.96). Fluorescence (solid/wool): $\lambda_{max}$ ($I_{rel}$): 667 (1.0), 640 nm (0.98). Fluorescence (solid/hair): $\lambda_{max}$ ($I_{rel}$): 621 (1.0), 661 nm (0.67). Fluorescence quantum yield (CHCl$_3$, $\lambda_{exc}$=559 nm, $E_{559\ nm/1\ cm}$=0.0124; Reference: S-13 with $\Phi$=1.00): 0.32, HRMS (ESI) ($C_{39}H_{45}N_2O_6S_2$): calculated 701.2719. found 701.2726 $\Delta$=0.7 mmu.

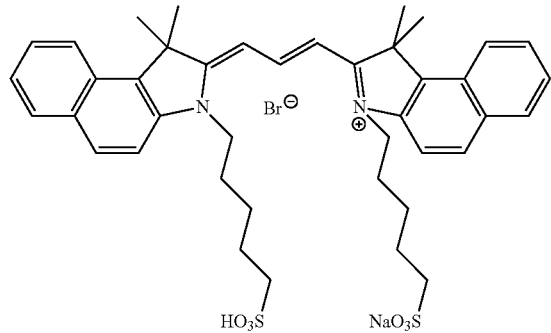

3,3'-Di-(5-sulfopentyl)-1,1,1',1'-tetramethyl-1H-dibenzo[e]indocarbocyanine bromide (3u)

3-(5-Sulfopentyl)-1,1,2-trimethyl-1H-benzo[e]indolenium bromide sodium salt (122 mg, 0.264 mmol), pyridine (1.3 mL), methanol (1 mL) and orthoformic acid triethyl ester (0.080 mL, 0.52 mmol) were reacted (2 h at 100° C.) and worked up analogously to 3,3'-di-(pentyl)-1,1,1',1'-tetramethyl-1H-dibenzo[e]indocarbocyanine bromide (6j), repeatedly dissolved in a small amount of ethanol, precipitated with diethyl ether, decanted, and purified via flash chromatography (RP 18, methanol/H$_2$O/1 M HCl 1:1:0.4 for the application, methanol/H$_2$O/1 M HCl 2:1:0.4 for removal of byproducts, and methanol/H$_2$O/1 M HCl 10:1:0.4 for elution of the dye). Yield: 56.0 mg (51%) gold gleaming solid, which forms violet, intensely red fluorescing solutions. IR (ATR): $\tilde{v}$=3376 (w), 3058 (w), 2969 (w), 2931 (m), 2860 (w), 1702 (w), 1626 (w), 1586 (w), 1553 (s), 1520 (s), 1479 (m), 1422 (s), 1357 (m), 1224 (m), 1184 (m), 1171 (m), 1142 (m), 1126 (m), 1074 (w), 1036 (w), 1013 (w), 968 (w), 926 (s), 899 (w), 884 (w), 870 (w), 810 (m), 786 (w), 745 (w), 698 (w), 686 (w), 676 (w), 652 cm$^{-1}$ (w). $^1$H NMR (200 MHz, CD$_3$OD): $\delta$=8.78 (t, 1H, H$_{diene}$, $^3J_E$=13.8 Hz), 8.30 (d, 2H, H$_{aromatic}$, $^3J$=8.7 Hz), 8.04 (t, 4H, H$_{aromatic}$, $^3J$=7.8 Hz), 7.68 (t, 4H, H$_{aromatic}$, $^3J$=8.0 Hz), 7.57-7.48 (m, 2H, H$_{aromatic}$), 6.60 (d, 2H, H$_{diene}$, $^3J_E$=13.9 Hz), 4.32 (t, 4H, 2×NCH$_2$, $^3J$=7.8 Hz), 2.85-2.81 (m, 4H, 2×CH$_2$SO$_3$H), 2.11 (s, 12H, 4×CH$_3$), 1.99-1.69 ppm (m, 12H, 6×CH$_2$). UV/Vis (EtOH): $\lambda_{max}$ ($E_{rel}$): 590 (1.0), 553 nm (0.68), UV/Vis (solid/cellulose): $\lambda_{max}$ ($E_{rel}$): 599 (1.0), 553 nm (0.97). UV/Vis (solid/wool): $\lambda_{max}$ ($E_{rel}$): 600 (1.0), 553 nm (0.96). Fluorescence (EtOH): $\lambda_{max}$ ($I_{rel}$): 611 (1.0), 655 nm (0.54). Fluorescence (solid/cellulose): $\lambda_{max}$ ($I_{rel}$): 664 (1.0), 636 nm (0.93). Fluorescence (solid/wool): $\lambda_{max}$ ($I_{rel}$): 667 (1.0), 644 nm (0.84). Fluorescence quantum yield (CHCl$_3$, $\lambda_{exc}$=553 nm, $E_{553\ nm/1\ cm}$=0.0158; Reference: S-13 with $\Phi$=1.00): 0.13. HRMS (ESI) ($C_{41}H_{47}N_2Na_2O_6S_2^+$): calculated 773.2671. found 773.2669, $\Delta$=−0.2 mmu.

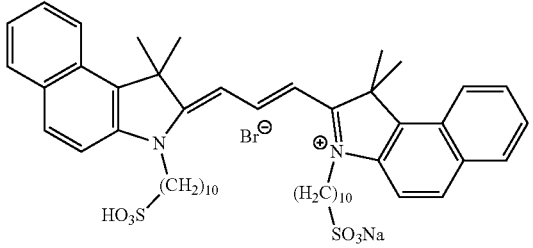

3,3'-Di-(10-sulfodecyl)-1,1,1',1'-tetramethyl-1H-dibenzo[e]indocarbocyanine bromide (3v)

3-(10-Sulfodecyl)-1,1,2-trimethyl-1H-benzo[e]indolenium bromide sodium salt (152 mg, 0.285 mmol), 3-picoline (1.5 mL) and orthoformic acid triethyl ester (0.09 mL, 0.57 mmol) were reacted (2 h at 100° C.) and worked up analogously to 3,3'-di-(pentyl)-1,1,1',1'-tetramethyl-1H-dibenzo[e]indocarbocyanine bromide (6j). Since the dye decomposes on the chromatography column (RP 18, methanol/H$_2$O/1 M HCl), it was used without further purification. Yield: 185 mg. IR (ATR): $\tilde{v}$=3409 (w), 3055 (w), 2974 (w), 2926 (s), 2853 (m), 1705 (m), 1624 (w), 1588 (w), 1554 (s), 1519 (m), 1479 (m), 1425 (s), 1352 (m), 1278 (w), 1227 (m), 1169 (w), 1144 (w), 1124 (w), 1044 (w), 1012 (m), 974 (w), 931 (s), 898 (w), 806 (m), 787 (w), 747 (w), 727 (w), 684 (w), 652 (w), 637 (w), 612 cm$^{-1}$ (w). $^1$H NMR (200 MHz, CD$_3$OD): $\delta$=8.76-8.64 (m, 1H, H$_{diene}$), 8.34-8.32 (m, 2H, H$_{aromatic}$), 8.03-7.96 (m, 4H, H$_{aromatic}$), 7.71-7.67 (m, 4H, H$_{aromatic}$), 7.37-7.31 (m, 2H, H$_{aromatic}$), 6.55 (d, 2H, H$_{diene}$, $^3J_E$=13.9 Hz), 4.38-4.20 (m, 4H, 2×NCH$_2$), 2.51-2.40 (m, 4H, 2×CH$_2$SO$_3$H), 2.10-1.99 (m, 16H, 4×CH$_3$, 2×CH$_2$), 1.95-1.80 (m, 8H, 4×CH$_2$), 1.52-1.25 ppm (m, 20H, 10×CH$_2$). UV/Vis (EtOH): $\lambda_{max}$ ($E_{rel}$): 592 (1.0), 553 nm (0.72). UV/Vis (solid/cellulose): $\lambda_{max}$ ($E_{rel}$): 601 (1.0), 559 nm (0.95). UV/Vis (solid/wool): $\lambda_{max}$ ($E_{rel}$): 599 (1.0), 556 nm (0.97). Fluorescence (EtOH): $\lambda_{max}$ ($I_{rel}$): 609 (1.0), 658 nm (0.52). Fluorescence (solid/cellulose): $\lambda_{max}$ ($I_{rel}$): 637 (1.0), 665 nm (0.97). Fluorescence (solid/wool): $\lambda_{max}$ ($I_{rel}$): 630 (1.0), 662 nm (0.92). Fluorescence quantum yield (CHCl$_3$, $\lambda_{exc}$=554 nm, $E_{554\ nm/1\ cm}$=0.0170; Reference: S-13 with $\Phi$=1.00): 0.14.

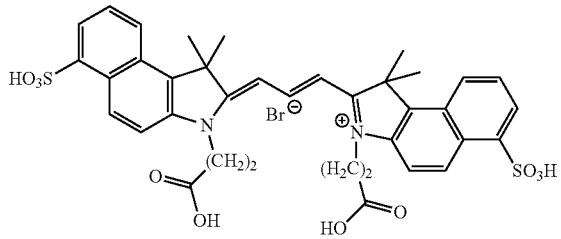

3,3'-Di-(2-carboxyethyl)-1,1,1',1'-tetramethyl-1H-disulfobenzo[e]indocarbocyanine bromide (6b)

1,1,2-Trimethyl-1,1,2-Trimethyl-1H-sulfobenzo[e]indole (4, 245 mg, 0.847 mmol) was dissolved in 3-picoline (1.0 mL)

and methanol (0.3 mL) under an $N_2$ protective atmosphere, heated to 120° C., combined with 3-bromopropionic acid (388 mg, 2.54 mmol), stirred for 10 min at 120° C., combined with orthoformic acid triethyl ester (0.300 mL, 1.69 mmol) (blue-violet color) for 2 h at 120° C., allowed to cool, precipitated with diethyl ether (20 mL), aspirated and purified via flash chromatography (RP 18, methanol/$H_2O$/1 M HCl 1:1:0.4 for the application, methanol/$H_2O$/1 M HCl 2:1:0.4 for removal of byproducts, and methanol/$H_2O$/1 M HCl 10:1: 0.4 for elation of the dye). Yield: 200 mg (58%) gold gleaming solid, which forms violet, intensely red fluorescing solutions. Melting point >180° C. (decomposition). IR (ATR): $\tilde{v}$3387 (w), 2972 (w), 2927 (w), 2858 (w), 2367 (w), 1719 (w), 1626 (w), 1562 (s), 1490 (s), 1453 (s), 1414 (m), 1384 (m), 1168 (m, br), 1124 (w), 1097 (w), 1060 (w), 1046 (w), 1025 (s), 979 (m), 927 (m), 808 (m), 76.1 (w), 735 (w), 689 (m), 643 cm$^{-1}$ (m). $^1$H NMR (200 MHz, $CD_3OD$): δ=8.80 (t, 1H, $H_{allyl}$, $^3J_E$=13.4 Hz), 8.35-8.25 (m, 4H, $H_{aromatic}$), 8.08-7.97 (m, 4H, $H_{aromatic}$), 7.58-7.47 (m, 2H, $H_{aromatic}$), 6.56 (d, 2H, $H_{allyl}$, $^3J_E$=13.6 Hz), 4.59-4.53 (m, 4H, 2×$NCH_2$), 2.94 (t, 4H, 2×$CH_2CO_2H$, $^3J$=7.3 Hz), 2.10 ppm (s, 12H, 4×$CH_3$). UV/Vis (EtOH): $\lambda_{max}$ ($E_{rel}$): 588 (1.0), 554 nm (0.74). UV/Vis (solid/cellulose): $\lambda_{max}$ ($E_{rel}$): 591 (1.0), 550 nm (0.99). UV/Vis (solid/wool): $\lambda_{max}$ ($E_{rel}$): 565 (1.0), 589 nm (0.99). Fluorescence (EtOH): $\lambda_{max}$ ($I_{rel}$): 612 (1.0), 657 nm (0.41). Fluorescence (solid/cellulose): $\lambda_{max}$ ($I_{rel}$): 648 (1.0), 662 nm (0.94). Fluorescence (solid/wool): $\lambda_{max}$ ($I_{rel}$): 629 (1.0), 664 nm (0.72). Fluorescence quantum yield ($CHCl_3$, $\lambda_{exc}$=482 nm, $E_{482\ nm/1\ cm}$=0.0197; Reference: S-13 with Φ=1.00): 0.21. MS (FAB$^+$): m/z: 733.6 [M$^+$ ($C_{37}H_{37}N_2O_{10}S^+$].

(w), 806 (w), 746 (w), 689 (m), 657 (w), 630 cm$^{-1}$ (w). $^1$H NMR (200 MHz, $CD_3OD$): δ=8.79 (t, 1H, $H_{diene}$, $^3J_E$=13.4 Hz), 8.47-8.35 (m, 4H, $H_{aromatic}$), 8.22-8.05 (m, 4H, $H_{aromatic}$), 7.72 (t, 2H, $H_{aromatic}$, $^3J$=7.7 Hz), 6.54 (d, 2H, $H_{diene}$, $^3J_E$=13.7 Hz), 4.29 (t, 4H, 2×$NCH_2$, $^3J$=8.7 Hz), 2.31-2.21 (m, 4H, 2×$CH_2CO_2H$), 2.11 (s, 12H, 4×$CH_3$), 1.97-1.85 (m, 4H, 2×$CH_2$) 1.59-1.13 ppm (m, 28H, 14×$CH_2$). UV/Vis (EtOH): $\lambda_{max}$ ($E_{rel}$): 593 (1.0), 554 nm (0.68), UV/Vis (solid/cellulose): $\lambda_{max}$ ($E_{rel}$): 594 (1.0), 553 nm (0.94). UV/Vis (solid/wool): $\lambda_{max}$ ($E_{rel}$): 598 (1.0), 556 nm (0.94). Fluorescence (EtOH): $\lambda_{max}$ ($I_{rel}$): 608 (1.0), 656 nm (0.48). Fluorescence (solid/cellulose): $\lambda_{max}$ ($I_{rel}$): 663 (1.0), 646 nm (0.89). Fluorescence (solid/wool): $\lambda_{max}$ ($I_{rel}$): 664 (1.0), 641 nm (0.91). Fluorescence quantum yield ($CHCl_3$, $\lambda_{exc}$=554 nm, $E_{554\ nm/1\ cm}$=0.0157; Reference: S-13 with Φ=1.00): 0.31. HRMS (ESI) ($C_{53}H_{69}N_2O_{10}S_2^+$): calculated 957.4388. found 957.4392 Δ=−0.4 mmu.

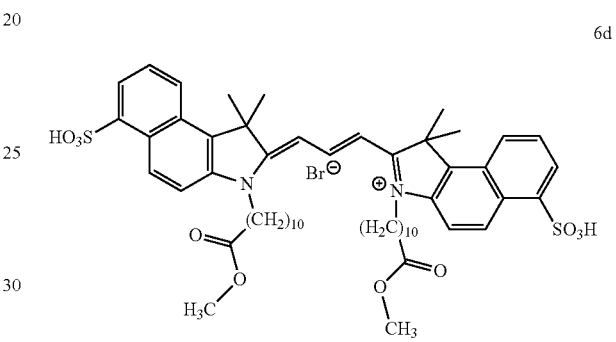

6d

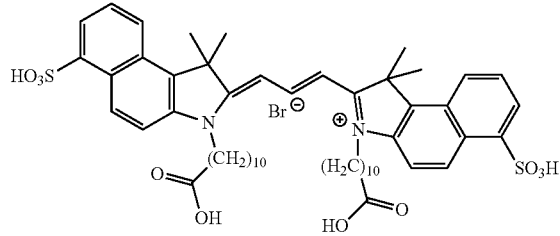

6c 3,3'-Di-(10-carboxydecyl)-1,1,1',1'-tetramethyl-1H-disulfobenzo[e]indocarbocyanine bromide (6c)

3-(10-Carboxyldecyl)-1,1,2-trimethyl-1H-sulfobenzo[e]indole (2f, 100 mg, 0.180 mmol) was dissolved in pyridine (1.0 mL) and methanol (0.3 mL) under an $N_2$ protective atmosphere, heated to 120° C., very slowly combined dropwise with orthoformic acid triethyl ester (0.06 mL, 0.36 mmol), with a second portion of pyridine (0.5 mL) and orthoformic acid triethyl ester (0.03 mL, 0.18 mmol), heated for 2 h at 120° C., allowed to cool, precipitated with diethyl ether (20 mL), aspirated, and purified via flash chromatography (RP 18, methanol/$H_2O$/1 M HCl 1:1:0.4 for the application, methanol/$H_2O$/1 M HCl 2:1:0.4 for removal of byproducts, and methanol/$H_2O$/1 M HCl 10:1:0.4 for elution of the dye). Yield: 66.0 mg (71%) gold gleaming solid, which forms violet, intensely red fluorescing solutions. Melting point >150° C. (decomposition). IR (ATR): $\tilde{v}$=3392 (w), 2922 (s), 2852 (s), 2362 (w), 1718 (s, br), 1585 (w), 1554 (s), 1515 (m), 1480 (m), 1420 (s), 1361 (m), 1274 (w), 1224 (w), 1166 (m), 1131 (m), 1100 (m), 1029 (w), 1015 (w), 932 (s), 898 (w), 827

3,3'-Di-(10-methoxycarbonyldecyl)-1,1,1',1'-tetramethyl-1H-disulfobenzo[e]indocarbocyanine bromide (6d)

1,1,2-Trimethyl-1H-sulfobenzo[e]indole (4, 267 mg, 0.923 mmol), pyridine (0.5 mL), methanol (0.25 mL), 11-bromoundecanoic acid methyl ester (0.700 mL, 2.78 mmol, 10 min, 120° C.), orthoformic acid triethyl ester (0.300 mL, 1.86 mmol) and diethyl ether (20 mL) were reacted (1.5 h at 120° C.) and worked up under a nitrogen atmosphere analogously to 3,3'-di-(2-carboxyethyl)-1,1,1',1'-tetramethyl[e]indocarbocyanine bromide (6b). Since the dye decomposes on the chromatographic column (RP 18, methanol/$H_2O$/1 M HCl), it was instead repeatedly dissolved in a small amount of ethanol and precipitated with diethyl ether. Yield: 200 mg (41%) gold gleaming solid, which forms violet, intensely red fluorescing solutions. Melting point >150° C. (decomposition), IR (ATR): $\tilde{v}$=3430 (m), 3180 (w), 3140 (w), 3072 (m), 2927 (m), 2855 (w), 2158 (w), 1712 (m), 1637 (s), 1583 (w), 1544 (m), 1489 (s), 1466 (w), 1393 (w), 1316 (w), 1176 (s), 1100 (m), 1044 (w), 1021 (s), 931 (w), 857 (w), 754 (s), 681 (s), 658 (m), 643 (w), 608 cm$^{-1}$ (w). $^1$H NMR (200 MHz, $CD_3OD$): δ=8.50-8.42 (m, 1H, $H_{diene}$), 8.40-8.24 (m, 6H, $H_{aromatic}$), 7.90-7.64 (m, 4H, $H_{aromatic}$), 6.56 (d, 2H, $H_{diene}$, $^3J_E$=13.9 Hz), 4.35-4.30 (m, 4H, 2×$NCH_2$), 3.31 (s, 6H, 2×$OCH_3$), 2.29-2.20 (m, 4H, 2×$CH_2CO_2CH_3$), 2.10 (s, 12H, 4×$CH_3$), 1.98-1.88 (m, 4H, $CH_2$), 1.65-1.45 (m, 12H, 6×$CH_2$), 1.38-1.30 ppm (m, 16H, 8×$CH_2$). UV/Vis (EtOH): $\lambda_{max}$ ($E_{rel}$): 587 (1.0), 556 nm (0.78). UV/Vis (solid/cellulose): $\lambda_{max}$ ($E_{rel}$): 588 (1.0), 555 nm (0.97), UV/Vis (solid/wool): $\lambda_{max}$ ($E_{rel}$): 551 (1.0), 586 nm (0.87). Fluorescence (EtOH): $\lambda_{max}$ ($I_{rel}$): 607 (1.0), 657 nm (0.48). Fluorescence (solid/cellulose): $\lambda_{max}$ ($I_{rel}$): 624 (1.0), 660 nm (0.74). Fluorescence (solid/wool): $\lambda_{max}$ ($I_{rel}$): 617 (1.0), 660 nm (0.60). Fluorescence quantum yield (CHCl$_3$, $\lambda_{exc}$=556 nm, $E_{556 nm/1 cm}$=0.0159; Reference S-13 with $\Phi$=1.00): 0.25. MS (FAB$^-$): m/z: 1063.3 [M$^-$ (C$_{55}$H$_{72}$BrN$_2$O$_{10}$S$^-$].

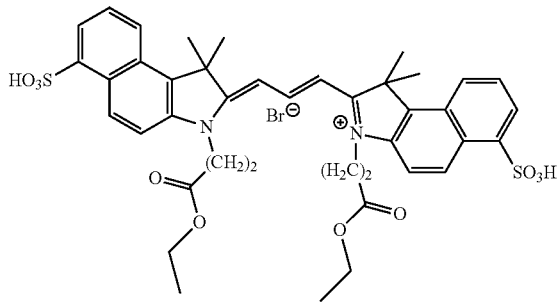

3,3'-Di-(2-ethoxycarbonylethyl)-1,1,1',1'-tetramethyl-1H-disulfobenzo[e]indocarbocyanine bromide
(6e)

3-(2-Ethoxycarbonylethyl)-1,1,2-trimethyl-1H-sulfobenzo[e]indole (5e, 210 mg, 0.446 mmol), 3-picoline (1.0 mL) and orthoformic acid triethyl ester (0.15 mL, 0.89 mmol) were reacted (2 h at 120° C.) and worked up analogously to 3,3'-di-(pentyl)-1,1,1',1'-tetramethyl-1H-dibenzo[e]indocarbocyanine bromide (6j) and purified via flash chromatography (RP 18, methanol/H$_2$O/1 M HCl 1:1:0.4 for the application and methanol/H$_2$O/1 M HCl 10:1:0.4 for elution of the dye). Yield: 100 mg (52%) gold gleaming solid, which forms violet, intensely red fluorescing solutions. Melting point >150° C. (decomposition). IR (ATR): $\tilde{v}$=3411 (w), 3068 (w), 2951 (w), 2924 (s), 2854 (m), 1725 (m), 1623 (w), 1584 (w), 1559 (w), 1514 (w), 1478 (w), 1458 (w), 1426 (m), 1390 (w), 1362 (w), 1168 (s), 1100 (m), 1060 (w), 1030 (s), 940 (m), 827 (w), 809 (w), 762 (w), 692 (m), 649 (w), 624 cm$^{-1}$ (w). $^1$H NMR (CDCl$_3$): Substantial signal broadening due to aggregation. UV/Vis (EtOH): $\lambda_{max}$ ($E_{rel}$): 596 (1.0), 569 nm (0.79). UV/Vis (solid/cellulose): $\lambda_{max}$ ($E_{rel}$): 599 (1.0), 564 nm (0.97). UV/Vis (solid/wool): $\lambda_{max}$ ($E_{rel}$): 563 (1.0), 597 nm (0.94). Fluorescence (EtOH): $\lambda_{max}$ ($I_{rel}$): 610 (1.0), 660 nm (0.51). Fluorescence (solid/cellulose): $\lambda_{max}$ ($I_{rel}$): 654 (1.0), 633 nm (0.98). Fluorescence (solid/wool): $\lambda_{max}$ ($I_{rel}$): 627 (1.0), 662 nm (0.88). Fluorescence quantum yield (CHCl$_3$, $\lambda_{exc}$=559 nm, $E_{559 nm/1 cm}$=0.0145; Reference: S-13 with $\Phi$=1.00): 0.18.

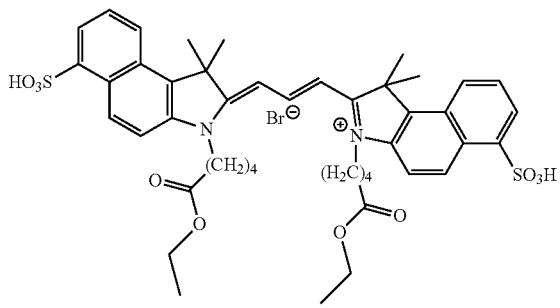

3,3'-Di-(4-ethoxycarbonylbutyl)-1,1,1',1'-tetramethyl-1H-disulfobenzo[e]indocarbocyanine bromide
(6f)

1,1,2-Trimethyl-1H-sulfobenzo[e]indole (4, 250 mg, 0.864 mmol), 3-picoline (1.0 mL), methanol (0.2 mL), 5-bromopentanoic acid ethyl ester (0.40 mL, 2.6 mmol, 10 min, 120° C.), orthoformic acid triethyl ester (0.300 mL, 1.73 mmol) and diethyl ether (20 mL) were reacted (2 h, 120° C.) and worked up (the dye decomposes as soon as after one day, forming with a yellow color) analogously to 3,3'-di-(2-carboxyethyl)-1,1,1',1'-tetramethyl-1H-disulfobenzo[e]indocarbocyanine bromide (6b) and purified via flash chromatography (RP 18, methanol/H$_2$O/1 M HCl 1:1:0.4 for the application and methanol/H$_2$O/1 M HCl 10:1:0.4 for elution of the dye). Yield: 33.0 mg (8%) gold gleaming solid, which forms violet, intensely red fluorescing solutions. Melting point >150° C. (decomposition). IR (ATR): $\tilde{v}$3362 (w), 2971 (w), 2931 (w), 1724 (w), 1623 (w), 1564 (m), 1519 (w), 1492 (s), 1455 (m), 1416 (m), 1386 (in), 1185 (s, br), 1099 (m), 1060 (w), 1046 (w), 1027 (s), 980 (m), 929 (m), 809 (m), 763 (w), 736 (w), 691 (m), 643 cm$^{-1}$ (m). UV/Vis (EtOH): $\lambda_{max}$ ($E_{rel}$): 588 (1.0), 556 nm (0.76). UV/Vis (solid/cellulose): $\lambda_{max}$ ($E_{rel}$): 591 (1.0), 550 nm (0.98). UV/Vis (solid/wool): $\lambda_{max}$ ($E_{rel}$): 559 (1.0), 591 nm (0.95). Fluorescence (EtOH): $\lambda_{max}$ ($I_{rel}$): 613 (1.0), 662 nm (0.40). Fluorescence (solid/cellulose): $\lambda_{max}$ ($E_{rel}$): 636 (1.0), 671 nm (0.76). Fluorescence (solid/wool): $\lambda_{max}$ ($I_{rel}$): 637 (1.0), 664 nm (0.93). Fluorescence quantum yield (CHCl$_3$, $\lambda_{exc}$=478 nm, $E_{478 nm/1 cm}$=0.0170; Reference: S-13 with $\Phi$=1.00): 0.11. HRMS (ESI) (C$_{45}$H$_{51}$N$_2$O$_{10}$S$_2^-$): calculated 843.2991. found 843.3797, $\Delta$=80.6 mmu.

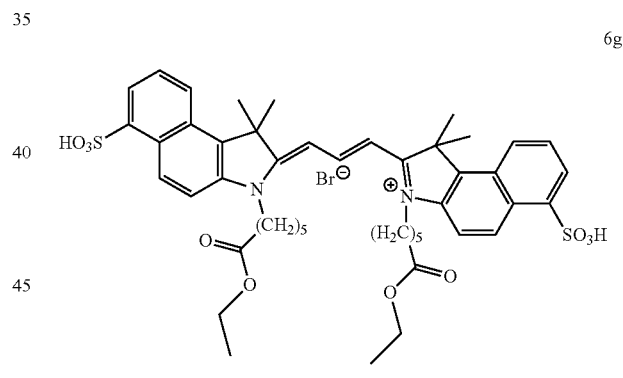

3,3'-Di-(5-ethoxycarbonylpentyl)-1,1,1',1'-tetramethyl-1H-disulfobenzo[e]indocarbocyanine bromide
(6g)

3-(5-Ethoxycarbonylpentyl)-1,1,2-trimethyl-1H-sulfobenzo[e]indole (100 mg, 0.195 mmol), 3-picoline (1.0 mL), methanol (0.3 mL), orthoformic acid triethyl ester (0.06 mL, 0.39 mmol) and diethyl ether (20 mL) were reacted (2 h at 120° C.) and worked up analogously to 3,3'-di-(pentyl)-1, 1,1',1'-tetramethyl-1H-dibenzo[e]indocarbocyanine bromide and purified via flash chromatography (RP 18, methanol/H$_2$O/1 M HCl 1:1:0.4 for the application and methanol/H$_2$O/1 M HCl 10:1:0.4 for elution of the dye). Yield: 20 mg (2%) gold gleaming solid, which forms violet, intensely red fluorescing solutions. Melting point >150° C. (decomposition). IR (ATR): $\tilde{v}$=3410 (w), 3069 (w), 2926 (m), 2856 (w), 1710 (s), 1623 (w), 1556 (m), 1515 (m), 1480 (m), 1426 (s), 1362 (m), 1157 (s), 1135 (w), 1100 (m), 1029 (s), 1018 (s), 932 (s), 901 (w), 808 (w), 764 (w), 693 (m), 627 cm$^{-1}$ (w). $^1$H NMR (200 MHz, CD$_3$OD): δ=8.79 (t, 1H, H$_{diene}$, $^3J_E$=13.9 Hz), 8.45-8.34 (m, 4H, H$_{aromatic}$), 8.21-8.04 (m, 4H, H$_{aromatic}$), 7.72 (t, 2H, H$_{aromatic}$, $^3J$=7.7 Hz), 6.55 (d, 2H, H$_{diene}$, $^3J_E$=13.8 Hz), 4.35-4.24 (m, 4H, 2×NCH$_2$), 3.88-3.77 (m, 4H, 2×CH$_2$CH$_3$), 2.38-2.31 (m, 4H, 2×CH$_2$CO$_2$), 2.10 (s, 12H, 4×CH$_3$), 1.99-1.87 (m, 8H, 4×CH$_2$), 1.78-1.61 (m, 4H, 2×CH$_2$) 1.00-0.90 ppm (m; 6H, 2×CH$_2$CH$_3$). In addition, signals of the carboxylic acid appear in the NMR spectrum as the saponification product of the ethyl ester function. $^{13}$C NMR (100 MHz, CD$_3$OD): δ=175.9, 142.2, 133.1, 132.7, 131.6, 129.9, 128.6, 127.7, 126.6, 125.6, 123.9, 113.3, 112.4, 52.6, 45.5, 34.7, 28.3, 27.4, 25.8, 24.5, 13.8 ppm, UV/Vis (EtOH): λ$_{max}$ (E$_{rel}$): 593 (1.0), 557 nm (0.69). UV/Vis (solid/cellulose): λ$_{max}$ (E$_{rel}$): 597 (1.0), 556 nm (0.97). UV/Vis (solid/wool): λ$_{max}$ (E$_{rel}$): 561 (1.0), 596 nm (0.98). Fluorescence (EtOH): λ$_{max}$ (I$_{rel}$): 610 (1.0), 660 nm (0.51). Fluorescence (solid/cellulose): λ$_{max}$ (I$_{rel}$): 622 (1.0), 654 nm (0.97). Fluorescence (solid/wool): λ$_{max}$ (I$_{rel}$): 660 (1.0), 641 nm (0.96). Fluorescence quantum yield (CHCl$_3$, λ$_{exc}$=559 nm, E$_{559\ nm/1\ cm}$=0.0115; Reference: S-13 with Φ=1.00): 0.22.

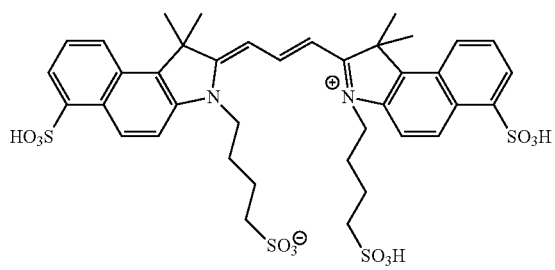

3,3'-Di-(4-sulfobutyl)-1,1,1',1'-tetramethyl-1H-disulfobenzo[e]indocarbocyanine bromide (6a)

3-(4-Sulfobutyl)-1,1,2-trimethyl-1H-sulfobenzo[e]indole (140 mg, 0.276 mmol), pyridine (1.5 mL), orthoformic acid triethyl ester (0.090 mL, 0.55 mmol) and diethyl ether (15 mL) were reacted (2 h at 120° C.) and worked up analogously to 3,3'-di-(pentyl)-1,1,1',1'-tetramethyl-1H-dibenzo[e]indocarbocyanine bromide, repeatedly dissolved in a small amount of ethanol and precipitated with diethyl ether, and purified via flash chromatography (RP 18, methanol/H$_2$O/1 M HCl 1:1:0.4 for the application and methanol/H$_2$O/1 M HCl 10:1:0.4 for elution of the dye). Yield: 100 mg (77%) gold gleaming solid, which forms violet, intensely red fluorescing solutions. Melting point >150° C. IR (ATR): ν̃3774 (w), 3450 (s, br), 2976 (w), 2938 (w), 2873 (w), 2361 (w), 2331 (w), 2008 (w), 1691 (w), 1640 (w), 1556 (s), 1515 (m), 1484 (m), 1431 (s), 1364 (m), 1277 (w), 1173 (s, br), 1103 (w), 1034 (m), 940 (m), 900 (w), 812 (w), 783 (w), 756 (w), 692 (w), 636 (w), 610 cm$^{-1}$ (w). $^1$H NMR (200 MHz, CD$_3$OD): δ=8.71-8.54 (m, 7H, H$_{diene}$, H$_{aromatic}$), 8.40-8.33 (m, 2H, H$_{aromatic}$), 7.80-7.64 (m, 2H, H$_{aromatic}$), 6.63 (d, 2H, H$_{diene}$, $^3J_E$=13.2 Hz), 4.37-4.34 (m, 4H, 2×NCH$_2$), 2.98-2.97 (m, 4H, 2×CH$_2$SO$_3$H), 2.11-2.00 (m, 16H, 4×CH$_3$, 2×CH$_2$), 1.65 ppm (t, 4H, 2×CH$_2$, $^3J$=7.7 Hz). UV/Vis (EtOH): λ$_{max}$ (E$_{rel}$): 593 (1.0), 556 nm (0.66). UV/Vis (solid/cellulose): λ$_{max}$ (E$_{rel}$): 546 (1.0), 586 nm (0.94). UV/Vis (solid/wool): λ$_{max}$ (E$_{rel}$): 554 (1.0), 588 nm (0.92). Fluorescence (EtOH): λ$_{max}$ (I$_{rel}$): 608 (1.0), 655 nm (0.47). Fluorescence (solid/cellulose): λ$_{max}$ (I$_{rel}$): 654 (1.0), 629 nm (0.94). Fluorescence (solid/wool): λ$_{max}$ (I$_{rel}$): 631 (1.0), 661 nm (0.99). Fluorescence quantum yield (CHCl$_3$, λ$_{exc}$=556 nm, E$_{556\ nm/1\ cm}$=0.0099; Reference: S-13 with Φ=1.00): 0.33. HRMS (ESI) (C$_{39}$H$_{45}$N$_2$O$_{12}$S$_4^+$): calculated 861.1850. found 861.1851, Δ=0.1 mmu.

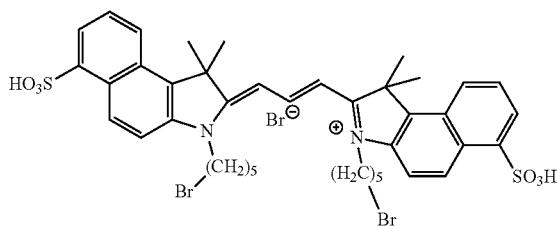

3,3'-Di-(5-brompentyl)-1,1,1',1'-tetramethyl-1H-disulfobenzo[e]indocarbocyanine bromide (6h)

1,1,2-Trimethyl-1H-sulfobenzo[e]indole (215 mg, 0.743 mmol), 3-picoline (1.5 mL), methanol (1.0 mL), 1,5-dibromopentane (0.30 mL, 2.2 mmol, 10 min, 120° C.), orthoformic acid triethyl ester (0.250 mL, 1.45 mmol) and diethyl ether (20 mL) were reacted (2 h, 120° C.) and worked up analogously to 3,3'-di-(2-carboxyethyl)-1,1,1',1'-tetramethyl-1H-disulfobenzo[e]indocarbocyanine bromide, and purified via flash chromatography (RP 18, methanol/H$_2$O/1 M HCl 1:1:0.4 for the application and methanol/H$_2$O/1 M HCl 10:1:0.4 for elution of the dye). Yield: 98 mg (27%) gold gleaming solid, which forms violet, intensely red fluorescing solutions. Melting point >75° C. (decomposition). IR (ATR): ν̃=3398 (s, br), 3056 (m), 3036 (w), 2866 (w), 2074 (w), 1634 (m), 1592 (w), 1559 (w), 1505 (s), 1483 (w), 1463 (w), 1387 (w), 1325 (w), 1250 (w), 1202 (m), 1155 (m), 1098 (w), 1048 (m), 1031 (m), 928 (w), 808 (m), 749 (w), 683 (m), 657 cm$^{-1}$ (w). UV/Vis (EtOH): λ$_{max}$ (E$_{rel}$): 590 (1.0), 559 nm (0.78). UV/Vis (solid/cellulose): λ$_{max}$ (E$_{rel}$): 600 (1.0), 565 nm (0.95). UV/Vis (solid/wool): λ$_{max}$ (E$_{rel}$): 558 (1.0), 587 nm (0.95). Fluorescence (EtOH): λ$_{max}$ (I$_{rel}$): 611 (1.0), 659 nm (0.50). Fluorescence (solid/cellulose): λ$_{max}$ (I$_{rel}$): 626 (1.0), 660 nm (0.83). Fluorescence (solid/wool): λ$_{max}$ (I$_{rel}$): 615 (1.0) 658 nm (0.60). Fluorescence quantum yield (CHCl$_3$, λ$_{exc}$=553 nm, E$_{553\ nm/1\ cm}$=0.0124; Reference: S-13 with Φ=1.00): 0.19.

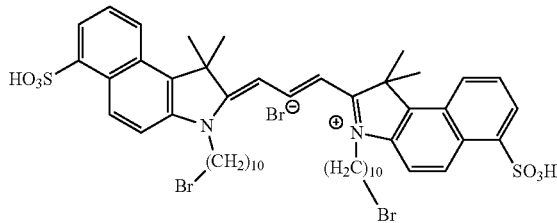

3,3'-Di-(10-bromodecyl)-1,1,1',1'-tetramethyl-1H-disulfobenzo[e]indocarbocyanine bromide (6i)

1,1,2-Trimethyl-1H-sulfobenzo[e]indole (205 mg, 0.708 mmol), 3-picoline (1.0 mL), methanol (0.3 mL), 1,10-dibromodecane (0.50 mL, 2.1 mmol, 10 min, 120° C.), orthoformic acid triethyl ester (0.24 mL, 1.4 mmol) and diethyl ether (20 mL) were reacted (2 h, 120° C.) and worked up analogously to 3,3'-di-(2-carboxyethyl)-1,1,1',1'-tetramethyl-1H-disulfobenzo[e]indocarbocyanine bromide (6b), and purified via flash chromatography (RP 18, methanol/H$_2$O/1 M HCl 1:1:0.4 for the application and methanol/H$_2$O/1 M HCl 10:1:0.4 for elution of the dye). Yield: 58 mg (14%) gold gleaming solid, which forms violet, intensely red fluorescing solutions. Melting point >100° C. (decomposition). IR (ATR): $\tilde{v}$=3387 (s), 3059 (w), 2927 (s), 2855 (s), 1706 (m), 1635 (m), 1591 (w), 1562 (m), 1504 (m), 1489 (m), 1456 (m), 1414 (w), 1388 (w), 1364 (w), 1186 (s), 1098 (m), 1047 (w), 1029 (s), 981 (m), 932 (m), 811 (m), 765 (w), 734 (w), 688 (m), 645 cm$^{-1}$ (m). UV/Vis (EtOH): $\lambda_{max}$ (E$_{rel}$): 587 (1.0), 555 nm (0.77). UV/Vis (solid/cellulose): $\lambda_{max}$ (E$_{rel}$): 500 (1.0), 591 nm (0.75). UV/Vis (solid/wool): $\lambda_{max}$ (E$_{rel}$): 551 (1.0), 591 nm (0.95). Fluorescence (EtOH): $\lambda_{max}$ (I$_{rel}$): 614 (1.0), 661 nm (0.42). Fluorescence (solid/cellulose): $\lambda_{max}$ (I$_{rel}$): 620 (1.0), 655 nm (0.70). Fluorescence (solid/wool): $\lambda_{max}$ (I$_{rel}$): 628 (1.0), 665 nm (0.77). Fluorescence quantum yield (CHCl$_3$, $\lambda_{exc}$=481 nm, E$_{481\ nm/1\ cm}$=0.0181; Reference: S-13 with Φ=1.00): 0.13.

Biological Tests

BSS Plus®

Sterile intraocular rinse solution, obtained by mixing two partial solutions 1:1. Partial solution 1:1 ml, contains 7.44 mg NaCl, 0.395 mg KCl, 0.433 mg Na$_2$HPO$_4$, in water and, when applicable, HCl or NaOH, to control the physiological pH. Partial solution 2:1 mL contains 3.85 mg CaCl$_2$.2H$_2$O, 5 mg MgCl$_2$.6H$_2$O, 23 mg glucose, 4.6 mg glutathione disulfide in water.

For the dye test, in each case 5 mg dye was dissolved in 500 μL ethanol and diluted to 2 mL with BSS Plus solution as the stock solution, and then correspondingly further diluted. As an alternative, one can prepare stock solutions of the dye by dissolving, for example, 5 mg dye in 1 mL distilled water, adding 7 mL BSS solution and then combining with 1 mL NaCl solution having an osmolality of 620 (approximately 2%) in order to restore the original osmolality of the BSS solution (308). This stock solution can be correspondingly further diluted with BSS solution as required.

Dye Tests on Porcine Eyes

Enucleated porcine eyes were used having a post mortem time period of a few hours. To dye the lens capsule, the cornea was first removed. Thereafter, the iris was resected and the capsular support was severed. The lens with intact lens capsule was removed and placed in a bowl filled with BSS. The lenses were thereafter incubated with the dyes according to the invention at various concentrations and then rinsed after one minute. The dye pattern was photographically documented, whereby the coloration was assessed without additional illumination, and fluorescence was assessed with illumination (Xenon lamp, halogen lamp with typical endoillumination source and fiber optics).

The lens capsule is a very good model for dyeing due to the fact that it is a basal membrane, as is the ILM of the retina. Both structures are important target structures in eye surgery.

The following table shows the results of the dyeing tests at various dye concentrations (+++ indicates visually assessed very strong coloration, ++ indicates good coloration; + indicates satisfactory coloration and − indicates weak or absent coloration).

| Dye | 1.0 | 0.5% | 0.25% | 0.025% | 0.0025% |
|---|---|---|---|---|---|
| 3a |  | ++ | ++ | + | − |
| 3c |  | +++ | +++ | − | − |
| 3d |  | +++ | + | − | − |
| 3e |  | ++ | ++ | − | − |
| 3g |  | ++ | ++ | − | − |
| 3h |  | +++ | ++ | + | − |
| 3i |  | ++ | + | + | − |
| 3j |  | ++ | + | − | − |
| 3k |  | ++ | + | − | − |
| 3l |  | +++ | +++ | + | − |
| 3m |  | +++ | ++ | − | − |
| 3n |  | ++ | + | − | − |
| 3o |  | ++ | ++ | − | − |
| 3t |  | +++ | ++ | + | − |
| 3u | + | − |  |  |  |
| 3v | − | − |  |  |  |
| 6a | +++ | +++ |  |  |  |
| 6b | +++ | +++ |  |  |  |
| 6c | ++ | ++ |  |  |  |
| 6d | decomposed | decomposed |  |  |  |
| 6e | decomposed | decomposed |  |  |  |
| 6f | decomposed | decomposed |  |  |  |
| 6g | ++ | ++ |  |  |  |
| 6h | decomposed | decomposed |  |  |  |
| 6i | decomposed | decomposed |  |  |  |

Toxicity Studies Using an Established Cell Culture Model; MTT Assay

For the investigation of the effect of dyes on cells, ARPE-19 cell material and primary human RPE cells were maintained under serum-free conditions for 24 h. RPE cells were obtained and cultured as described in Eibl K. H., Banas B., Schoenfeld C. L., May C. A., Neubauer A. S., Priglinger S., Kampik A. and Welge-Lussen U., "Alkylphosphocholines inhibit proliferation of human retinal pigment epithelial cells," Invest. Ophthalmol Vis. Sci. 2003; 44: 3556-3561. After three washing steps with PBS, the cells were incubated for 30, 60, 120 and 300 seconds with 300 μL BSS Plus® solutions containing in each case 0.5%, 0.25% and 0.1% 3,3'-di-(4-sulfobutyl)-1,1,1',1'-tetramethyl-1H-dibenzo[e] indocarbocyanine (3t). ICG was used as a reference, in the same concentrations and for the same incubation times, for the ARPE 19 as well as the primary RPE cells. The relatively long incubation times are reasonable in order to also detect weak toxic effects, even though they do not reflect the clinical use of the dyes. Excess dye was removed by washing the cells with BSS Plus® three times, and then the cell growth experiment (cell proliferation experiment) was carried out. Control tests were carried out with BSS Plus® without additives, and with the addition of H$_2$O$_2$ (200 μL/mL).

The tetrazolium dye reduction assay (MTT; 3-(4,5-dimethylthiazole-2-yl)-2,5-diphenyl tetrazolium bromide) was used to determine the survival rate of the cells. The MTT test according to Mosmann was carried out in modified form (K. H. Eibl, B. Banas, C. L. Schoenfeld, C. A. May, A. S. Neubauer, S. Priglinger, A. Kampik, U. Welge-Lussen, Invest. Ophthalmol. Vis. Sci. 2003, 44, 3556-3561). The medium was removed, the cells were combined with PBS and 1000 μL/well MTT solution (1.5 mL MTT stock solution, 2 mg/mL in PBS and 28.5 mL DMEM), RPE cells were incubated for 1 h at 37° C., the resulting formazan crystals were dissolved by adding dimethylsulfoxide (DMSO; 1000 μL/well), and the absorption was measured at 550 nm, using a scanning multiwell spectrophotometer (Molecular Probes, Garching, Germany). The results were related to the average percentage of control growth (control proliferation). The experiments were repeated in triplicate three times. ARPE-19 cells from the same test series and RPE cells incubated in BSS served as controls. The statistical comparison of the tests at various dye concentrations was carried out using SPSS (Mann-Whitney U test).

The MTT test which is conducted is well-established for determining cell vitality, but is dependent on the colorimetric measurement of a blue (550 nm) formazan product. The light absorption which is based on same partially overlaps with the absorption of the investigated dye. For this reason, control experiments were conducted to evaluate potential interferences in the test. Cell monolayers were treated with the dye as in the other tests, but the absorption readout was conducted without prior application of MTT. We did not find any differences after treatment with dyes, compared to the BSS control tests. A comparison with ICG as a reference showed a significant increase in the survival rate for cells using the dye according to the invention. The tests were repeated in triplicate three times.

FIG. 3 shows the number of ARPE-19 and RPE cells measured with the described colorimetric method (MTT) after treatment with the dye: ARPE-19: A: 0.5%, B: 0.25%, C: 0.1% of the dye 3t; RPE: D: 0.5%, E: 0.25%, F: 0.1% of the dye 3t. AVS4 refers to the substance 3t.

The invention claimed is:

1. A method of dying ophthalmic tissue for use in a surgical treatment or a diagnostic method comprising contacting said tissue with a contrast agent of Formula (I),

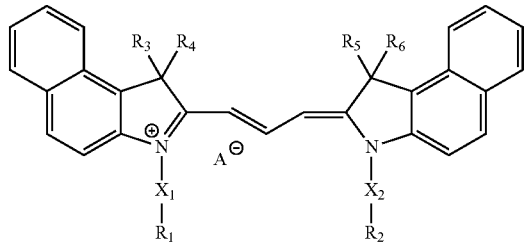

Formula (I)

wherein
$X_1$ and $X_2$ are independently selected from 1 to 12 $CH_2$ units, one or more of which may be independently substituted by a carbonyl group, an oxygen atom, a sulfur atom, a cis- or trans-CH=CH— group, wherein a CH— unit may also be substituted by a nitrogen atom, an acetylenic C≡C— group, a divalent phenyl, pyridine, or thiophene radical, a divalent naphthalene radical, wherein one or two CH— groups may be substituted by nitrogen atoms, a divalent anthracene radical, wherein one or two CH— groups may be substituted by nitrogen atoms, and wherein up to 12 individual hydrogen atoms of the $CH_2$ units may each independently from each other, and also on the same C atom, be substituted by the halogens fluorine, chlorine, bromine, or iodine, or a cyano group, or by a linear alkyl chain with up to 18 C atoms, wherein 1 to 6 $CH_2$ units may each independently be substituted by a carbonyl group, an oxygen atom, a sulfur atom, a cis- or trans-CH=CH— group, wherein a CH— unit may also be substituted by a nitrogen atom, an acetylenic C≡C— group, a divalent phenyl, pyridine, or thiophene radical, a divalent naphthalene radical, wherein one or two CH— groups may be substituted by nitrogen atoms, or a divalent anthracene radical, wherein one or two CH— groups may be substituted by nitrogen atoms;

$R_1$ and $R_2$ are independently selected from a carboxylic acid group (—COOH), a carboxylic acid ester group, a sulfonic acid group (—SO$_3$H) or a halogen atom;

$R_3$, $R_4$, $R_5$ and $R_6$ are independently selected from hydrogen and $C_1$-$C_6$ alkyl; and $A^-$ represents an optional anion that is capable of balancing the formal charge of a positively charged nitrogen atom.

2. The method of claim 1 wherein said tissue is the basal membrane of the eye.

3. The method of claim 1 wherein said tissue is the ILM.

4. The method of claim 1 wherein said tissue is the lens capsule of the eye.

5. The method of claim 1, wherein $R_1$ and $R_2$ are carboxylic acid.

6. The method of claim 1, wherein R1 and R1 are carboxylic acid ester.

7. The method of claim 1, wherein
$X_{1A}$ and $X_{2A}$ are independently selected from 1 to 12 $CH_2$ units, wherein 1 to 3 units may each independently be substituted by an oxygen atom or a sulfur atom, and/or may be substituted by a divalent phenyl radical; and wherein up to 4 individual hydrogen atoms of the $CH_2$ units may each independently, and also on the same C atom, be substituted by the halogens fluorine, chlorine, bromine or iodine, or a cyano group, or by a linear alkyl chain having up to 6 C atoms; and
R1 and R2 are carboxylic acid.

8. The method of claim 1,
wherein
$X_1$ and $X_2$ are independently selected from 1 to 12 $CH_2$ units, wherein 1 to 3 units may each independently be substituted by an oxygen atom or a sulfur atom, and/or may be substituted by a divalent phenyl radical; and wherein up to 4 individual hydrogen atoms of the $CH_2$ units may each independently, and also on the same C atom, be substituted by the halogens fluorine, chlorine, bromine or iodine, or a cyano group, or by a linear alkyl chain having up to 6 C atoms; and
$R_1$ and $R_2$ are carboxylic acid ester.

9. The method of claim 1,
wherein
$X_1$ and $X_2$ are independently selected from 1 to 12 $CH_2$ units, wherein 1 to 3 units may each independently be substituted by an oxygen atom or a sulfur atom, and/or may be substituted by a divalent phenyl radical; and wherein up to 4 individual hydrogen atoms of the $CH_2$ units may each independently, and also on the same C atom, be substituted by the halogens fluorine, chlorine, bromine or iodine, or a cyano group, or by a linear alkyl chain having up to 6 C atoms; and
$R_1$ and $R_2$ are sulfonic acid.

* * * * *